US012612585B2

(12) United States Patent
Kilpatrick et al.

(10) Patent No.: US 12,612,585 B2
(45) Date of Patent: Apr. 28, 2026

(54) CELL CULTURE BIOREACTOR WITH ZONE CONTROL

(71) Applicant: ABEC, Inc., Bethlehem, PA (US)

(72) Inventors: Shane Alexander Jaques Kilpatrick, Mississauga (CA); Scott Raymond Pundsack, Georgetown (CA); Andrew Michael Pundsack, Georgetown (CA)

(73) Assignee: ABEC, INC., Bethlehem, PA (US)

( * ) Notice: Subject to any disclaimer, the term of this patent is extended or adjusted under 35 U.S.C. 154(b) by 890 days.

(21) Appl. No.: 17/792,132

(22) PCT Filed: Feb. 4, 2021

(86) PCT No.: PCT/CA2021/050124
§ 371 (c)(1),
(2) Date: Jul. 11, 2022

(87) PCT Pub. No.: WO2021/155469
PCT Pub. Date: Aug. 12, 2021

(65) Prior Publication Data
US 2023/0052695 A1      Feb. 16, 2023

Related U.S. Application Data

(60) Provisional application No. 63/002,504, filed on Mar. 31, 2020, provisional application No. 62/970,305, filed on Feb. 5, 2020.

(51) Int. Cl.
*C12M 1/12* (2006.01)
*C12M 1/00* (2006.01)
(Continued)

(52) U.S. Cl.
CPC ............ *C12M 25/10* (2013.01); *C12M 23/34* (2013.01); *C12M 27/02* (2013.01); *C12M 29/04* (2013.01);
(Continued)

(58) Field of Classification Search
CPC ...... C12M 29/10; C12M 29/16; C12M 29/04; C12M 41/48; C12M 41/00; C12M 27/10;
(Continued)

(56) References Cited

U.S. PATENT DOCUMENTS 4,937,196 A      6/1990   Wrasidlo
5,366,625 A      11/1994  Pedersen et al.
(Continued)

FOREIGN PATENT DOCUMENTS

CA      2566841 A1    11/2005
CN      103861455 A   6/2014
(Continued)

OTHER PUBLICATIONS

European Patent Application No. 19869945.6, European Search Opinion, dated Feb. 6, 2022.
(Continued)

*Primary Examiner* — Michael L Hobbs

(57) ABSTRACT

A cell culture bioreactor has membranes divided into a plurality of zones. The membranes may include perfusion membranes carrying a liquid media and/or gas transfer membranes. The bioreactor has one or more sensors configured to collect data from one or more locations within the bioreactor. The supply of one or more of the gaseous and/or liquid media to a selected zone or zones may be controlled. In some examples, the supply includes a background supply and a selectable incremental supply. The bioreactor may be used to grow cells in suspension. Liquid media circulates within an extra-capillary space of the bioreactor. In some examples, a portion of cells is permitted for a period of time to be restrained within one or more zones of the membranes. Elements of a reactor may be made in a mold. A reactor may be operated in a fed-batch process.

12 Claims, 34 Drawing Sheets

(51) Int. Cl.
   *C12M 1/06* (2006.01)
   *C12M 1/36* (2006.01)
(52) U.S. Cl.
   CPC ............ *C12M 29/10* (2013.01); *C12M 29/16*
                    (2013.01); *C12M 41/48* (2013.01)
(58) Field of Classification Search
   CPC ...... C12M 27/16; C12M 27/02; C12M 39/00;
                C12M 23/34; B01D 63/031; B01D
                63/043; B01D 63/026; B01D 61/20;
                B01D 61/22; B01D 61/026; B01D
                2313/205; B01D 2313/21; B01D 2313/90;
                B01D 2313/903; B01D 2315/02; B01D
                                                   2317/08
   See application file for complete search history.

(56)                References Cited

U.S. PATENT DOCUMENTS

| | | | | | |
|---|---|---|---|---|---|
| 5,516,691 | A | 5/1996 | Gerlach | | |
| 5,622,857 | A | 4/1997 | Goffe | | |
| 5,658,797 | A | 8/1997 | Bader | | |
| 6,228,607 | B1 | 5/2001 | Kersten et al. | | |
| 6,284,451 | B1 | 9/2001 | Funatsu | | |
| 6,372,495 | B1* | 4/2002 | Flendrig | ............... | C12M 25/02 |
| | | | | | 435/395 |
| 7,862,718 | B2 | 1/2011 | Doyen et al. | | |
| 8,367,370 | B2 | 2/2013 | Wheeler et al. | | |
| 8,393,477 | B2 | 3/2013 | Kamleiter et al. | | |
| 9,284,531 | B2 | 3/2016 | Stachelscheid | | |
| 2001/0042716 | A1 | 11/2001 | Iversen | | |
| 2005/0003530 | A1 | 1/2005 | Gerlach | | |
| 2005/0142530 | A1 | 6/2005 | Galavotti | | |
| 2011/0124078 | A1* | 5/2011 | Edwards | ............... | C12M 29/16 |
| | | | | | 435/243 |
| 2011/0159584 | A1 | 6/2011 | Gibbons | | |
| 2012/0132813 | A1 | 5/2012 | Baumfalk et al. | | |
| 2012/0149091 | A1 | 6/2012 | Wilkerson et al. | | |
| 2015/0017683 | A1 | 1/2015 | Abdulla | | |
| 2016/0095969 | A1 | 4/2016 | Maurer et al. | | |
| 2016/0151535 | A1 | 6/2016 | Hoare et al. | | |
| 2016/0319234 | A1 | 11/2016 | Song et al. | | |
| 2018/0127705 | A1 | 5/2018 | Langenfeld et al. | | |
| 2019/0345433 | A1 | 11/2019 | Prabhudharwadkar et al. | | |
| 2021/0238527 | A1* | 8/2021 | Kilpatrick | ............ | B01D 63/026 |

FOREIGN PATENT DOCUMENTS

| | | | |
|---|---|---|---|
| EP | 0387975 | A1 | 9/1990 |
| EP | 0419234 | A2 | 3/1991 |
| EP | 2574664 | A1 | 4/2013 |
| GB | 2477140 | A | 7/2011 |
| JP | 2005333945 | A | 12/2005 |
| WO | 2005108549 | A1 | 11/2005 |
| WO | 2008141935 | A1 | 11/2008 |
| WO | 2010069319 | A2 | 6/2010 |
| WO | 2014034146 | A1 | 3/2014 |
| WO | 2020069607 | A1 | 4/2020 |

OTHER PUBLICATIONS

Housler, Greggory J., et al., "Compartmental Hollow Fiber Capillary Membrane-Based Bioreactor Technology for In Vitro Studies on Red Blood Cell Lineage Direction of Hematopoietic Stem Cells", Tissue Engineering: Part C, vol. 18, No. 2, 2012. pp. 133-142.
De Bartolo, Loredana et al., "Human hepatocyte functions in a crossed hollow fiber membrane bioreactor", Biomaterials 30 (2009) pp. 2531-2543.
Zhuang, Meiling et al., "Thermo-responsive poly(N-isopropylacrylamide)-grafted hollow fiber membranes for osteoblasts culture and non-invasive harvest", Materials Science and Engineering: C, vol. 55 (2015) pp. 410-419.
Ying, Lei et al., "Synthesis and Characterization of Poly(N-isopropylacrylamide)-graft-Poly(vinylidene fluoride) Copolymers and Temperature-Sensitive Membranes", Langmuir, 2002, 18 (16), pp. 6416-6423.
International Patent Application No. PCT/CA2019/051397, International Search Report and Written Opinion, dated Dec. 18, 2019.
International Patent Application No. PCT/CA2019/051397, International Preliminary Report on Patentability, dated Mar. 23, 2021.
Eghbali, Hadis et al., "Hollow fiber bioreactor technology for tissue engineering applications", International Journal of Artificial Organs, vol. 39, No. 1, Feb. 22, 2016, pp. 1-15.
Haigh, Jodie Nicole, "Melt Electrospinning Writing as a Method to Form Novel Hydrogel Architectures and Constructs", Masters of Science; Chemistry, Physics and Mechanical Engeering (CPME) Science and Engineering Faculty Queensland University of Technology, 2017, https://eprints.qut.edu.au/103849/1/Jodie_Haigh_Thesis.pdf.
Tripathi, Anurodh et al., "Synthesis of organic aerogels with tailorable morphology and strength by controlled solvent swelling following Hansen solubility", Scientific Reports, Feb. 1, 2018, vol. 18, No. 1, pp. 1-12.
Babgobin, Ravi, "Bubble-free oxygen and carbon dioxide mass transfer in bioreactors using microporous membranes", Masters of Engineering Science; The School of Graduate and Postdoctoral Studies, The University of Western Ontario, London, Ontario, Canada, Apr. 17, 2012, pp. 1-141, https://ir.lib.uwo.ca/etd/438/pdf.
Lo, Justin H. et al., "Gas Transfer in Cellularized Collagen-Membrane Gas Exchange Devices", Tissue Engineering, Part A, vol. 21, No. 15-16, 2015, pp. 2147-2155.
International Patent Application No. PCT/CA2021/050124, International Search Report and Written Opinion, dated May 20, 2021.
International Patent Application No. PCT/CA2021/050124, International Preliminary Report on Patentability, dated Jul. 28, 2022.
U.S. Appl. No. 17/168,085, Office Action dated Nov. 6, 2024.
U.S. Appl. No. 17/168,085, Final Office Action dated Apr. 17, 2024.
U.S. Appl. No. 17/168,085, Final Office Action dated Aug. 2, 2023.
U.S. Appl. No. 17/168,085, Final Office Action dated Apr. 18, 2023.
U.S. Appl. No. 17/280,727, Final Office Action dated Oct. 21, 2024.
U.S. Appl. No. 17/280,727, Office Action dated Mar. 25, 2024.
European Patent Application No. 21750383.8, Extended European Search Report dated Nov. 13, 2024.
U.S. Appl. No. 17/214,421, Office Action dated Mar. 1, 2024.
U.S. Appl. No. 17/214,421, Office Action dated Jun. 6, 2024.
European Patent Application No. 21750383.8, Partial Supplementary European Search Report dated Apr. 10, 2024.
Canadian Patent Application No. 3,167,379, Office Action dated Sep. 13, 2024.
Schmelzer, E. et al., "Effect of Human Patient Plasma Ex Vivo Treatment of Gene Expression and Progenitor Cell Activation of Primary Human Liver Cells in Multi-Compartment 3D Perfusion Bioreactors for Extra-Corporeal Liver Support", Biotechnology and Bioengineering, vol. 103, No. 4, Jul. 1, 2009, pp. 817-827.
Monga, S. et al., "Human fetal hepatocyte behavior in dynamic 3D perfusion culture bioreactors", Journal of Organ Dysfunction, 2007; 3: 183-192.
Gerlach, J. et al., "Bioreactor for a Larger Scale Hepatocyte In Vitro Perfusion", Transplantation, vol. 58, 984-988, No. 9, Nov. 15, 1994.
U.S. Appl. No. 17/214,421, Office Action dated Dec. 4, 2024.
Canadian Patent Application No. 3,167,379, Office Action dated Aug. 4, 2023.
Canadian Patent Application No. 3,167,379, Office Action dated Aug. 25, 2025.
U.S. Appl. No. 17/168,085, Office Action dated May 6, 2025.
U.S. Appl. No. 17/168,085, Office Action dated Oct. 27, 2025.
"Mold." Merriam-Webster.com Dictionary, Merriam-Webster, https://merriam-webster.com/dictionary/mold. Accessed Apr. 26, 2025. (Year: 2025).
U.S. Appl. No. 17/280,727, Office Action dated Mar. 13, 2025.
U.S. Appl. No. 17/280,727, Notice of Allowance dated Jul. 29, 2025.

(56)          References Cited

OTHER PUBLICATIONS

U.S. Appl. No. 17/214,421, Notice of Allowance dated Mar. 19, 2025.

* cited by examiner

CELL CULTURE BIOREACTOR WITH ZONE CONTROL

RELATED APPLICATIONS

This specification is a National Stage Entry of International Application No. PCT/CA2021/050124, filed Feb. 4, 2021, which claims priority to, and the benefit of, U.S. Provisional Patent Application No. 62/970,305, Cell Culture Bioreactor With Zone Control, filed on Feb. 5, 2020, and U.S. Provisional Patent Application No. 63/002,504, Cell Culture Bioreactor For Suspension Culture, filed on Mar. 31, 2020, both of which are incorporated by reference.

FIELD

This specification relates to cell culture and cell culture bioreactors.

BACKGROUND

The following is not an admission that anything discussed below is common general knowledge or citable as prior art.

The term "cell culture" is sometimes used to refer to the culture of any cells and sometimes specifically to the culture of eukaryotes. In this specification, unless stated otherwise, cell culture includes the culture of any cells including a) eukaryotes, for example animal cells such as mammalian cells, b) non-eukaryotes such as bacteria or eukaryotic organisms such as yeasts, fungi or protozoa (sometimes referred to as "microbial culture") and c) plant cells (sometimes referred to as "plant cell culture" or "tissue plant cell culture"). Further, cell culture as used in this specification, unless stated otherwise, includes growing cells for the purpose of obtaining the cells themselves and growing cells for the purpose of obtaining a product produced by the cells, for example a genetic material, protein, peptide or enzyme. This is in contrast to growing cells primarily for the purpose of consuming a pollutant as in wastewater treatment.

In some cell culture bioreactors, a nutrient medium flows through the lumens of hollow fiber membranes to provide a perfusion culture mode wherein nutrients diffuse through pores of the membranes to cells growing in the outside of the membranes, optionally called the extra-capillary space (ECS).

INTRODUCTION

The following introduction is not intended to limit or define the claims.

This specification describes a cell culture bioreactor having a plurality of zones. Each of the zones has one or more membranes. Some of the membranes may be perfusion membranes carrying a liquid media. The liquid media may be used to supply and/or remove liquid, dissolved or dispersed (i.e. solid) compounds. Some of the membranes may be gas transfer membranes carrying a gaseous media. The gaseous media may be used to supply and/or remove one or more gasses, which may include vapors. Optionally, some zones may intersect with other zones to form compound zones. For example, a zone of perfusion membranes may intersect a zone of gas transfer membranes.

The specification also describes a bioreactor having one or more sensors configured to collect data from one or more locations within the bioreactor. In some examples, data is collected from an array of locations. In some examples, data is collected through transparent parts or windows of the bioreactor. In some examples, the cell culture bioreactor also has a plurality of zones as described above. The data collection locations can be associated with, or mapped to, the zones.

This specification also describes a fluid control module. The fluid control module connects one or more ports to a plurality of control areas. The fluid control module has valves or other flow control devices that allow the flow of a fluid stream between a port and a selected control area to be varied. The variation may be relative to a flow provided at a different time and/or relative to a flow rate provided to a different area. In some examples, a control area is connected to two or more ports of a fluid control module. Optionally, the connection between a control area and one of multiple ports may be uncontrolled. Optionally the flow to or from a port may be controlled externally to the fluid control module. In some examples, one or more fluid control modules are combined with a bioreactor having a plurality of zones as described above. One or more outlet areas of one or more fluid control modules may be associated with one or more zones of the bioreactor.

This specification also describes a process for operating a bioreactor. The process includes controlling the supply of one or more gaseous and/or a liquid media to zones of a bioreactor. In some examples, data associated with the zones is collected. The data may be considered in determining a flow of gas or liquid media to be provided to one or more zones of the bioreactor. In some examples, the determinations may be made according to an algorithm or other programmed or automated control process. Optionally, the process may involve multiple bioreactors in a multi-stage process. The process may be, for example, a batch, fed-batch or continuous process. The process may be used to grow various cell types to produce a cellular or whole cell product.

In some examples of a cell culture process, first media is provided in a portion of the ECS of the reactor, and later first media is provided in a larger portion of the ECS of the reactor. Gas and/or second media is supplied to elements of the reactor while they are immersed in first media.

This specification also describes a system. The system includes a bioreactor with a plurality of zones, one or more sensors, one or more fluid control devices and a controller. One or more of the bioreactor, sensors and fluid control devices may be as described above. The controller may be a computer, for example a general purpose computer or a programmable logic controller.

This specification also describes a method and bioreactor for growing cells in suspension, in aggregates within a membrane matrix, adhering to a membrane, or simultaneously in a combination of these modes. The apparatus includes hollow fiber membranes. Liquid media circulates within an extra-capillary space of the bioreactor. The circulation may be provided by, for example, a mixer, forced flow of liquid through the extra-capillary space, or movement of the bioreactor, for example by rotating the bioreactor. One or more of the membrane diameter, membrane spacing, membrane packing density, the arrangement of the membrane into zones, the slack or taut mounting of the membranes, or the orientation of the membranes may be selected to assist in the circulation. In some examples of a process, a portion of the cells in a bioreactor is permitted for a period of time to be restrained within one or more zones of the membranes.

This specification also describes a bioreactor and a method of making a bioreactor. An interim construct of the bioreactor may have a mold and membrane plate assemblies mounted in the mold. The hollow fiber membranes may be regularly spaced apart in the membrane plate assemblies.

The mold and the membrane plate assemblies may have cooperating features that locate the membrane plate assemblies within the mold. The mold may have apertures in surfaces of the mold generally parallel with the membranes and/or panels in surfaces of the mold generally perpendicular to the membranes. The panels may separate potting cavities defined by the mold. In a further construct, solidified potting material seals the ends of the membranes in one or more potting cavities. In a further construct, portions of the potting material and mold are removed to expose the lumens of the membranes at the ends of the membranes. Caps may be placed over the ends of the membranes providing one or more ports in communication with the lumens of the membranes. An aperture of one construct as described may be connected to the aperture of another such construct, to a top plate, to a base plate, to a mixing layer or to a harvest layer.

In a process, one or more membrane plate assemblies are placed and located in a first part of a mold. A second part of the mold is added to enclose potting cavities around ends of the membrane plate assemblies. A liquid potting resin is added to the potting cavities and cured. A portion of the mold and potting material is removed to expose the lumens of the membranes. The exposed lumens of the membranes may be connected to a gas supply system or to a liquid media supply system. The mold may have apertures in surfaces of the mold generally parallel with the membranes and/or panels in surfaces of the mold generally perpendicular to the membranes, which remain with a resulting element when the portion of the mold and potting material are removed. The apertures of an element may be connected to a top plate, a base plate, another element, a mixing layer or a harvest layer to provide a bioreactor of a selected configuration.

BRIEF DESCRIPTION OF THE FIGURES

FIGS. 11A, 11B, and 110 show growth, harvest and mixing layers of a bioreactor with sensors in the layers.

DETAILED DESCRIPTION

PCT application number PCT/CA2019/051397, called Cell Culture Bioreactor and filed on Sep. 30, 2019, describes a cell culture bioreactor and methods of making it. This application is incorporated herein by reference. Various elements of the bioreactor described herein may be made according to the description in PCT application number PCT/CA2019/051397. One or more of the inventions described herein may also be adapted to other bioreactors described in PCT application number PCT/CA2019/051397 or other types of bioreactors known in the art.

Figure 1:
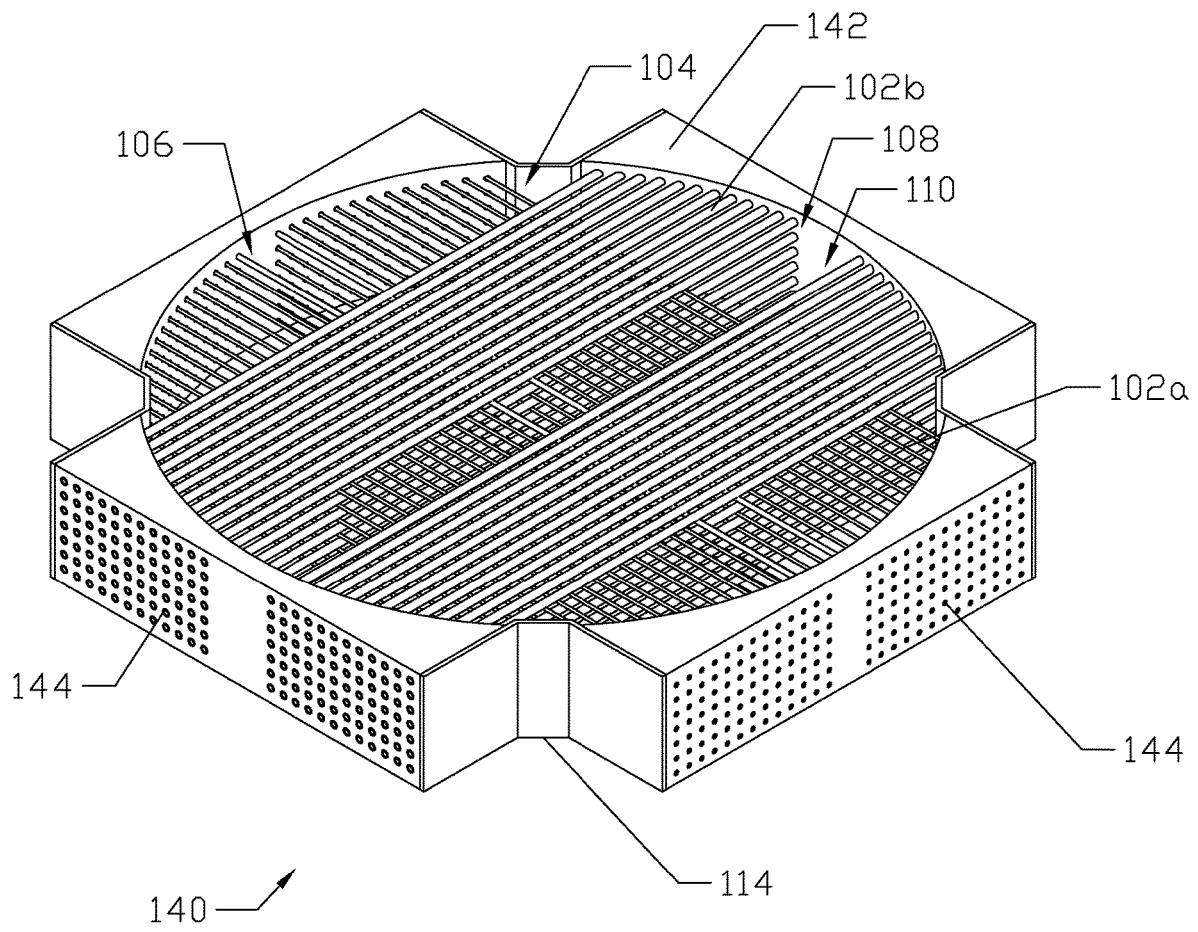
FIG. 1 shows an isometric view of a segment of a bioreactor.

FIG. 1 shows an element 140, optionally called a module, having membranes 102. In the example shown, the membranes 102 are hollow fiber membranes, but other types of membranes may be used. The membranes 102 may be divided into multiple sets of membranes. In the example shown, the membranes 102 include membranes oriented in two directions. In other examples, membranes 102 may be oriented in more or less directions. In the example shown, there are also two types of membranes, perfusion membranes 102a and gas transfer membranes 102b. In other examples, an element may have, for example, only perfusion membranes 102a, only gas transfer membranes 102b, a mixture of different perfusion membranes 102a or a mixture of different gas transfer membranes 102b. In the example shown, the perfusion membranes 102a are perpendicular to the gas transfer membranes 102b.

The membranes 102 are potted in potting heads 142, alternatively called potting blocks. The potting heads 142 are optionally made of an epoxy or polyurethane resin, optionally cast in place around ends of the membranes 102 as the membranes 102 are rotated within a mold. Lumens 144 of the membranes 102 are open to a face of at least one potting head 142. For example, a radially outward portion of each potting head 142 may be cut away to expose the lumens 144 at open ends of the membranes 102. Portions of braces 114 that were inserted in the mold may be cut away with parts of the potting heads 142, but parts of the braces 114 remain to connect remaining parts of the potting heads 142 together. The braces 114 may be transparent.

Optionally, lumens 144 of the membranes 102 are open at both ends to faces of two potting heads 142. Optionally, the membranes 102 potted into a particular potting head 142 may be separated into zones. Zones may be separated from each other vertically, horizontally, or in other directions. In the example shown, the perfusion membranes 102a are divided horizontally (i.e. separated by a vertical line) into two zones, 104 and 106. The gas transfer membranes 102b are also divided into two zones 108 and 110. The intersection of these zones produces four compound zones within the element 140, in particular zones 104/108; 104/110; 106/108; and, 106/110. In another example, the membranes 102a and/or 102b might also be divided vertically (i.e. separated by a horizontal line) to produce a two by two grid of four zones for each type of membrane 102a and 102b. The intersections of these zones would produce eight zones within the element 140. Other examples may have other vertical and/or horizontal divisions producing more or less zones.

Figures 2, 3, 4:
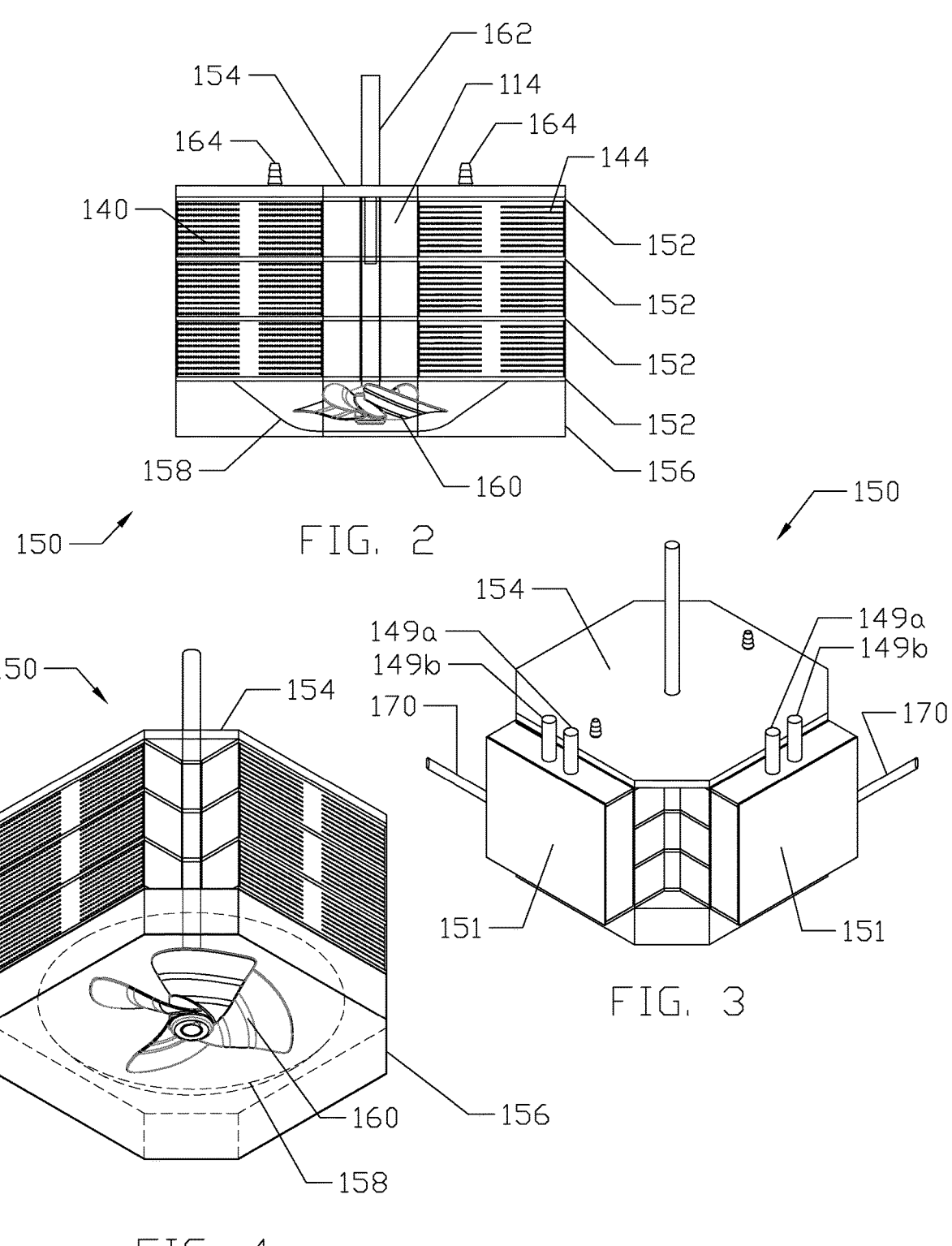
FIG. 2 shows a side view of a bioreactor including three of the segments of FIG. 1.
FIG. 3 is a top isometric view of the bioreactor of FIG. 2 having fluid control modules.
FIG. 4 is a bottom isometric view of the bioreactor of FIG. 2 with the fluid control modules removed.

FIG. 2 shows a quarter side view of parts of reactor 150 made with multiple elements 140. In the example shown, the reactor 150 has three elements 140. However, an alternative reactor 150 might have one, two, or more than three elements 140. The extra-capillary spaces (the spaces inside of the potting heads 142 but outside of the membranes 102; alternatively called the ECS) of the elements 140 are in liquid communication with each other and collectively form one continuous plenum inside the reactor 150. The number of elements 140 may be sufficient so that the height of the plenum is 50% or more, 100% or more or 200% or more of the (average) length of the hollow fiber membranes 102a and/or 102b. Alternatively, the ECS of the elements 140 may be separated from each other to form multiple distinct reactors connected in parallel with shared perfusion media and gas transfer systems. Parallel reactors may be used, for example, for autologous cell therapy manufacturing.

The reactor 150 also includes a top 154 and a base 156. The elements 140 can be sealed together and to the top 154 and the base 156 by an adhesive or through gaskets 152. If gaskets 152 are used, they may be compressed by placing the reactor 150 in a frame (not shown) or placing bolts through the reactor 150. The base 156 contains a well 158 with a mixer 160, shown also in FIG. 4. The mixer 160 is optionally driven by a shaft 162, which extends upwards through the reactor 150 and out through the top 154. In other alternatives, a mixer 160 is driven by a mechanical, hydraulic or pneumatic linkage; by an immersed electric motor; or, by magnetic force through a wall of the bioreactor 150. In other alternatives mixing is provided by fluid circulation (i.e.

flowing media into and out of the ECS). In other alternatives a shaft 162 supports multiple mixers 160. The mixer 160 can be used to re-suspend cells that have settled in the well 158, if necessary, or to mix growth media in the plenum. The top 154 includes one or more fittings 164 that can be used, for example, to add growth media or a component of a growth media to the plenum, to hold a sensor, for sampling, to remove growth media from the plenum, to drain the reactor 150, to harvest cells or cell products, or to vent a gas from the reactor 150. Optionally, the reactor 150 may be mixed by moving, for example rotating, the entire reactor 150. In addition to mixing media in the ECS and optionally suspending cells, mixing the reactor 150 disturbs boundary layers around the membranes 102 and helps to homogenize transfer through membrane surfaces in different parts of the reactor 150.

FIGS. 2 and 4 show the lumens 144 of the hollow fiber membranes 102 exposed. However, in use, the ends of the membranes 102, and their lumens 144, are covered, for examples with caps, headers, manifolds or with flow control modules 151 as shown in FIG. 3. A cap, header, manifold or flow control module 151 is optionally connected to the sides of one or more elements 140 or to sides of the reactor 150 as a whole. The caps, headers, manifolds and/or flow control modules 151 allow fluids to flow into and out of the membranes 102. The membranes 102 provide liquid media perfusion or gas perfusion while retaining cells in the ECS. Optionally the pore size or skin of the membranes also retains selected media components or cell culture products in the ECS. Optionally, the gas or liquid flowing through the membranes may be used to heat or cool the ECS.

The bioreactor 150 has a set of fluid control modules 151. In the example shown, a fluid control module 151 covers one side of each of three elements 140, which make up one side of the bioreactor 150. In other examples, a fluid control module 151 may cover more or less elements 140. Optionally, multiple fluid control modules 151 may be placed on a side of a bioreactor 150. In the example shown, a fluid control module 151 is placed on each of two sides of the bioreactor 150, in communication with one end of each type of membrane 102a, 102b. In other examples, the bioreactor 150 may have fluid control modules 151 on more or less of its sides or on different sides. For example, fluid control modules 151 may be associated with only one set of membranes 102a, 102b. In other alternatives, fluid control modules 151 may be placed on both ends of either or both sets of membranes 102a, 102b.

In the example shown, a fluid control module 151 has two ports 149a, and 149b. In other examples a fluid control module 151 may have more or less ports 149. A fluid control module 151 also has a control conduit 170. In the example shown, the control conduit 170 is a bundle of electrically conductive wires. In other examples, the control conduit may contain one or more wires, fiber optic cables, pneumatic tubes, hydraulic tubes or other conduits capable of carrying a signal. In other examples the control conduit 170 is replaced by an electromagnetic receiver, such as a Bluetooth receiver. In some examples, the fluid control module 151 may also be connected to a power supply, for example an electrical power supply.

In the example shown, the bioreactor 150 has twelve compound zones. The four compound zones within each element 140, i.e. zones 104/108; 104/110; 106/108; and, 106/110, are repeated in each of the three elements 140. On each side of the bioreactor 150, the lumens 144 of six sets of membranes 102, one set on the left side and one set on the right side of each of three elements 140, are accessible. In other examples the bioreactor 150 may have more or less zones and more or less sets of membranes 102 accessible from any particular side of the bioreactor 150. For example, a bioreactor 150 may have more or less than three elements 140. Alternatively or additionally, an element 140 may have more or less than four zones or more or less than four compound zones.

Figures 5, 6:
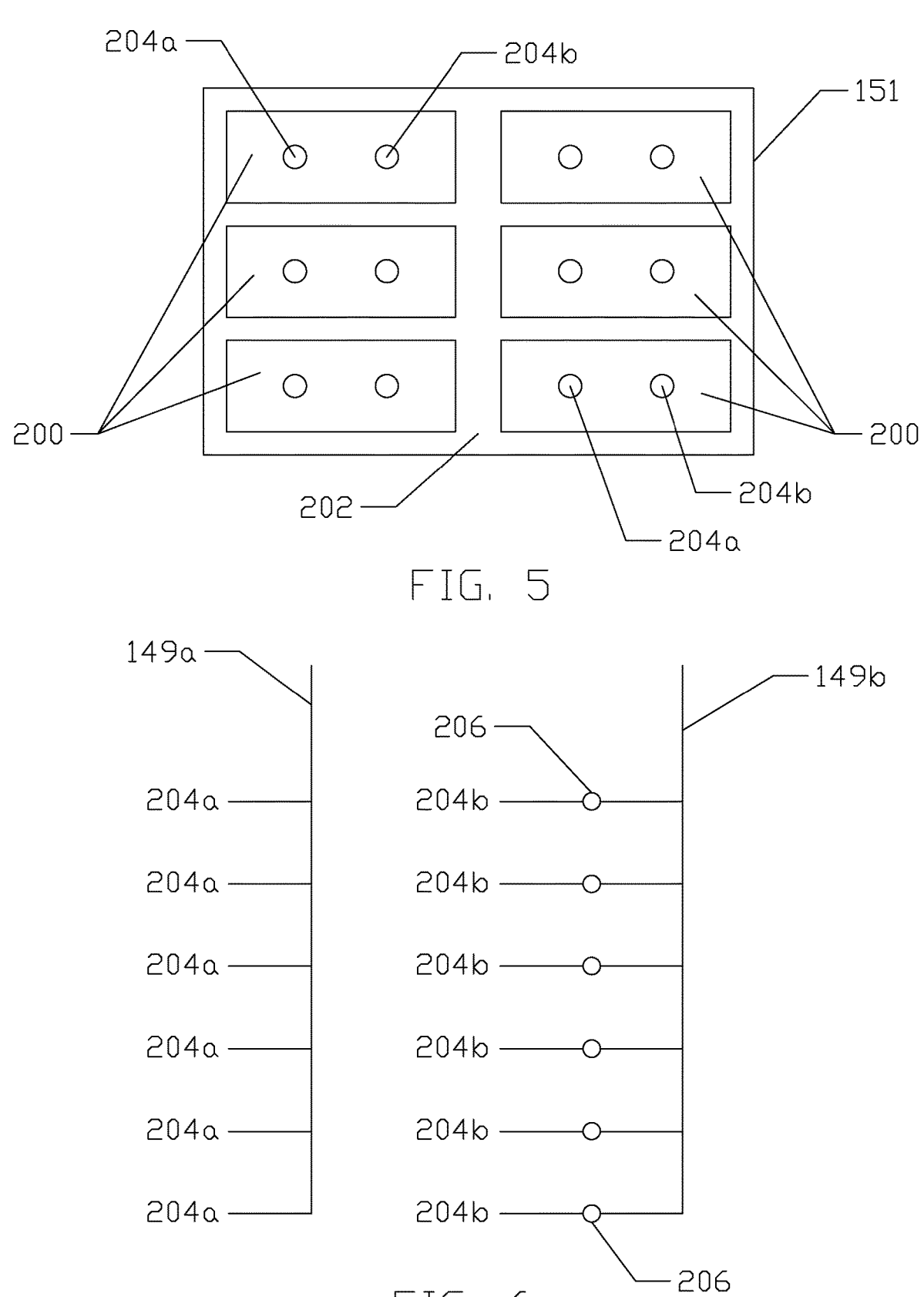
FIG. 5 shows one side a fluid control module of FIG. 4.
FIG. 6 shows flow paths inside a fluid control module of FIG. 4.

FIG. 5 shows a side of the fluid control module 151 that is placed against the bioreactor 150. This side of the fluid control module 151 has multiple control areas 200. Each control area 200 corresponds with an area on the side of the bioreactor 150 having accessible lumens 144 of a set of membrane 102. The set of membranes 102 may correspond with a zone, for example one or more of zones 104, 108, 106 and 110 on one or more of the elements 140. In the example shown, the fluid control module 151 has six control areas 200. When the fluid control module 151 is attached to a side of the bioreactor 150, the six control areas 200 are in communication with six zones of the bioreactor 150, for example zones 104 and 106 or zones 108 and 110 of each of three elements 140. Optionally, a control area gasket 202 may be used to separate the control areas 200 from each other and to provide a seal between a control area 200 and a set of lumens 144.

Each control zone 200 has one or more openings 204. The openings 204 are fluidly connected to the ports 149. FIG. 6 shows an example of connections within the fluid control module 151. In the example shown the six openings 204a are connected to port 149a. The six openings 204b are each connected through a valve 206 to port 149b. Each valve 206 can be open or closed. Optionally, a valve 206 may be infinitely variable or have one or more intermediate positions between open and closed. However, in some examples sufficient control is achieved by valves 206 having only two positions, for example open and closed. Other arrangements of valves 206 may be used. The valves 206 may be activated, for example, by solenoids, pneumatics, hydraulics or other means known in the art of fluidic or microfluidic chips or controllers. Signals and/or power to open and close the valves 206 are provided through the control conduit 170. The control conduit 170 is connected to a controller, which may include a computer.

The flow through a zone 104, 106, 108, 110 may be controlled by a fluid control module 151 on the upstream end, downstream end, or the both upstream and downstream ends of a zone 104, 106, 108, 110. If a fluid control module 151 is provided only on one side of a zone 104, 106, 108, 110, then the other side of the zone 104, 106, 108, 110 may be covered with a cap, manifold or header connected to an inlet or outlet port.

Figure 7:
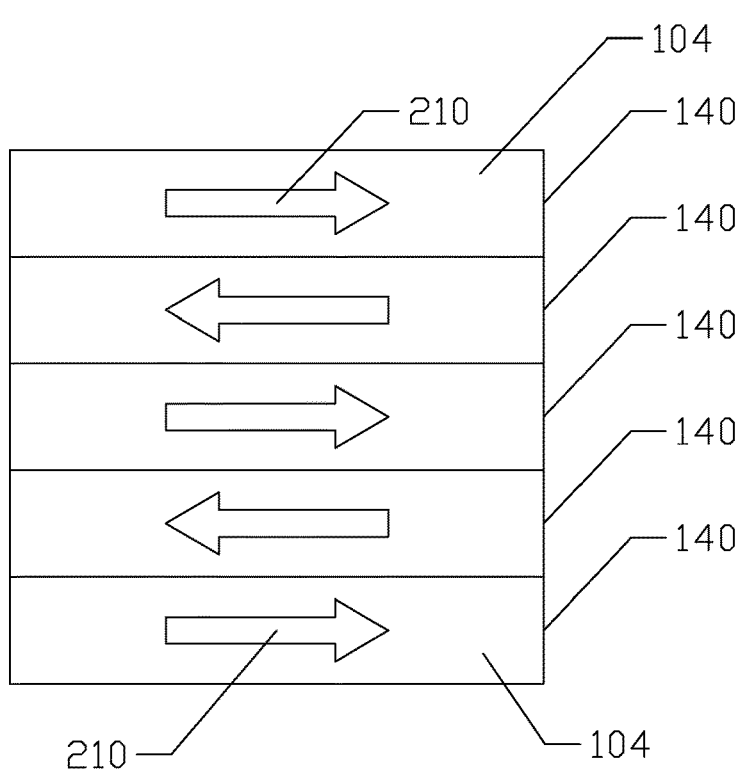
FIG. 7 shows flow direction reversal between adjacent elements of a bioreactor.

A fluid control module 151 may alternatively have ports 149 connected to openings 204 in only some of the control areas 200. In this way, a fluid may flow into some control areas and out of other control areas. Accordingly, the flow in a zone 104, 106, 108, 110 of one element 140 may be in the same direction or the opposite direction compared to the corresponding zone 104, 106, 108, 110 in another element 140 of the bioreactor 150. For example, as shown in FIG. 7, the direction of flow 210 in a zone 104 (or any other zone) may alternate between successive elements 140.

Optionally, a fluid control module 151 may have heating elements or cooling elements. The heating or cooling elements may heat or cool the outside of the bioreactor 151 or a heat or cool a fluid entering the bioreactor. In some example, each control area 200 has a heater element. Optionally, the heating elements may be individually controlled. Heating or cooling a fluid entering the bioreactor may advantageously adjust the temperature throughout the ECS rather than only on the walls of the reactor 150.

Figure 8:
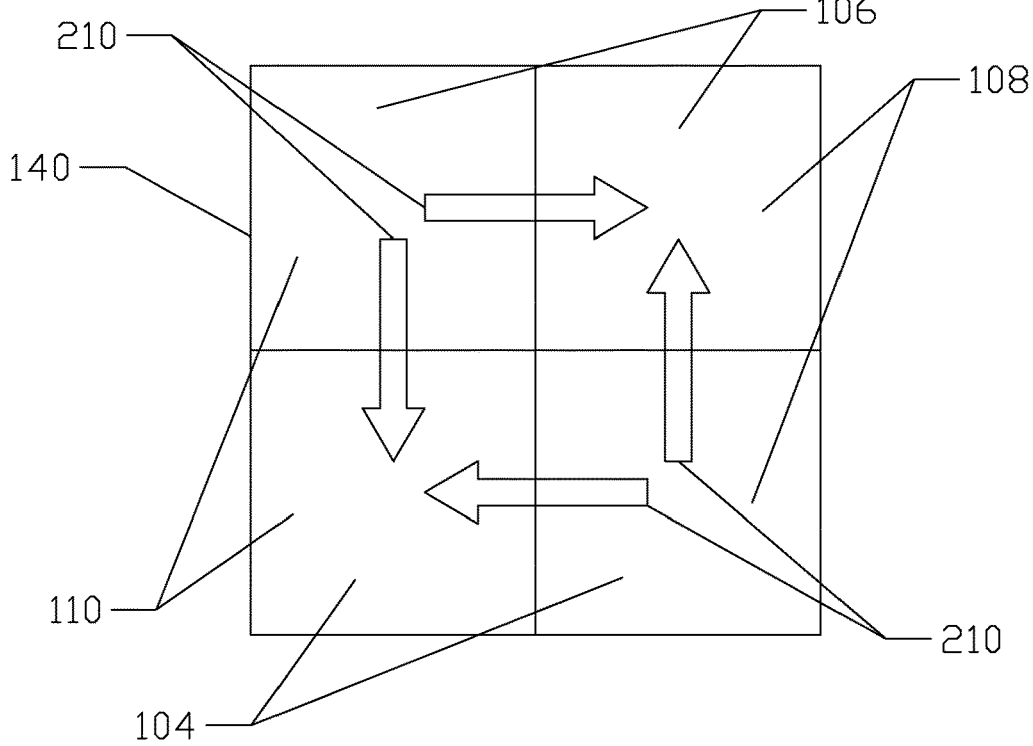
FIG. 8 shows flow direction reversal between adjacent zones within an element of a bioreactor.

Referring to FIG. 8, the direction of flow 210 may also alternate between adjacent zones within an element such as zones 108, 110 and/or zones 104, 106. A bioreactor 150 may have flow direction alternation both within elements 140 and/or between elements 140. In the example of FIG. 8, zones 104 and 106 are nutrient delivery zones and zones 108 and 110 are oxygen delivery zones. Since the concentration of nutrients and oxygen supplied from within the membranes 102 decreases along the length of the membranes, two quadrants of the element 140 receive more nutrients and oxygen and two quadrants receive less nutrients and oxygen. The supply of nutrients and oxygen is therefore more nearly balanced in each quadrant. Further, each quadrant is smaller than the entire element 140 and has two sides connecting to a quadrant having different supply conditions, which reduces the amount of mixing required to homogenize conditions in the extra-capillary space of the bioreactor 150. Altering all of the flow directions in successive elements 140 as in FIG. 7, alone or in combination with flow reversal as in FIG. 8, also helps to homogenize conditions in the extra-capillary space of the bioreactor 150.

Figures 9, 10:
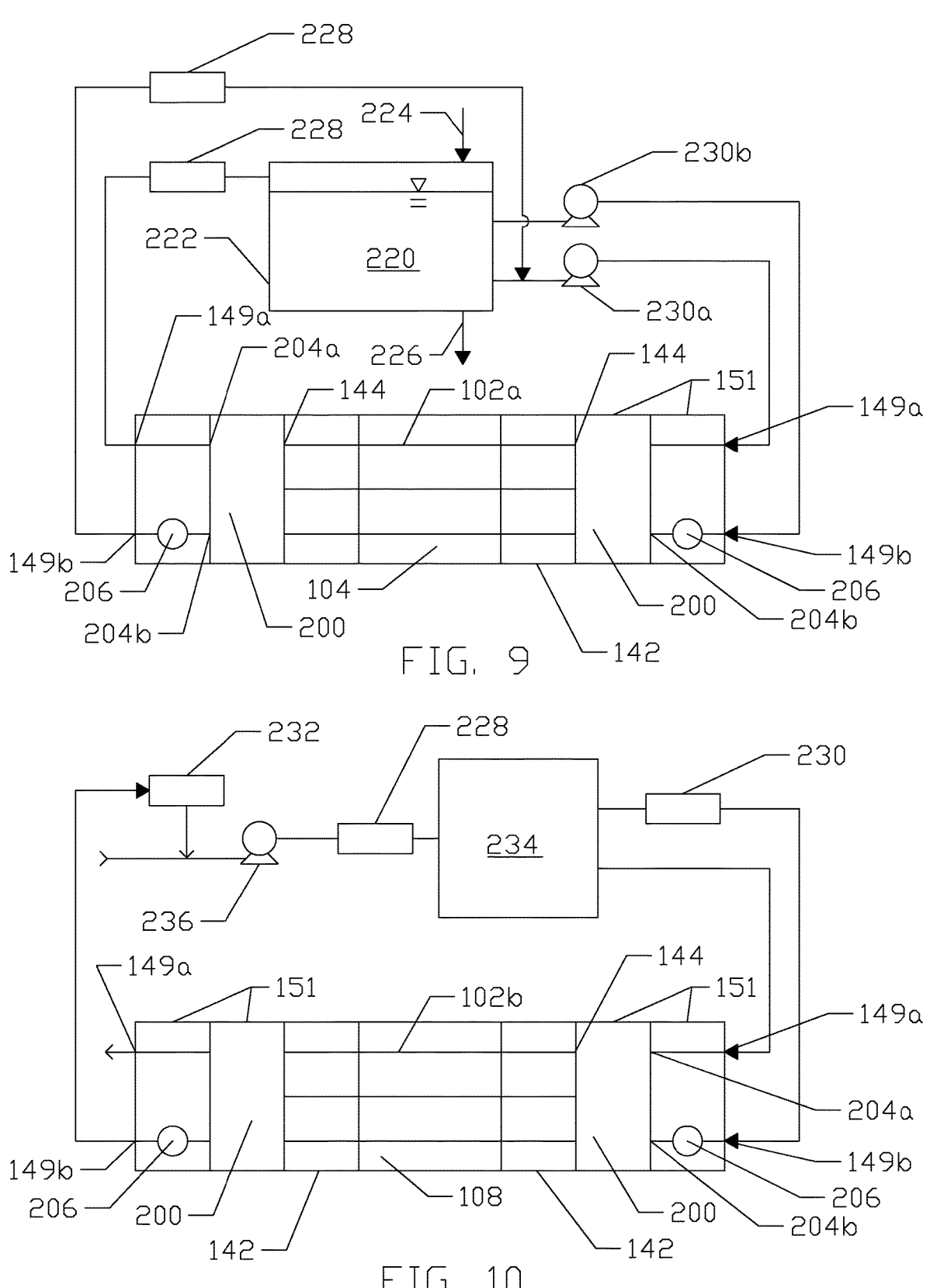
FIG. 9 shows various flow paths through a perfusion zone.
FIG. 10 shows various flow paths through a gas transfer zone.

FIG. 9 shows a fluid supply system for a perfusion zone 104, i.e. a zone having membranes 102 that carry a liquid media through their lumens 144. The liquid media 220 is recirculated between the zone 104 and a container 222 outside of the bioreactor 150. Optionally, fresh media 224 may be added to the container 222 and used media 226 may be withdrawn from the container 222 to replenish nutrients in the container 222 or remove contaminants or inhibitory compounds from the container 222. Adding fresh media to the container 222 and removing old media provides a media refresh rate for the inner-capillary space (ICS). Optionally, media 220 may be treated, for example in one or more treatment units 228, as it recirculates. A treatment unit 228 may be, for example: a heater, a cooler, a filter, a chemical dosing device, a mixing device, a gas supply device or a degassing device. Optionally, sensors may be added in media or gas carrying tubes upstream of downstream of the reactor 150. Optionally, growth factors (or other compounds retained in the ECS by the membranes) may be refreshed by adding them directly to the ECS.

One or more pumps 230 are connected to the container 222 to pump the liquid media 220. A pump 230 may be, for example, a peristaltic or other pump. A pump 230 may be connected to a variable frequency drive, inlet valve, outlet valve or other controllable device to allow the pressure and or flow at the outlet of the pump 230 to be controlled. Container 222 may be, optionally, an open tank or a sealed vessel. A pump 230 may be, optionally, upstream or downstream of the container 222. If a pump 230 is upstream of the container 222, the container 222 may be connected to the corresponding port 149 of the flow control module 151 by a conduit without a pump 230. The container 222 may be located above or below the zone 104. By manipulating these various options, the pressure inside of the membranes 102 may be above or below the pressure in the extra-capillary space of the zone 104 as required for the applicable cell growth process. The liquid media supply system for the reactor may be protected from contamination by having any connections to the atmosphere protected by vent filters. The membranes 102 themselves further protect the ECS from contamination. The reactor 150 and associated equipment are preferably sterilized before use, for example by steam (autoclave), gamma radiation, alcohol or other methods.

In the example shown, fluid control modules 151 are in communication with the upstream and downstream ends of the zone 104. Alternatively, only one fluid control module 151 may be used, in communication with either the upstream or downstream ends of the zone 104. Pump 230b produces a flow less than the flow produced by pump 230a. For example, pump 230b may produce 5-25% of the flow of pump 230a. Opening or closing valve 206 on the upstream side of the zone 104 thereby increases or decreases the flow of liquid media 220 through the zone 104.

Optionally, ports 149b are smaller than ports 149a. The port 149b on the downstream side of the zone 104 may be connected to the inlet of pump 230a as shown or alternately to the container 222 or the inlet side of pump 230b. Opening valve 206 downstream of the zone 104 may therefore do one or more of: increase the flow through zone 104, decrease the flow through zone 104, increase the pressure inside of membranes 102 or decrease the pressure inside of membranes 102. Four flow states are available depending on the positions of the two valves 206.

FIG. 10 shows a fluid supply system for a gas transfer zone 108, i.e. a zone having membranes 102 that carry a gaseous media through their lumens 144. A compressor 236 supplies air from the atmosphere though a treatment unit 228, for example a filter, to a pressure tank 234. The pressure tank 234 is connected to the ports 149 of the flow control device 151. The port 149b (in communication with valve 206) is connected to pressure tank 234 through a gas transfer membrane module 230. Gas transfer membrane module 230 may be configured to produce either oxygen enriched or oxygen depleted air. At the downstream end of the zone 108, the flow control module 151 has one port 149a vented to atmosphere and one port 149b connected to the inlet of compressor 236, optionally through a carbon dioxide stripper 232. By modulating the two valves 206, four different flow conditions may be obtained. Gas flowing in the lumens 144 of the membranes 102 in the gas transfer zone 108 may have an oxygen content above or below atmospheric and a pressure above or below atmospheric. Optionally, carbon dioxide concentration in the gas supplied to the gas transfer membranes 102b can be used to influence the ECS pH when combined with an appropriate buffer. Optionally, compressed gasses may be supplied to the reactor 150 in place of air from a compressor, optionally with a pressure break. All vents or intakes in the gas supply system are preferably covered with filters to avoid contamination. Optionally, the gas transfer membranes 102b may be used to provide a high rate of oxygen transfer while not producing a high dissolved oxygen concentration in the ECS. This may be particularly useful for growing cells, for example blood cells that require hypoxic conditions for rapid growth or to control differentiation.

Referring back to FIG. 1, the brace 114 is optionally transparent or has a transparent window. A transparent brace 114 may be used in combination with an optical sensor system. In one example, one or more sensor foils, for example by PreSens, may be placed inside the bioreactor 150, for example attached to the inside surface of the brace 114. The sensor foils are used in combination with a detector unit, for example a VisiSensTD™ modular mapping system, to produce a reading, for example of pH, dissolved oxygen concentration and/or dissolved carbon dioxide concentration. The sensor foil may be applied as a strip extending vertically along the braces 114 of one or more elements, or as a circle, square or other shape on a brace 114. To produce a reading, the detector unit excites one or more sensor foils with light (which may include UV or infra-red light) and records an image of the excited sensor foils. The detector unit may have a field of view that includes multiple sensor foils. The detector unit may be able to excite and record an image of one or more of each of multiple types of sensor foils (i.e pH, carbon dioxide concentration or oxygen concentration) simultaneously. The image is downloaded to a computer for analysis of the image, for example to determine one or more of a pH, oxygen concentration or carbon dioxide concentration value from one or more sensor foils or for one or more locations in the bioreactor 150. Optionally, a detector unit may traverse the height of a bioreactor 150 collecting readings from different elements 140, optionally including elements 140 spaced apart by a distance greater than the field of view of the detector unit. A traversing detector unit may be provided for each line of braces 114 of the bioreactor, for example for each of four lines of braces 114 in the four corners of the bioreactor 150. Optionally, the bioreactor 150 and/or the detector unit may move such that a detector unit may collect readings from multiple lines of braces 114. For example, one detector unit may sequentially collect readings from lines of braces 114 in the four corners of the bioreactor 150. Alternatively, the brace 114 may have a crystal insert, or be made of or include another light permeable material, allowing for other readings, for example by way of Raman spectrometry or electromagnetic spectroscopy such as near-infrared spectrophotometry, to made of the inside of the bioreactor 150. Raman spectrophotometry devices are available, for example, from Kaiser Optic Systems or Tornado Spectral Systems. In another alternative, the brace 114 has a hole or other fitting for a probe in contact with the inside of the bioreactor 150. Measurements may be taken from one, more than one, or all of the braces 114 of an element 140 and from every one or only some of the elements 140. Temperature may be measured at one or more points of the bioreactor 150, for example by way of probes inserted into the bioreactor 150, by measurements of the outer surface of the bioreactor 150, or by measuring the temperature of fluid leaving the extra-capillary space or the temperature of fluid leaving from any group of membranes 102.

Measurements of various parameters are made at various points in the bioreactor 150 at various times. The measurements are sent to a controller, for example a computer. The controller may be programmed with a digital model of the bioreactor 150. The controller may estimate the parameters at other points or times in the bioreactor. The controller may adjust the flow through one or more zones 104, 106, 108, 110 to correct conditions observed into the bioreactor 150 and/or to improve future conditions in the bioreactor 150.

In some examples, measurements are taken in a three-dimensional array. For example, measurements are taken at each of four braces 114 of each element 140. These measurements are exported to a computerized model of the bioreactor 150. The module may be analyzed to estimate one or more parameters at one or more positions within the bioreactor 150 that are not measurement locations. The model may also be analyzed to extract past trends, to predict future states and/or to predict the effect of changes in the pressure and/or flow of liquid and/or gaseous media to one or more zones of the bioreactor 150. The model may be combined with a controller programmed to make changes in the pressure and/or flow of liquid and/or gaseous media to one or more zones of the bioreactor 150 predicted to provide a desired condition within the bioreactor 150.

Figures 11A, 11B, 11C:
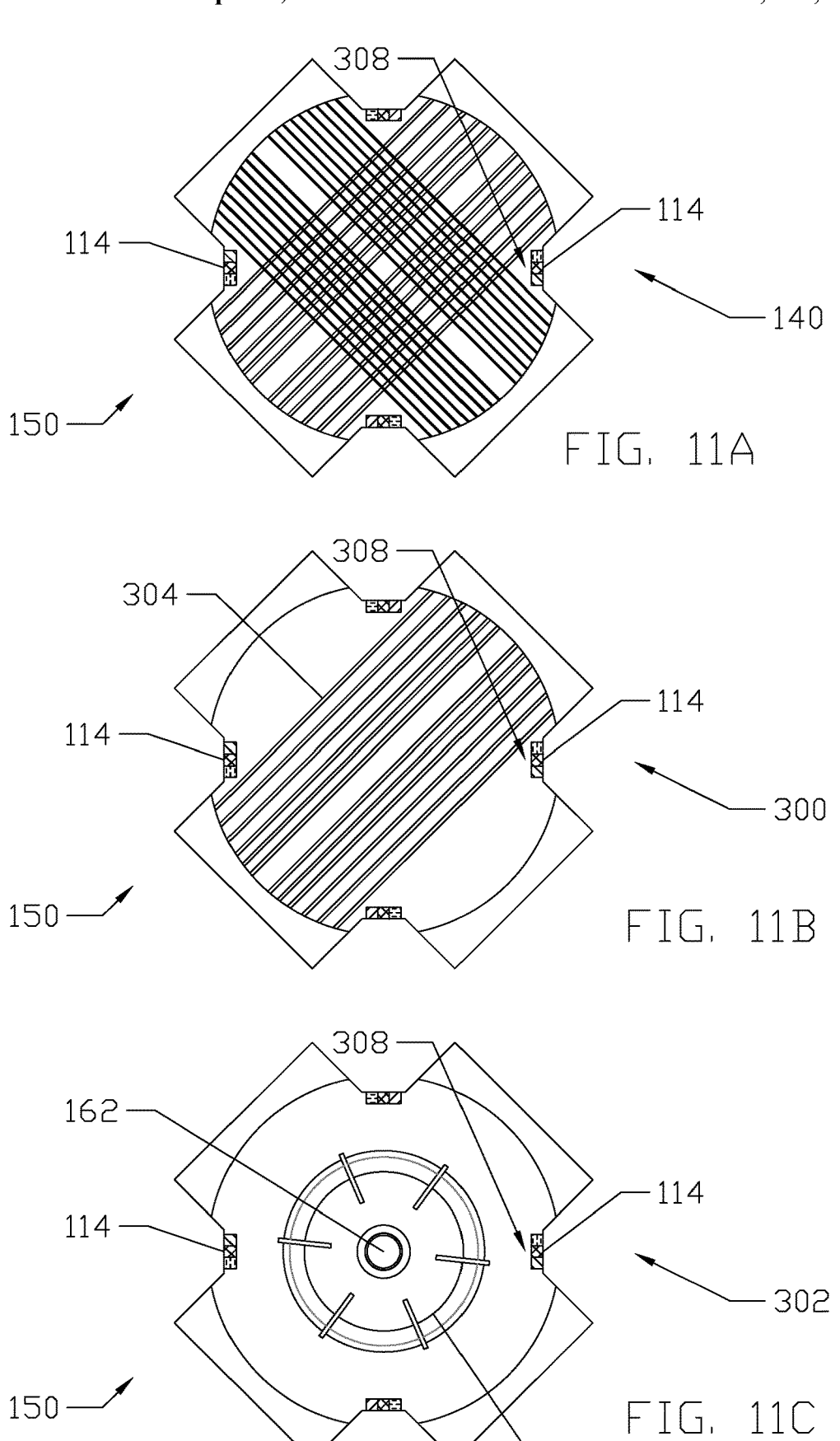

FIGS. 11A, 11B and 110 shows some optional layers of a bioreactor 150. FIG. 11A shows an element 140 as discussed previously, which may be called a growth layer. FIG. 11B shows a harvest layer 300. The harvest layer 300 can have a port (not shown) for removing cells or other products or materials from the bioreactor. Optionally the port may be in fluid communication with extraction membranes 304. The extraction membranes 304 can have pores large enough to remove nucleated progenitor red blood cells, which are about 8.5 to 10 microns (um) in diameter and 5 microns in width. Alternatively, the extraction membranes 304 can have pores that exclude nucleated progenitor red blood cells but remove enucleated reticulocytes, which are about 8.5 to 10 microns (um) in diameter and 2-3 microns in width. The enucleated reticulocytes are somewhat deformable and may pass through a pore smaller than their diameter. However, the nucleus has a diameter of about 5-6 microns and is less deformable. Accordingly, a generally round pore with a diameter of 3-5 microns may exclude nucleated progenitor red blood cells while passing enucleated reticulocytes. Other pore sizes may be used, for example, to remove virus, proteins or other cell culture products while leaving the cells in the ECS.

FIG. 11C shows a mixing layer 302. The mixing layer 302 has an impeller 306 that turns on a shaft 162 connected to the mixer 160 in the base 156 (not shown). However, unlike the base 156, the mixing layer 302 may be located between two elements 140, and allows liquids in the extra-capillary space (ECS) to pass vertically through it.

Some or all of the layers 140, 300, 302 have sensors. In the example shown, a set of sensor strips 308 extends vertically along the insides of the braces 114 of the layers 140, 300, 302. Each sensor strip 308 is an elongated section of an optical sensor foil as described above. The sensor strips 308 may include a dissolved carbon dioxide sensor, a dissolved oxygen sensor and a pH sensor. The sensor strips 308 give off a signal when interrogated with a detector unit through the braces 114, which are transparent. The detector unit may have, for example, a source of light of one or more peak wavelengths, a camera (i.e. CMOS or CCD) chip and optionally one or more optical filters. Optionally, the VisiSens TD™ modular mapping system from PreSens may be used as the detector unit. Optionally, different sensors are provided in different locations of the reactor.

Figures 12, 13:
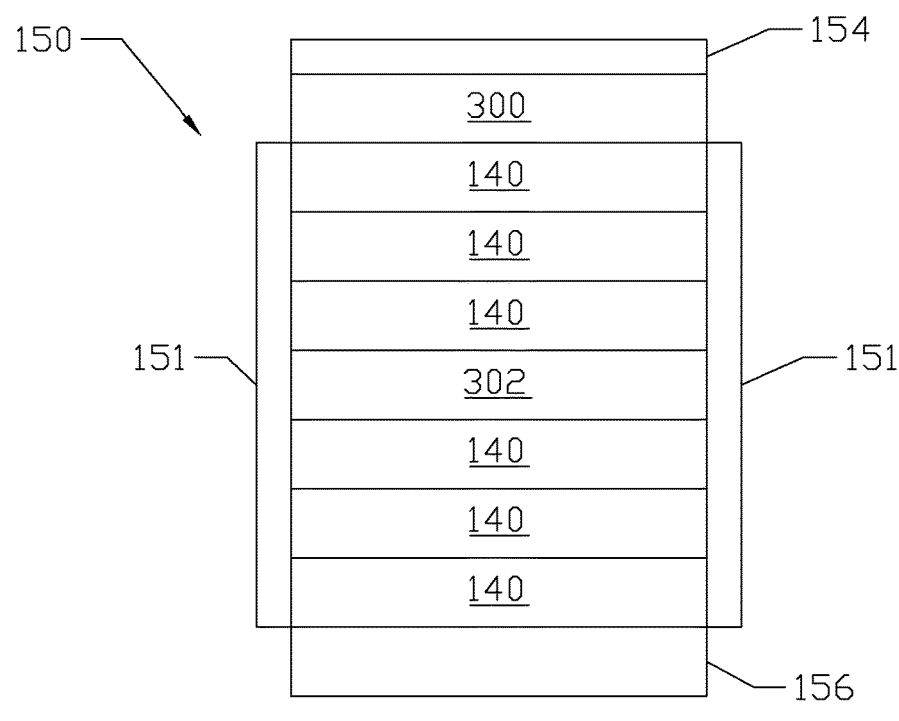
FIG. 12 shows a bioreactor having the layers of FIG. 11.
FIG. 13 shows a cell growth system.

FIG. 12 shows a bioreactor 150 having the layers 140, 300, 302 described above. Optionally, the bioreactor 150 may be assembled from sub-units having a plurality of elements 140 or a plurality of elements 140 and a base 156 or mixing layer 302. FIGS. 12 and 13 give examples of the arrangement of layers 140, 300, 302 in a bioreactor 150 but any other arrangement of layers 140, 300, 302 may be used.

The bioreactor 150 may be used, for example, to grow whole cell products or cellular therapeutic products. In some examples, the bioreactor 150 is used to grow red blood cells or red blood cell therapeutics. The term red blood cells (RBCs) will be used herein, unless the context indicates otherwise, to include RBCs and any of their precursors such as hematopoietic stem cells (i.e. CD34+ cells optionally obtained from bone marrow, peripheral blood or cord blood), a partially differentiated cell line derived from CD34+ cells, nucleated precursor cells or enucleated RBCs. A partially differentiated cell line may be grown, i.e. expanded, in a bioreactor 150. Optionally, partially differentiated cells may be converted into nucleated precursor cells and/or enucleated RBCs in a bioreactor 150. In other examples, one or more of steps of differentiation or enucleation occur outside of the bioreactor 150. The RBCs may be manufactured with fewer antigens belonging to clinically significant blood groups such as ABO, Rh, Kell, Duffy, Kidd, MNS, P1, etc. than typical red blood cells taken from a human donor, or with a specific combination of antigens. The manufactured RBCs may be suitable for inhibiting alloantibody formation (i.e. alloimmunization), which may be useful for repeat transfusion applications. The manufactured red blood cells may also be perceived by the patient to have a relatively young cell age, for example 20 days or less, compared to an average cell age of about 60 days for typical blood from a human donor, which may allow them to persist longer in vivo. The RBC manufacturing process can include expanding a population of stem cells or partially differentiated cells, transforming the stem cells or differentiated cells into RBCs, and enucleating the RBCs. The expansion of precursor cells and transformation of the red blood cells can be controlled by one or more genetic switches. Enucleation can be facilitated, for example, by filtering the nucleated RBCs through pores sized to require ejection of the nucleus to pass through.

FIG. 13 shows a system 310 having two bioreactors 150 and a purification cell 312, for example a filtration cell. A first bioreactor 150 is used to grow (i.e. expand) a population of cells, for example stem cells, immortalized erythroid progenitor cells and/or other precursors for RBC production. Compounds 165, for example growth factors, may be added to the ECS of the first bioreactor 150 or the second bioreactor 150 through a fitting 164. The expanded cell population is transferred from the first bioreactor 150 to the second bioreactor 150, optionally in batches or continuously. The second bioreactor 150 is used to further expand the population of cells, but under different conditions which cause the cells to differentiate and/or mature. In the case of RBCs, enucleation may be the final step of differentiation. Enucleation may be encouraged by a density gradient, a reagent such as phosphatidylserine, hemoglobin based cell removal, or forcing the cells through pores. The RBCs, optionally nucleated or enucleated or a mixture of nucleated and enucleated cells, may be transferred from the second bioreactor 150 to the purification cell 312, optionally in batches or continuously. The purification cell 312 is used to separate nucleated RBC precursor cells and previously ejected nuclei from enucleated RBCs/reticulocytes 506. The purification cell 312 may also be used to enucleate the RBCs, if they have not been previously enucleated, or for other finishing steps. Optionally, nucleated cells may be returned to the bioreactor 150.

In the bioreactor 150, cells, optionally in suspension alone or attached to carriers or attached to or retained by the membranes 102, receive nutrients through the perfusion membranes 102a and receive oxygen through the gas transfer membranes 102b. Optionally, soluble or dispersed waste products of the cells may be removed through the perfusion membranes 102a. A first media is added to the extra-capillary space of the bioreactor 150. Optionally, the first liquid media is circulated through the ECS. A second liquid media (i.e. liquid media 220 described above) is circulated through the lumens 144 of the perfusion membranes 102a. The second media may be the same as the first media or a different media. The first and/or second media may be a manufactured media, which may be derived from serum or not. The first and/or second media may have a reduced concentration of growth factors compared to conventional cell culture media. The first and/or second media may have one or more proteins replaced with small molecules and/or surfactants.

Optionally, carbon dioxide released by the cells is removed from the extra-capillary space of the bioreactor 150 through the gas transfer membranes 102b. To assist in the removal of carbon dioxide, the pressure inside of the gas transfer membranes 102b may be less than the static head pressure inside of the bioreactor 150 or less than atmospheric pressure. The gas transfer membranes 150 may have manufactured pores, for example of 30 Angstroms or less or 40 Angstroms or less in size, or may be dense walled. Optionally, at least at some times, oxygen enriched air is supplied through the gas transfer membranes 102a. This increases the partial pressure of oxygen, which may counteract a reduced total pressure inside of the gas transfer membranes 102a such that oxygen still diffuses into the extra-capillary space of the bioreactor 150 while carbon dioxide is removed. The oxygen concentration of supplied air, the pressure of supplied air and/or the flow rate of supplied air may be varied over time to alter the amount of oxygen delivered to the extra-capillary space of the bioreactor 150. For example, the amount of oxygen delivered may be increased over time to deliver oxygen at a higher rate when cells, or a population of cells, are maturing.

In some examples, the bioreactor 150 is used to grow cells in suspension. Cells in suspension can move in the extra-capillary space, typically because they are entrained in a flow of a liquid moving within the extra-capillary space. The flow can be induced by various methods such as one or more of: a mixer, such as mixer 160; flowing liquids into and out of the extra-capillary space for example by way of fittings 164; or, rocking, spinning or otherwise moving the bioreactor 150. The cells can be suspended alone, or attached to carriers that are also in suspension. The cells may be, for example, stem cells, CD34+ cells, RBCs or any other cells mentioned herein, including eukaryotic, microbial or plant cells. In other examples, the bioreactor 150 is used to grow adherent cells.

In some examples, a portion of the cells may be restrained within small spaces such as the gaps between adjacent membranes 102 within a zone 104, 106, 108, 110, particularly within compound zones having oblique or perpendicular sets of membranes 102 such as within compound zones 104/108 104/110, 106/108 and 106/110. Optionally, such a restraint may effect only a portion of the cells in the bioreactor 150 while other cells circulate more freely through the parts of zones 104, 106, 108, 110 with membranes in only one direction, or through larger gaps such as gaps between groups of membranes 102, for example gaps between zones 104, 106, 108, 110, or gaps between membranes 102 or zones 104, 106, 108, 110 and interior surfaces of walls of the bioreactor 150. Alternatively or additionally, such a restraint may be temporary. For example, a collection of restrained cells may emerge towards the end of a cell growth period but be dislodged for (i.e. just before or during) a harvest phase of a process. In some examples, at least a portion of the restrained cells is maintained in the bioreactor 150 while other cells are harvested. These restrained cells can, for example, function to seed the bioreactor for a subsequent growth phase in a batch process, or maintain a population of cells in the bioreactor 150 despite harvesting in a continuous or semi-continuous process. The degree of restraint may be modified, for example, by modifying the spacing between membranes 102, the tension or slack of the membranes 102 and whether the membranes 102 are woven together or merely overlap each other. Optionally, a reactor 150 may be used to grow adhered or retained cells and suspended cells at the same time.

In some examples, cells that are restrained within small spaces in the bioreactor may build matrices around themselves. Even if these matrices do not materially adhere the cells to the membranes 102 they can, over time, inhibit removal of cells within the matrix from a membrane zone.

To control the average age of restrained cells, a dislodging force can be applied periodically to remove some or all of the restrained cells. The dislodging force can be applied, for example, in one or more episodes during a growth phase, or before or during a harvesting phase. The dislodging force can be created, for example, by temporarily increasing the power of a mixer, flushing a liquid through the extra-capillary space of the bioreactor 150, introducing bubbles (for example of nitrogen) into the extra-capillary space, moving the bioreactor 150, temporarily changing the direction of a mixer, or temporarily changing the inlet and/or outlet location of a liquid added to the the extra-capillary space, for example by way of fittings 164. Optionally, cells can also be dislodged by using a chemical or enzymatic treatment or by inducing a change in an environmentally responsive material of the membranes 102.

Maintaining at least a portion of the cells in suspension, or dislodging restrained cells, produces mechanical stress on the membranes 102. Optionally, the outside diameter of the membranes 102 may be 0.5 mm or more, 0.7 mm or more or 1.0 mm or more. Larger diameter membranes 102 are able to withstand more mechanical stress than smaller diameter membranes. At longer lengths between potting heads 142, for example 20 cm or more, larger diameter membranes 102 may also provide a more nearly even distribution of nutrients. Alternatively or additionally, the membranes 102 may be reinforced, for example by being coated on a tubular braid, or made by being made in a thermally induced phase separation (TIPS) process.

The ability to grow and harvest cells, for example to keep at least a portion of the cells in suspension or to dislodge restrained cells, is also enhanced by having a controlled spacing between membranes 102 and/or a low packing density. The packing density of membranes 102 within a zone or compound zone (measured as sum of the cross-sectional areas of the membranes divided by cross-sectional area of the zones) may be 25% or less, 20% or less, or 15% or less. In addition, gaps can be provided, as shown for example in FIG. 1, between compound zones and/or between a zone or compound zone and the inside surface of the bioreactor 150. Optionally, the membranes 102 are laid out in a regular pattern with controlled spacing between adjacent membranes. In the example of FIG. 1, the membranes 102 are laid out in a stack of layers, optionally forming a rectilinear array. Within a layer, adjacent membranes 102 are spaced apart from each other by gaps (measured between outer surfaces of adjacent membranes) of 0.2 mm or more, 0.5 mm or more, 0.7 mm or more or 1.0 mm or more. Layers of membranes are spaced apart from each other by gaps (measured between planes defining the opposed surfaces of adjacent layers) of 0.2 mm or more, 0.5 mm or more, 0.7 mm or more or 1.0 mm or more. The gap between adjacent layers of membranes may also be at least as large as the diameter of perpendicular membranes, if any. The spacing between membranes in a layer and/or the spacing between layers is optionally different for perfusion membranes 102b than for gas transfer membranes 102a. The spacing between membranes or between layers, potting densities and the arrangement of membranes into layers or arrays are preferably determined and/or measured within the potting heads 142. A defined spacing is optionally maintained along the length of the membranes 102, for example by tension in the membranes, weaving orthogonal membranes together. Alternatively, the membranes 102 may be slackened such that they form a stable matrix under gentle mixing, but the matrix may be selectively disturbed to release cells from the matrix.

The diameter of the element 140 shown in FIG. 1, measured between inside surfaces of the potting heads 142, may be for example in the range of 5 cm or more, 10 cm or more, 15 cm or more or 20 cm or more. The diameter may be, for example, 40 cm or less or 30 cm or less. In examples where the element 140 does not define a round interior cross-section, one or more dimensions between opposed interior surfaces of the element 140 may be within these ranges. Longer membranes 102 may be strengthened if required by increasing their diameter, using multifilament yarns of membranes 102, weaving orthogonal membranes 102 together, or using braid supported or TIPS membranes 102.

Optionally, an element 140 may have additional divisions among the membrane 102 to create more zones. For example, the element 140 of FIG. 14 has four zones 103, 104, 105, 106 of perfusion membranes 102_a_ and four zones 107, 108, 109, 110 of gas transfer membranes 102_b_. Other examples may have more or less zones and there may be different numbers of zones for perfusion membranes than for gas transfer membranes. Creating more zones can assist with keeping at least some of the cells in suspension as the diameter of the element 140 increases. In some examples, an element 140 or bioreactor 150, has most, i.e. 50% or more or 80% or more, or all of its zones, with at least one dimension across the zone that is 10 cm or less or 5 cm or less. In some examples, an element 140 or bioreactor 150 has most, i.e. 50% or more or 80% or more, or all of its zones, with two or three mutually perpendicular dimensions across the zone that are 10 cm or less or 5 cm or less.

Figure 14:
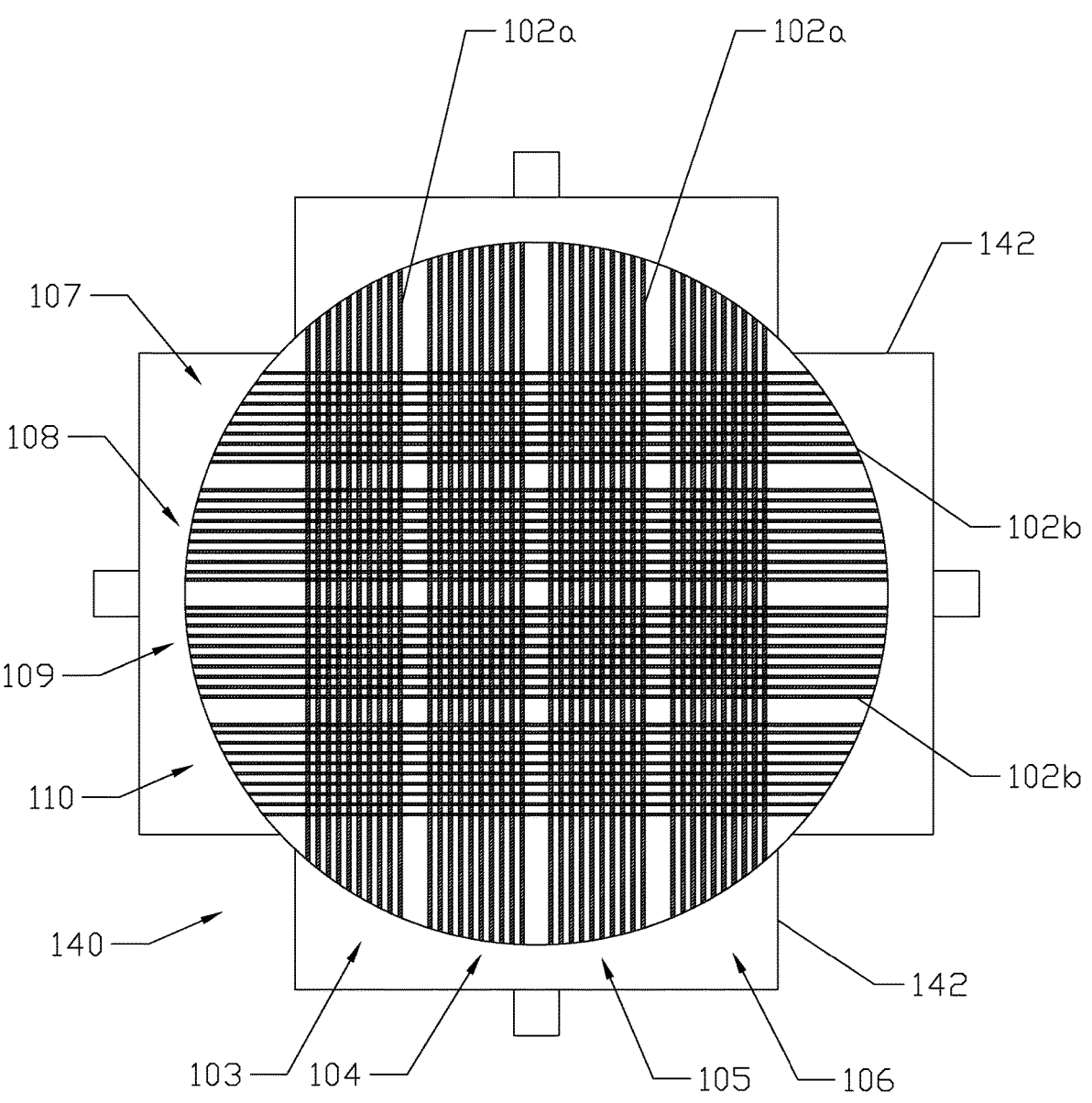
FIG. 14 shows a top view of a segment of a second bioreactor.

The elements 140 of FIGS. 1 and 14 may be used in a horizontal orientation, as shown for example in FIGS. 2-4. The height of the bioreactor 150, measured as the cumulative height of the elements 140, may be more than the inside diameter of the elements 140. Optionally, the height of the bioreactor 150 may be 2 times or more, 5 times or more or 10 times or more, than the inside diameter of the elements 140. To help enable cell circulation, one or more mixing layers 302 may be added between the elements 140, for example as shown in FIG. 13. Similarly, one or more harvest layers 300 may be added between the elements 140. The extra-capillary space of the bioreactor, measured as the interior volume of the bioreactor but excluding the volume occupied by the membranes 102, may be 1 L or more or 10 L or more or 50 L or more. The extra-capillary space of the bioreactor may be 1000 L or less or 100 L or less.

Figure 15:
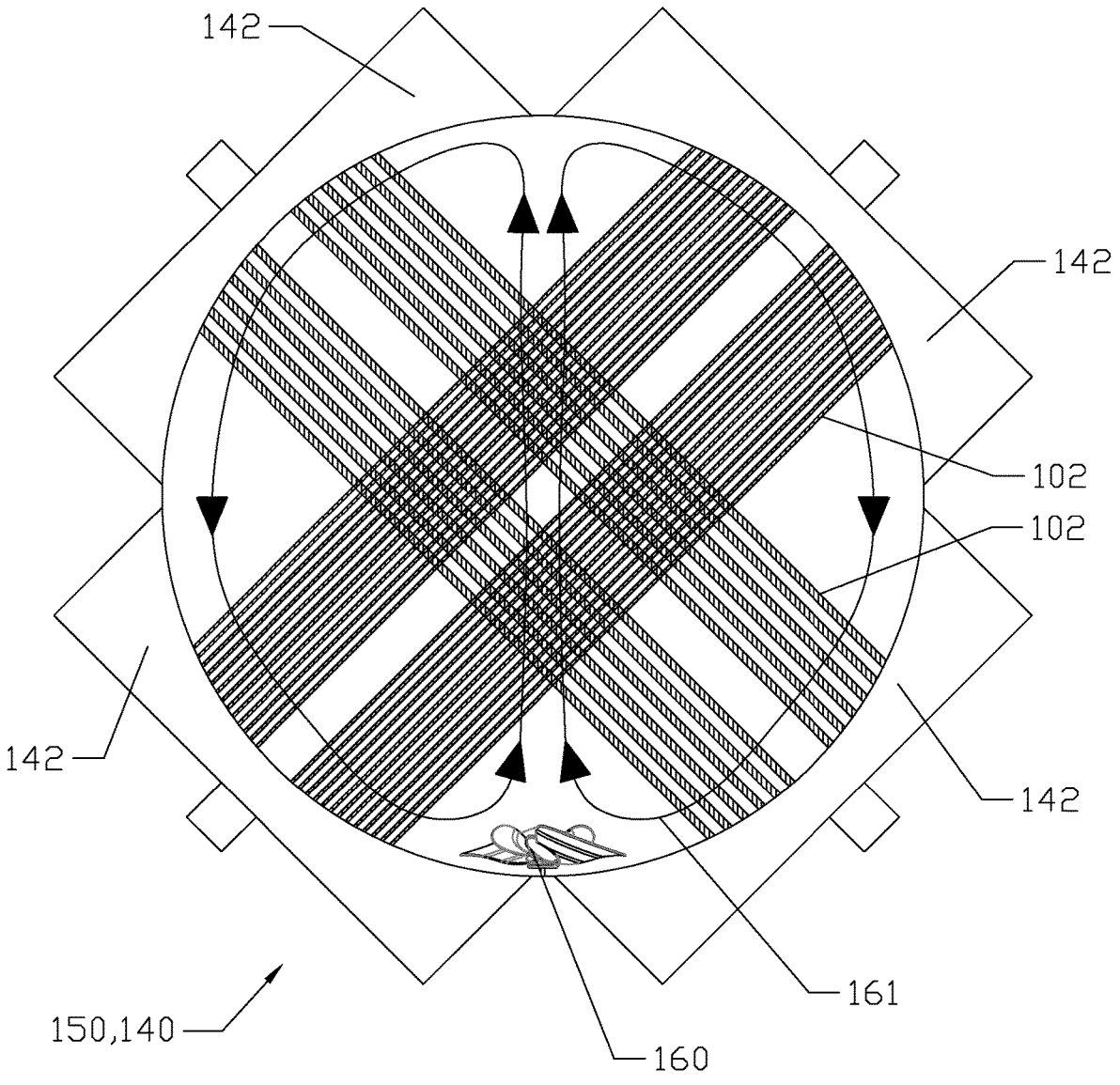
FIG. 15 shows a cross section of a third bioreactor, cut perpendicular to a central longitudinal axis of the third bioreactor.
Figure 16:
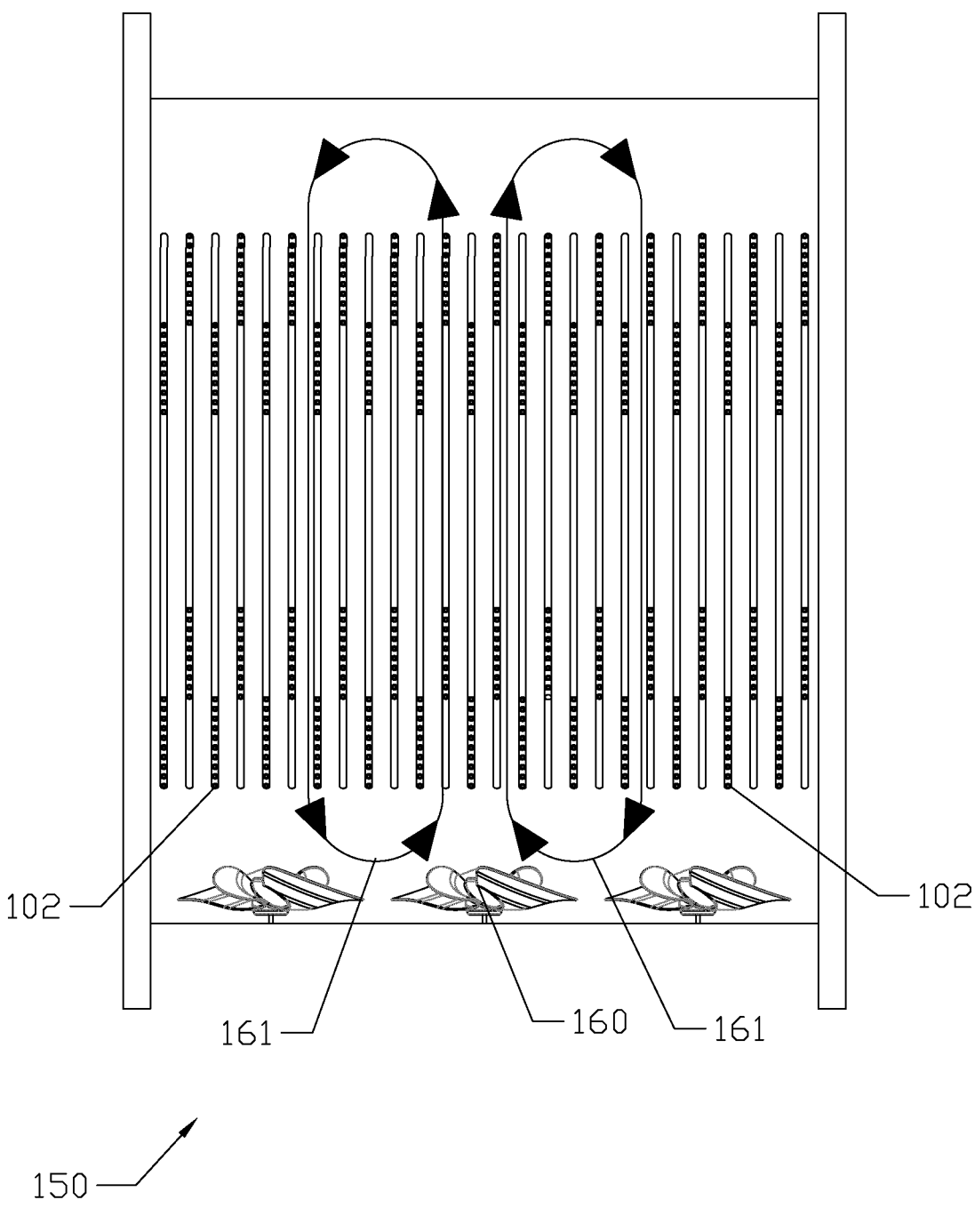
FIG. 16 shows another cross section of the third bioreactor, cut along the central longitudinal axis of the third bioreactor.

FIGS. 15 and 16 show an alternative wherein the bioreactor 150 is used with the elements 140 in a vertical orientation. The height of the bioreactor 150 oriented as in FIGS. 2-4 becomes the length of the bioreactor 150 oriented as in FIGS. 15 and 16. The membranes 102 may be oblique to the horizon, for example at 30-60 degrees to the horizon or at about 45 degrees to the horizon as shown. Alternatively, the membranes 102 may be parallel or perpendicular to the horizon. One or more mixers 160, for example on the bottom of one or more of the elements 140, can be used to create a circulation pattern 161 that crosses the diameter of the elements 140. The circulation pattern 161 may be substantially independent of the length of the bioreactor 150. Accordingly, the bioreactor 150 can be varied in length, optionally with a corresponding variation in the number of mixers 160, without reducing the effectiveness of the circulation pattern 161. In some examples, the orientation of the membranes 102, elements 140 or bioreactor 150 of FIGS. 15 and 16 may produce less retention of cells, particularly in zones with two oblique sets of membranes 102, compared to the orientation of FIGS. 1-5. Alternatively, the gaps between membranes 102 in a layer, and/or the gaps between layers, may be decreased with the orientation of FIGS. 15 and 16.

In either orientation, circulation within the bioreactor 150 or movement of the bioreactor 150 may be provided to generally homogenize one or more operating parameters in the bioreactor. Alternatively, one or more operating parameters may be intentionally varied, for example along the height/length of the bioreactor 150, across the width/diameter of the bioreactor 150, or in a radial direction extending outwards from a central longitudinal axis of the bioreactor 150. An operating parameter may be a parameter measured in the extra-capillary space, for example, temperature, pH or the concentration of a compound such as dissolved oxygen or a nutrient. Alternatively, an operating parameter may relate to the transfer of a compound to or from membranes 102. Alternatively the operating parameter may relate to the strength of circulation, or the time or extent to which cells are permitted to be restrained within a zone rather than freely circulating.

Although some of the examples herein relate to suspension cell cultures, the bioreactor 150 can also be used to grow adherent cells. In addition to any other method or apparatus element described herein to help dislodge adhered cells, thermo-responsive materials on the membranes 102 may also be activated to help dislodge the cells.

The element 140 described above is formed in mold. Braces 114 are optionally part of the mold, but otherwise the element 140 is separated from the mold before being assembled into the reactor 150. Optionally, some or all of a mold may remain as part of an element.

Figures 21A, 21B:
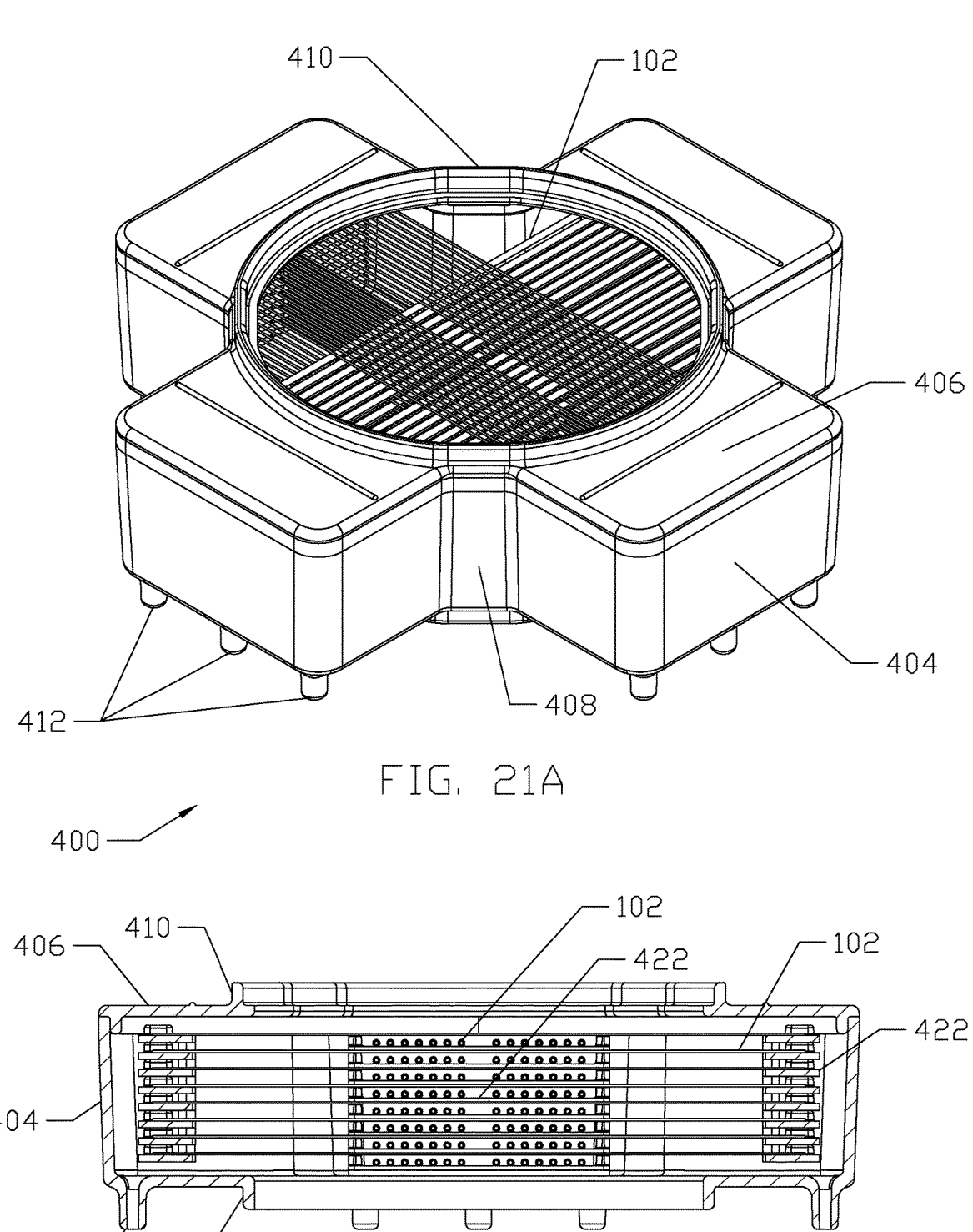
FIGS. 21A and 21B show isometric and a vertical cross-sectional view of an assembled mold of FIG. 20.

Further examples bioreactor and methods of making them are described below. FIGS. 21A and 21B show sets of membranes 102 in a mold 400. The mold 400 is used to make a second element 402, shown for example in FIG. 23. In the casting process, liquid potting material 428, for example an epoxy or polyurethane resin, is poured into the mold 400 and then cures to form a solid, as shown for example in FIG. 22. In the example shown, the mold 400 is used for spin casting. The mold 400 is spun as the liquid potting material 428 is added to the mold to force the potting material 428 to the outside of the mold 400. The mold 400 continues spinning until the liquid potting material 428 solidifies. Alternatively, static potting may be used. In this case, a part of the mold 400 that defines a potting cavity 416 is oriented at the bottom of the mold 400 while liquid potting material 428 is poured into it and then allowed to cure. The mold 400 is then rotated to place another potting cavity 416 at the bottom of the mold and more potting material 428 is added. The process of static potting is repeated until potting material 428 has been poured into each potting cavity 416.

A second element 402 produced in the mold 400 may be similar to an element 140 as shown in FIG. 1. In the case of element 140, the potting heads 142 are removed from a mold, except that the braces 114 may have been part of the mold. In the case of second element 402, more of the mold 400 is retained. In particular, the potting material 428 is surrounded by parts of the mold 400 except at a face of the potting material 428 wherein the ends of the membranes 102 are exposed. The second element 402 may be used, or modified or adapted for use, in any method, apparatus or system described with reference to the element 140. Similarly, the element 140 can be used, or modified or adapted for use, with any method, apparatus or system described for the second element 402.

Figure 27:
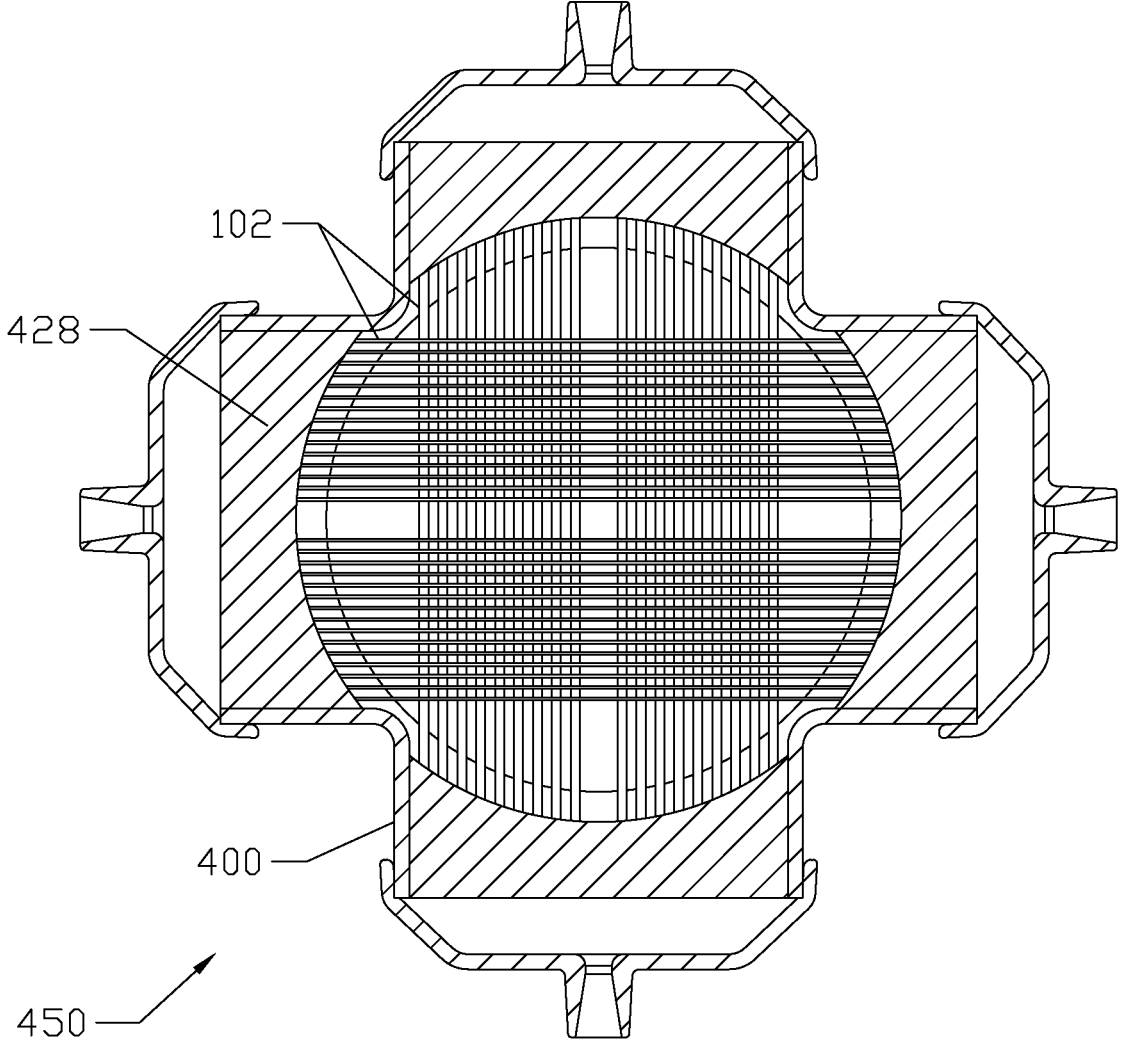
FIG. 27 shows a cross-section of another alternative second reactor.

In the example shown in FIG. 21A, the mold 400 is made of a transparent plastic such as polycarbonate. A portion of the mold forms a panel 408. The panel 408 allow for looking into the extra-capillary space or using a light based analysis method to determine a property of first media in the ECS. The panels 408 optionally allow for taking measurements from one or more light activated sensor foils placed on the inside of the window 408, in contact with media in the extra-capillary space, as described above for the braces 114. Alternatively, the mold 400 may be made of opaque material and other forms of sensors may be placed on or through the panels 408. In another alternative (for example as shown in FIG. 27), the mold 400 is reconfigured to produce a wider area for potting material 428 and to eliminate the panels 408 or reduce the size of the panels 408.

Referring to FIGS. 21A and 21B, the mold 400 has a first part 404 and a second part 406. The first part 404 and the second part 406 are assembled together, optionally with an adhesive, after the membranes 102 are inserted between them. When the mold 400 is assembled, potting cavities 416 are created where potting material 428 will be added (as shown for example in FIG. 22). During the spin casting process, liquid potting material 428 flows into the potting cavities 416 of the mold 400 through one or more resin ports 412.

The second element 402 has two apertures 410 on opposed sides of the second element 402. Optionally one or both of the apertures 410 include an additional feature, for example a raised ring in the example shown. Alternatively, an aperture 410 maybe a simple opening in the mold 400. Optionally, the outside diameter of one of the apertures 410 is generally the same as the inside diameter of the other aperture 410. Multiple second elements 402 can be stacked together by inserting the smaller aperture 410 of a second element 402 into the larger aperture of another second element 402. Optionally, the apertures 410 of two or more second elements 402 are connected by an adhesive or solvent bonded together. Alternatively, the apertures 410 may be threaded such that two or more second elements 402 may be screwed together, or two apertures 410 may be press fit together.

Figure 17A:
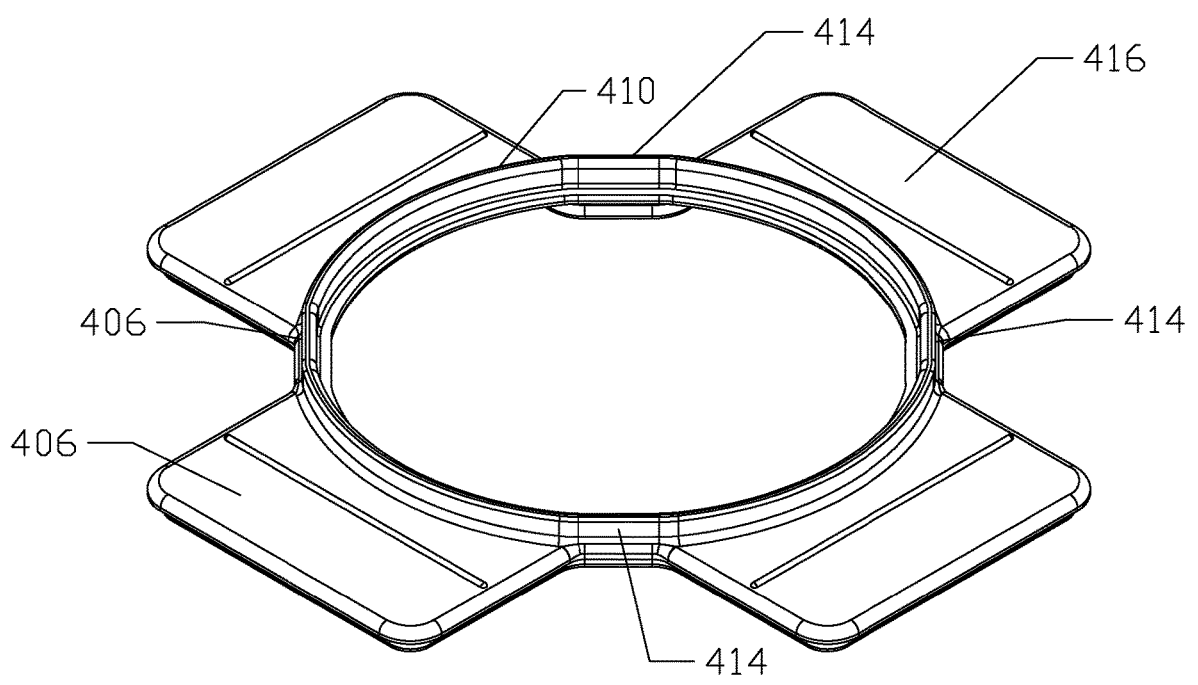
FIG. 17A shows the top of a second part of a mold.
Figure 17B:
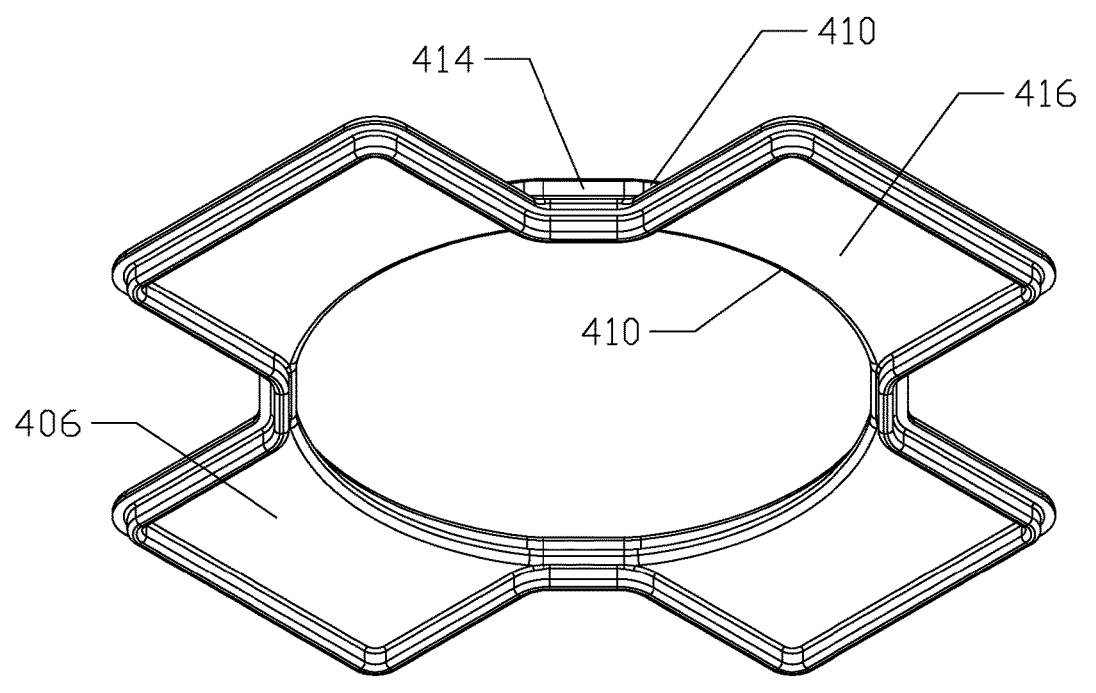
FIG. 17B shows the bottom of the second part of the mold of FIG. 17A.

FIGS. 17A and 17B show the second part 406 of the mold 400. FIG. 17A shows primarily the outside surfaces of the second part 406. FIG. 17B shows primarily the inside surfaces of the second part 406. The aperture 410 may have one or more registration areas 414. In the example shown, there are four registration areas 414 equally spaced around the aperture 410. Each registration area 414 is a flat spot on the otherwise round aperture 410. In combination with corresponding registration areas on the first part 404 of the mold 400, the registration areas cause the potting cavities 426 in a stack of second elements 402 to be aligned with each other.

Figure 18A:
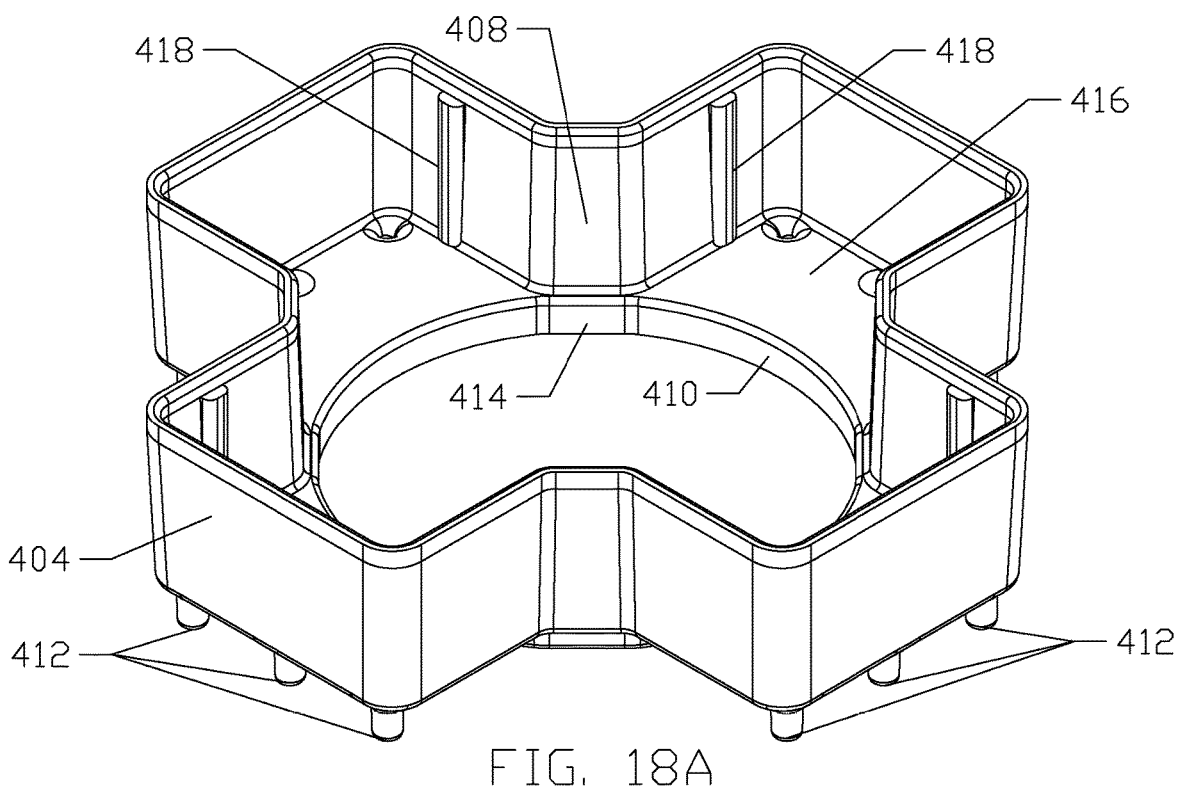
FIG. 18A shows the inside of a first part of a mold.
Figure 18B:
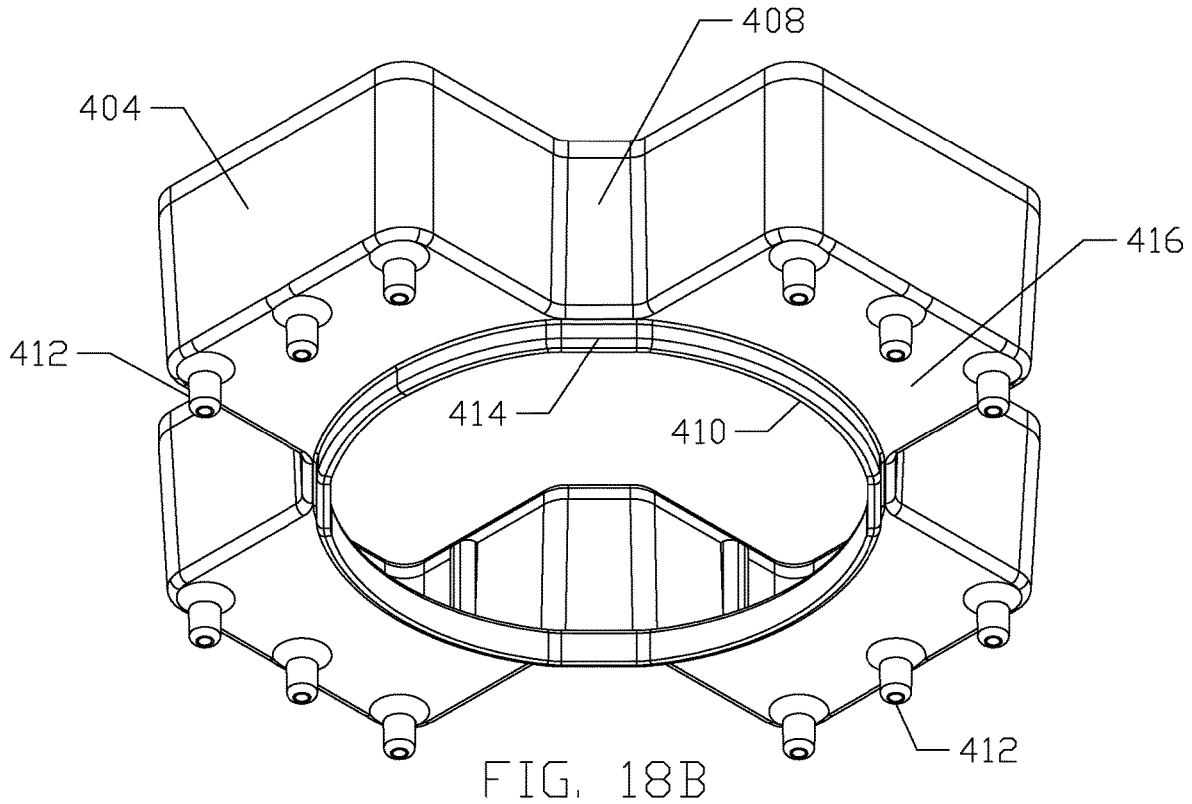
FIG. 18B shows the outside of the first part of the mold of FIG. 18A.

FIGS. 18A and 18B show the first part 404 of the mold 400. FIG. 18A shows primarily the inside surfaces of the second part 406. FIG. 18B shows primarily the outside surfaces of the second part 406. The aperture 410 may have one or more registration areas 414. In the example shown, there are four registration areas 414 equally spaced around the aperture 410. Each registration area 414 is a flat spot on the otherwise round aperture 410. As discussed above, in combination with corresponding registration areas 414 on the second part 406 of the mold 400, the registration areas 414 cause the potting cavities 416 in a stack of second elements 402 to be aligned with each other.

In the example shown, the mold 400 has four potting chambers 416 where potting material 428 will be added. Optionally, during the potting process the potting material 428 (shown for example in FIG. 22) does not extend radially inward beyond the potting chambers 416 and therefore does not flow through the inside of the mold 400 between potting chambers 416. Each potting chamber 416 has one or more resin ports 412. During potting, potting material 428 flows from a reservoir outside of the mold 400 through tubes connected to the resin ports 412 and into the potting chambers 416. The potting material may flow by way of a pump or by centrifugal force generated by spinning the reservoir with the mold 400.

Figure 19A:
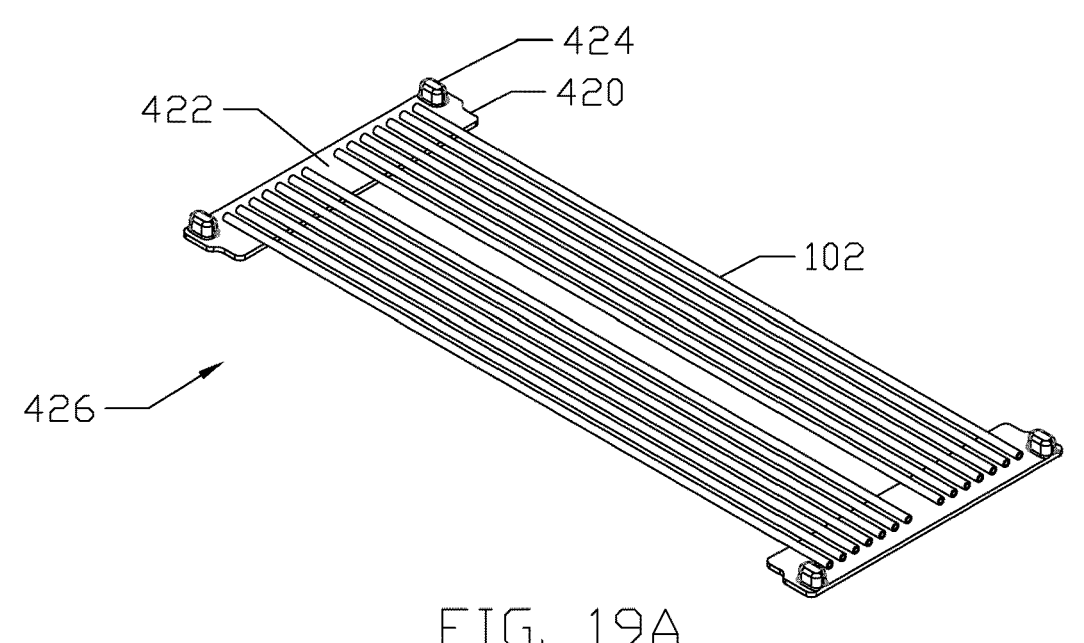
FIGS. 19A, 19B and 19C show isometric, top and end views of a membrane plate assembly.
Figure 19B:
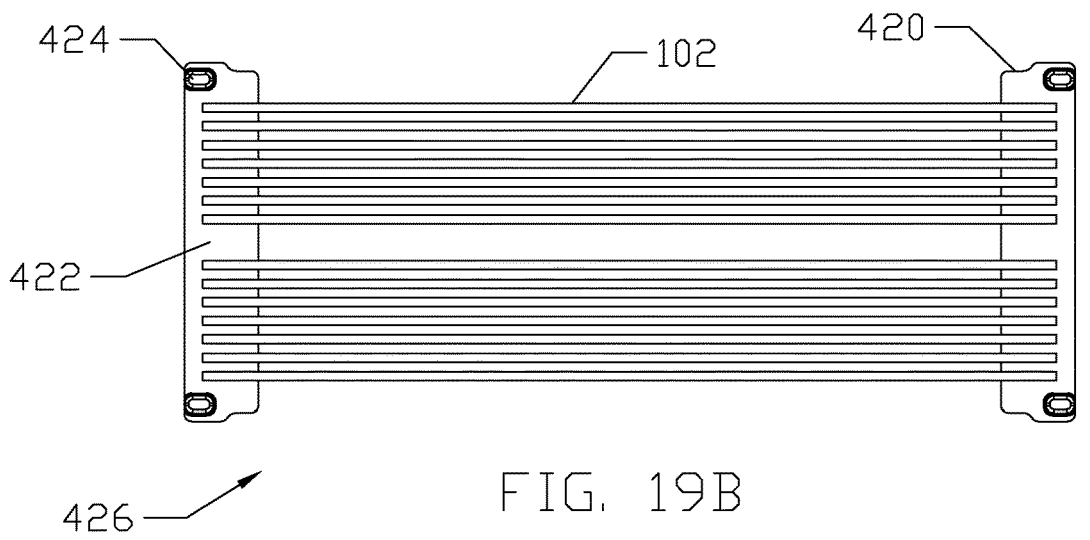
Figure 19C:
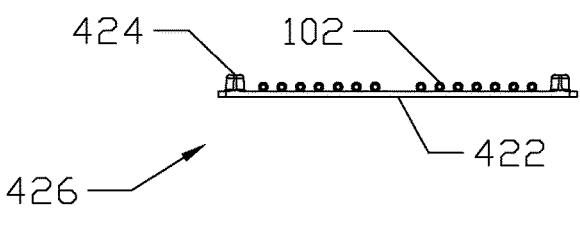

As shown in FIG. 18A, each potting chamber 416 also has one or more ribs 418. In the example shown, there is one rib 418 on each side of each potting chamber 416. The ribs 418 engage with notches 420 in plates 422 shown in FIGS. 19A, 19B and 19C. Membranes 102 are attached to the plates 422, for example by an adhesive or welding, to form a membrane plate assembly 426. The ends of the membranes 102 are typically closed before, or as a result of, being attached to the plates 422. The ribs 418 locate the plates 422 when they are inserted into the potting chambers 416. Alternatively, other features of the mold 400 and or the membrane plate assemblies 416 may be used to hold the membrane plate assemblies 416 in a selected location in the mold 400. The length of the membranes 102 may be selected, relative to the configuration of the mold 400 and the plates 422, such that the membranes 102 are taut when they are placed in the mold. Alternatively, the length of the membranes 102 may be selected, relative to the configuration of the mold 400 and the plates 422, such that the membranes 102 have some slack when the membranes 102 are placed in the mold 400. The membranes 102 may be divided into one or more sets of membranes 102 on a plate 424. Optionally, the membranes 102 of a set may be evenly spaced apart from each other. An even spacing of the membranes 102 in combination with taut membranes 102 promotes a controlled and even spacing of membranes 102 within the extra-capillary space. Alternatively, slackened membranes 102 move more in response to mixing which can inhibit cell attachment or help with cell harvesting for some cell types. The thickness of the plates 422, including optional spacing blocks 424, can be varied to control the distance between the membranes 102 attached to one plate 422 and the membranes 102 attached to another plate 422.

The membrane plate assemblies 426 may be customized, for example, by having one or more of selected membrane 102 type or size, a selected spacing between membranes 102 in a membrane plate assembly 426, a selected spacing between membrane plate assemblies 126, a selected taut or slack mounting of the membranes 102, or selected treatments of membranes 102, for example to may them protein fouling resistant or environmentally (i.e. thermally) responsive. By changing the membrane plate assemblies 426, a second element 402, second reactor 450 or compound reactor 550 may be produced that is suitable for use for growing a variety of cells or cell products. In some examples, the number of perfusion membranes 102a relative to the number of gas transfer membranes 102b is altered, only perfusion membranes 102a are provided, or only gas transfer membranes 102b are provided in a second element 402, second reactor 450 or compound reactor 550.

Figure 20:
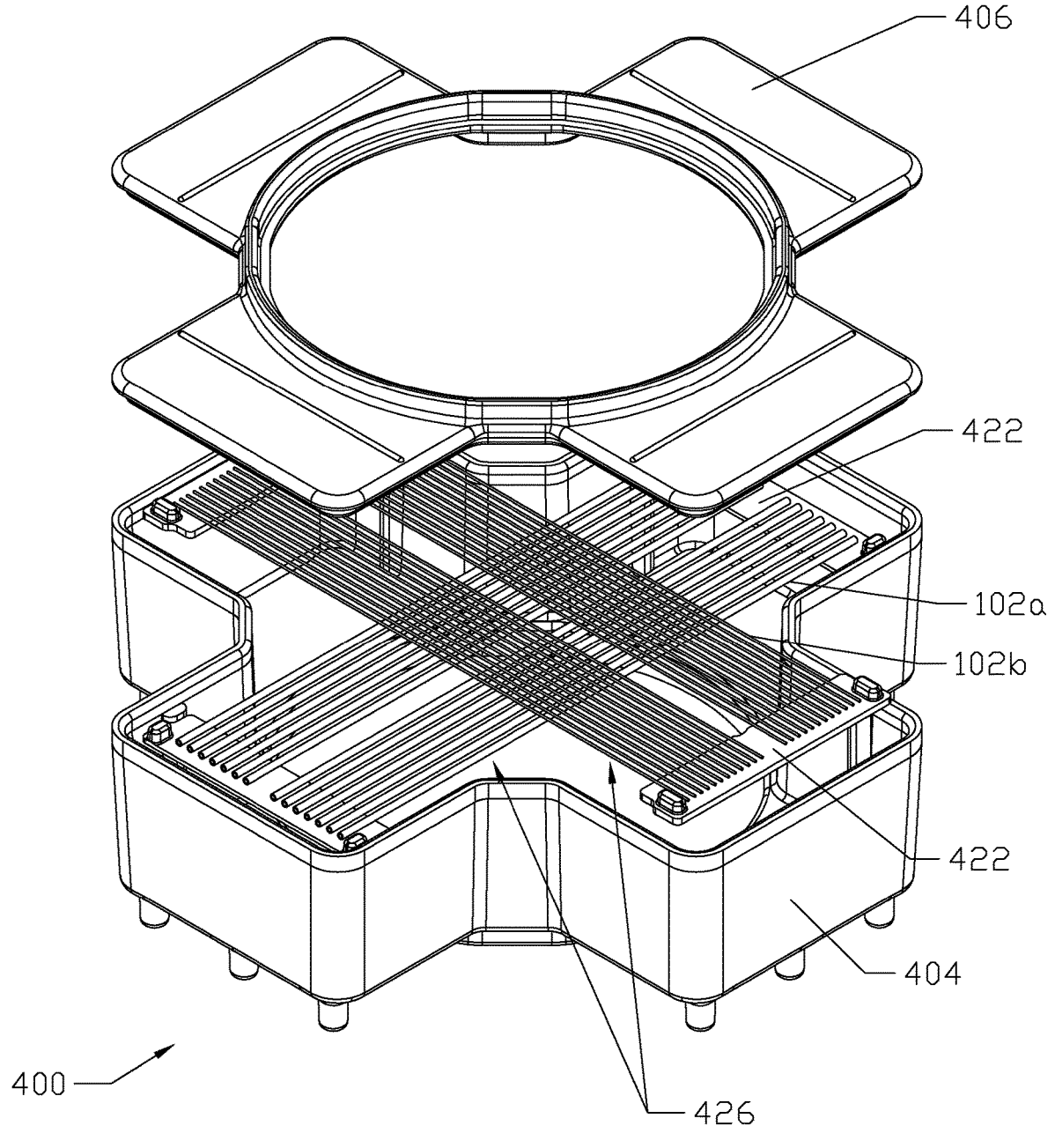
FIG. 20 shows a mold being assembled with the first part of the mold of FIGS. 18A and 18B, the second part of the mold in FIGS. 17A and 17B and membrane plate assemblies of FIGS. 19A-C.

FIG. 20 shows a mold 400 being assembled. Membrane plate assemblies 426 are inserted into the first part 404 of the mold 400. Two membrane plate assemblies 426 are shown in FIG. 20 but a mold 400 may contain multiple membrane plate assemblies 426, for example between 5 and 1000, or between 10 and 100, membrane plate assemblies 426. In the example shown, there are perfusion membranes 102a and gas transfer membranes 102b. Optionally, a mold 400 may be loaded with only perfusion membranes 102a or only gas transfer membranes 102b. In the example shown, alternating membrane plate assemblies 426 are oriented orthogonally to each other. In other examples, membrane plate assemblies 426 may form different patterns, for example two or three membrane plate assemblies 426 in one direction for every membrane plate assembly 426 in the orthogonal direction. In other examples, the membrane plate assemblies 426 in a mold 400 may all be oriented in the same direction. In other examples, the membranes 102 of one membrane plate assembly 426 may be woven with the membranes 102 of an orthogonal membrane plate assembly 426.

Figure 22:
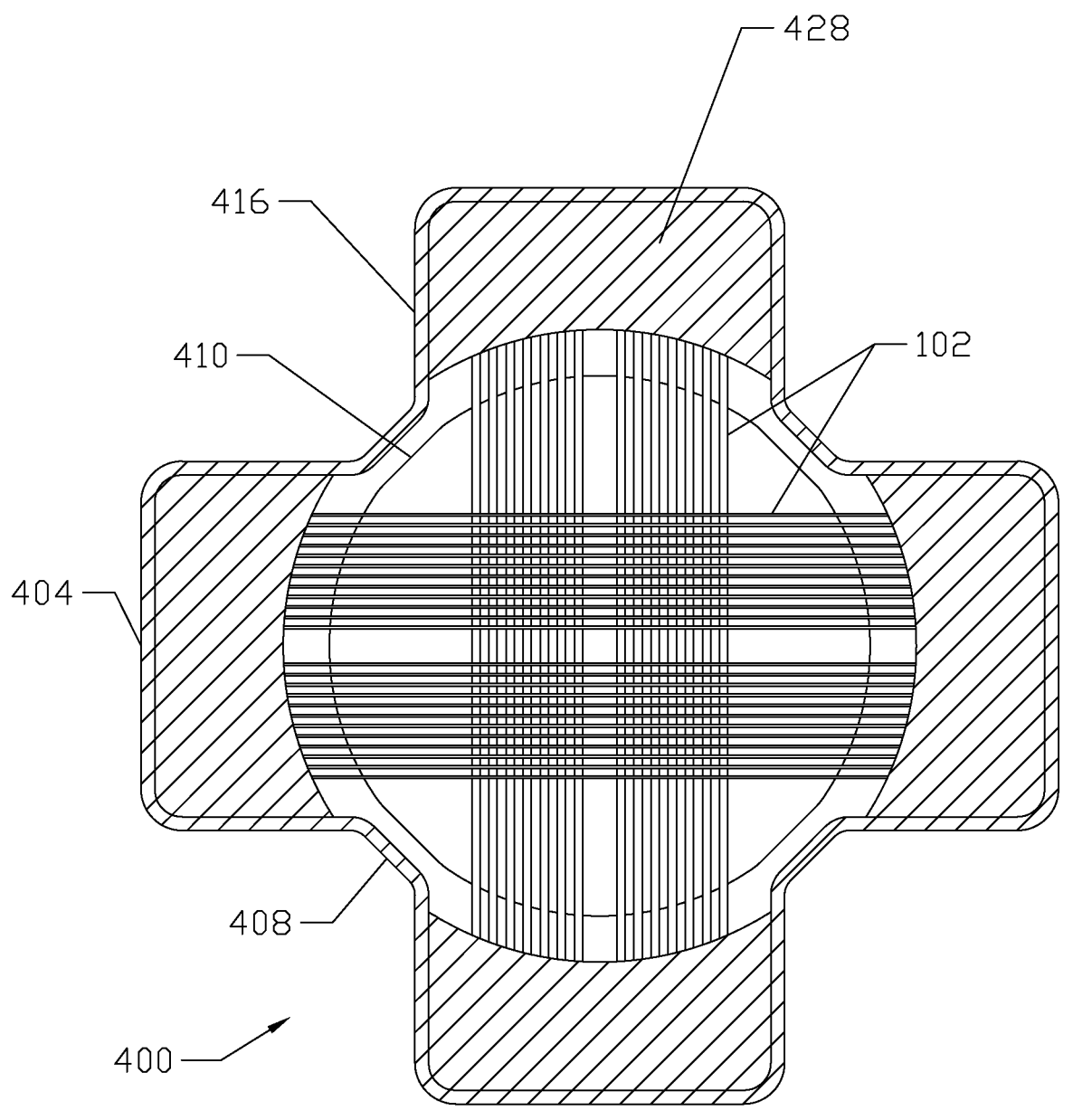
FIG. 22 shows a horizontal cross section of a mold with potting material added to it.

FIGS. 21A and 21B (also discussed above) shows the mold 400 assembled and ready for spin casing. FIG. 22 shows a cross section of the mold 400 after spin casting. Potting material 428 has been added to each of the potting chambers 416 and enclosed the ends of the membranes 102. Once cured, the potting material 428 provides a seal to the outside surfaces of the membranes 102. Optionally, the potting material 428 also encloses the plates 422. In the example shown, the inside surfaces of the potting material 428 is withdrawn, i.e. radially displaced, from the panels 408. Optionally, by adding more potting material 428 during spin casting, the inside surfaces of the potting material 428 may be brought closer to, or substantially flush with, the edges of the panels 408. The panels 408 may be flat as shown, rather than curved, such that the potting material 428 may encroach on the edge of a panel 408 without flowing across the entire panel 408. In another option, some of the potting material 428 may be allowed to overflow the panels 408 from one potting chamber 416 to another. The potting material 428 may be transparent, for example a clear epoxy. In this case, potting material 428 may cover the panels 408 and still allow light to travel through the panels 408.

In the example shown, the membranes 102 are inset from the sidewalls of the potting chamber 416. Alternatively, membranes 102 may be placed closer to the sidewalls of the potting chamber 416. The size of the panels 408 (either their absolute size or their size relative to the size of the mold 400) may be varied, or the panels 408 may be removed. The example shown is for a relatively small mold 400 with a roughly 10-15 cm outside diameter. In a larger mold 400, for example with an outside diameter up to 30 cm or more or 60 cm or more, panels 408 of essentially the same absolute size may be used but the panels 408 will be relatively smaller in the larger mold 400. Accordingly, a portion of the volume of extra-capillary space that is not crossed by membranes 102 can be reduced (or increased). However, it is not always necessary or desirable to have more of the extra-capillary space crossed by membranes 102.

Having multiple potting chambers 416 divides the amount of potting material 428 into smaller units, which can help with managing the heat generated when the potting material 428 cures, and also facilitates having the panels 408 not covered with potting material 428. Optionally, particularly if the panels 408 are not required for example for sensors or to enhance mixing, the mold 400 may be re-configured to provide one continuous potting chamber 416.

Figure 23:
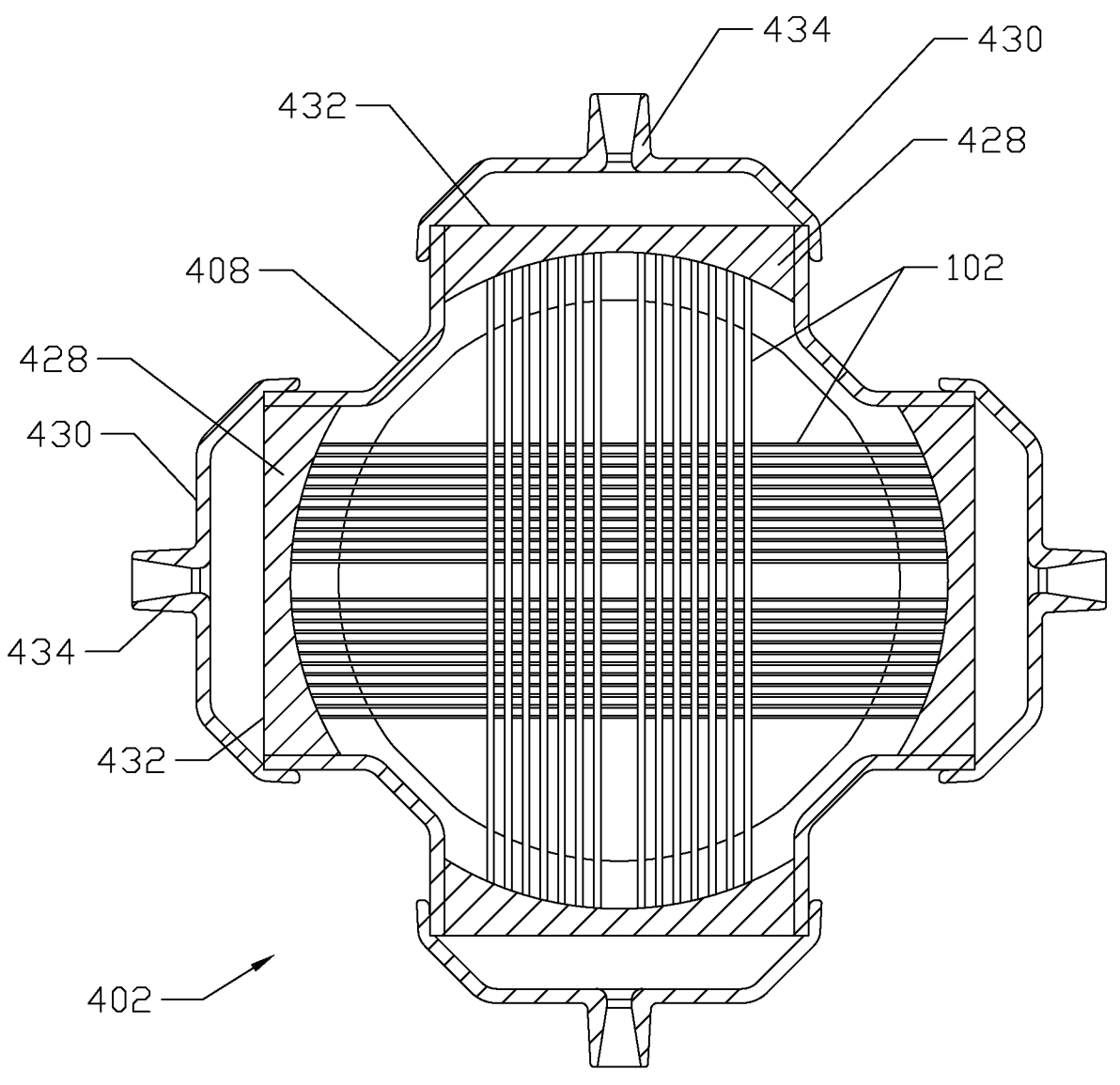
FIG. 23 shows a second element made with part of the molded assembly of FIG. 22 with some of the potting material, mold and membranes cut away and caps added.

FIG. 23 shows a second element 402. Starting with a potted mold 400 as shown in FIG. 23, the potting material 428 and potting chambers 416 are cut to produce a cut face 432. Portions of the potting material 428 and the ends of the membranes 102 beyond the cut face 432 are removed. Optionally, the cut face 432 may be inward of the plates 422 and the plates 422 may also be removed. The lumens of the membranes 102 are open at the cut face 432. Caps 430 are sealed, for example by an adhesive or solvent, to the remaining parts of the potting chambers 416. The ends of the membranes 102 are in fluid communication with the insides of the caps 430. Cap ports 434 allow a fluid to be added to, or withdrawn from, the caps 430, which in turn allows a fluid to be added to, or withdrawn from, a set of membranes 102.

Figure 24:
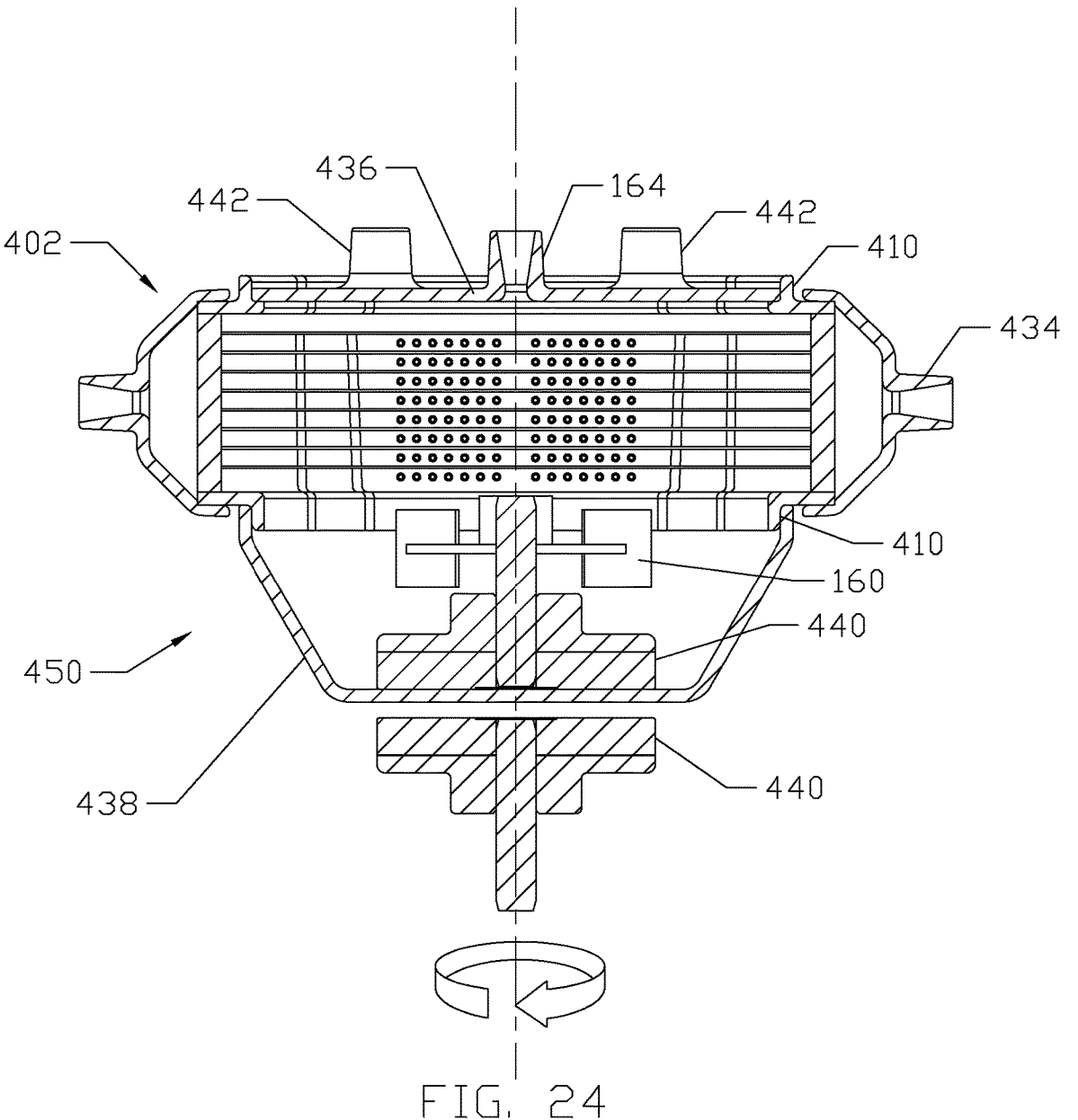
FIG. 24 shows a second reactor including the second element of FIG. 24 with a base plate having a mixer and a top plate.

FIG. 24 shows a cross section of a second element 402 used in a second reactor 450. A top plate 436 closes an upper aperture 410 at the top of the second reactor 450. A base plate 438 closes a lower aperture 410 at the bottom of the second reactor 450. A mixer 160 is attached to a magnet 440 in the base plate 438. A second magnet 440 outside of the second reactor 450 is attached to a motor (not shown) and placed near or against the second reactor 450. The magnets 440 couple the motor to the mixer 160 to allow the mixer 160 to be rotated inside the second reactor 450. A shaft 162 extending past the membranes 102 as in FIG. 2 is not required. Although only one of the second elements 402 is shown in FIG. 24, as described further below in relation to FIG. 29A, multiple second elements 402, for example between 2 and 100 second elements 402, may be assembled together into a compound reactor 550. For example, the aperture 410 of one second element 402 may be attached to the aperture of another second element 402 to create a stack of second elements 402.

Figure 29A:
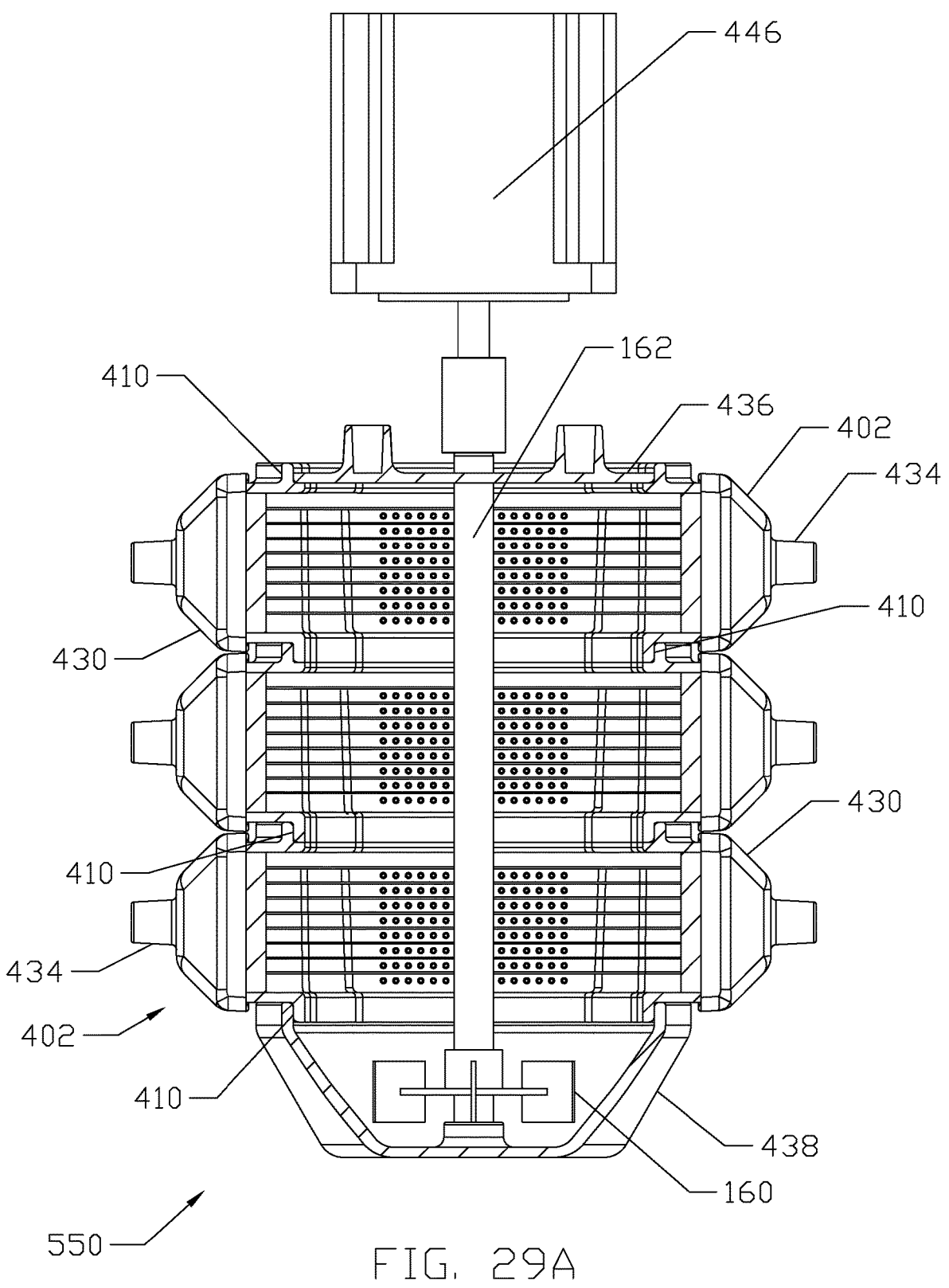
FIGS. 29A, 29B and 29C show compound reactors with multiple second elements and optionally a harvest layer.

Referring to FIG. 24 or FIG. 29A, each cap 430 in the second reactor 450 has a single cap port 434. Optionally, one or more caps 430 of the second reactor 450 may have two or more cap ports 434. In a cap 430 with two or more cap ports 434, two of the port caps 434 may be analogous to openings 204a and 204b of fluid control module 151 of FIG. 5. A network of pipes and valves may be arranged as shown in FIG. 6 and connected to the caps 430. The second reactor 450 or compound reactor 550 can thereby be connected to a fluid supply system for perfusion zones as shown in FIG. 9 and/or a fluid supply system for gas transfer zones as shown in FIG. 10. In the case of a compound reactor 550, the fluid supply to each second element 402 may be separately controlled.

Referring to FIG. 24, the top plate 436 may have one or more fittings 164 that provide access to the extra-capillary space. A fitting 164 can be used to add first media, or a particular substance such as a growth factor or nutrient, to the extra-capillary space. Alternatively, a fitting 164 may be used to remove a substance from the extra-capillary space. In one example, a fitting 164 is used to vent any gasses that collect at the top of the second reactor 450. In another example, a fitting 164 is used to connect a sampler to the extra-capillary space.

The top plate 436 may have one or more adapters 442. In one example, an adapter 442 is used to attach a sensor body connected to a fiber optic cable in a hole in the top plate 436. The fiber optic cable is used to read a sensor dot attached to the inside of the sensor body in the adapter 442. Sensor dots are made, for example, by PreSens and can be used to measure pH, dissolved oxygen concentration, dissolved carbon dioxide concentration or other aspects of the extra-capillary space. Alternatively, an adapter 442 may be used to support another type of probe or sensor.

Figure 25:
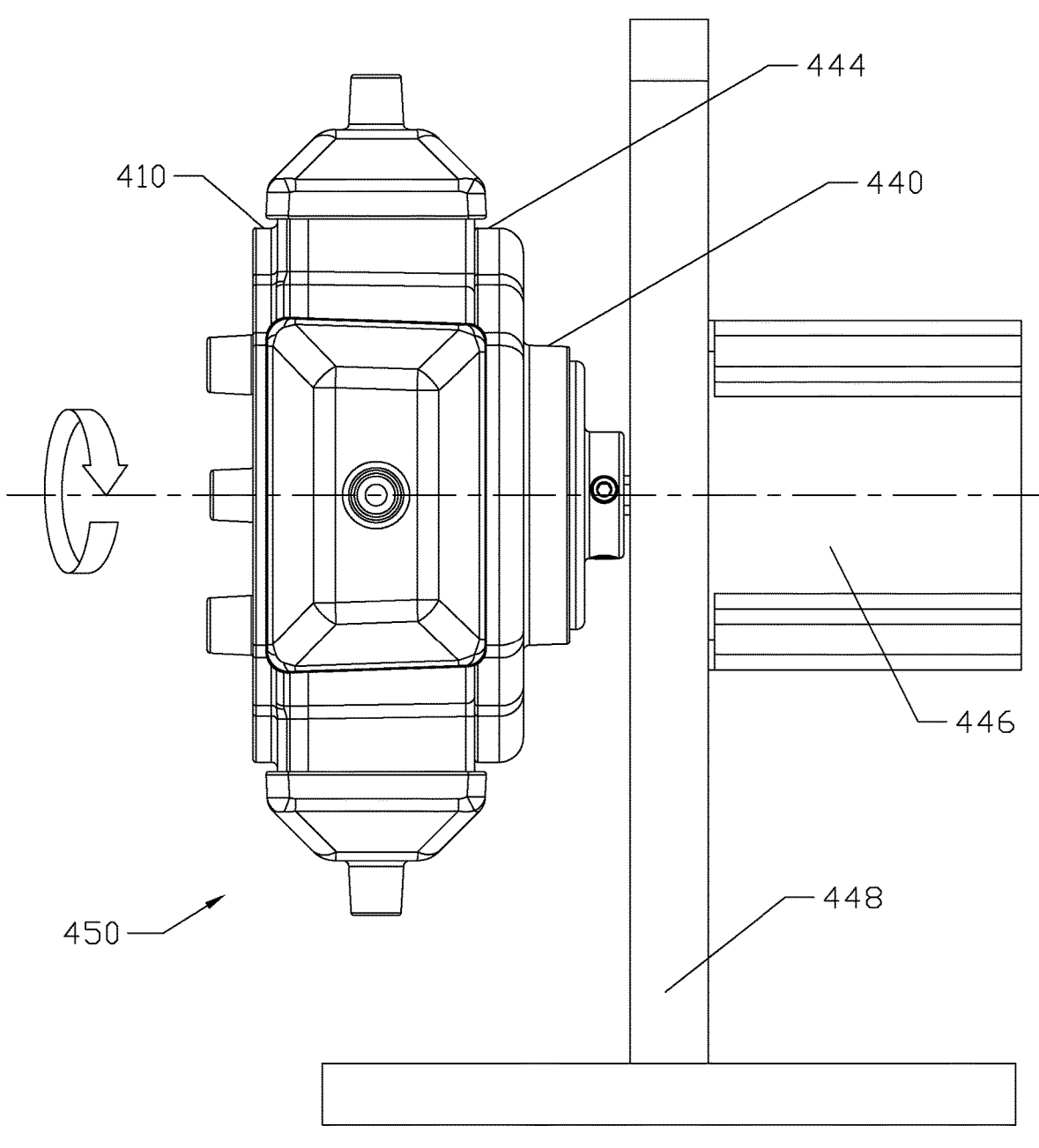
FIG. 25 shows another second reactor with a magnetic base attached to a motor for rotating the second reactor.

FIG. 25 shows a variation of the second reactor 450 with a magnetic base 444 in pace of the base plate 438 of FIG. 25. The magnetic base 444 has a ferromagentic insert (not visible) held in a fixed position in the magnetic base 444. The ferromagnetic insert allows the second reactor 450 to be coupled to a magnet 440 outside of the second reactor 450. The magnet 440 is attached to a motor 446, for example a stepper motor, that is supported on a stand 448. The second reactor 450 is thereby suspended from the stand 448. The second reactor 450 rotates with the motor 446. The motor 446 can be activated to move the second reactor 450, for example to rotate or rock the second reactor 450 or to periodically invert the second reactor 450. In an example, the second reactor 450 rotates the second reactor 450 in one direction (i.e. clockwise) for 1-5 rotations, and then rotates the second reactor 450 in the other direction (i.e. counter-clockwise) for 1-5 rotations, in a repeated pattern. A shaft 162 extending past the membranes 102 as in FIG. 2 is not required. When the second reactor 450 is mixed by rotating or otherwise moving it, the potting material 428 may be intentionally provided such than an inner surface of the potting material 428 is displaced radially outward from an inner surface of the panels 408. In this way, the panels 408 protrude into the extra-capillary space and form vanes or ridges than can enhance the mixing caused by moving the second reactor 450.

Figure 26A:
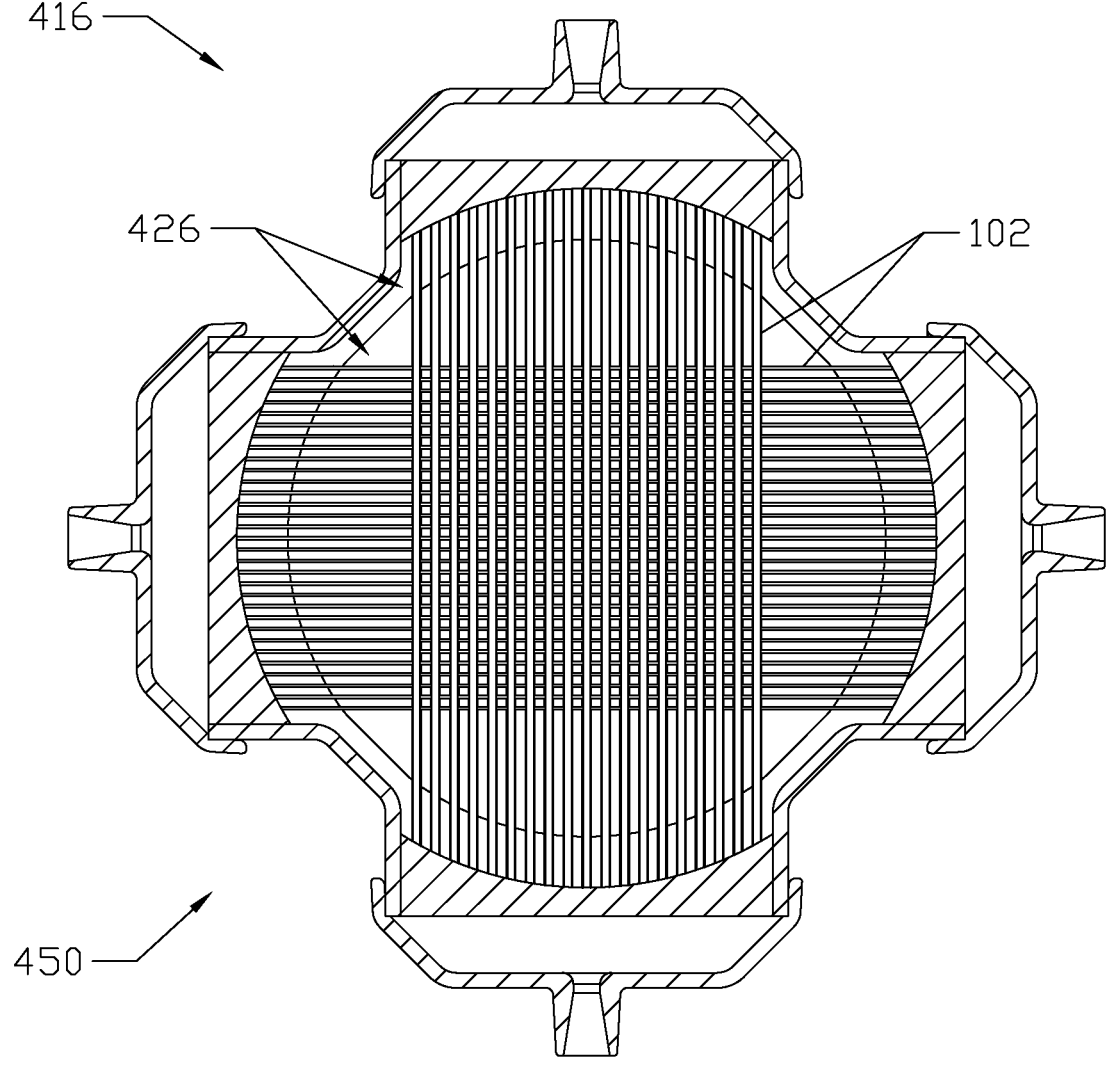
FIGS. 26A and 26B show cross-sections of alternative second reactors.
Figure 26B:
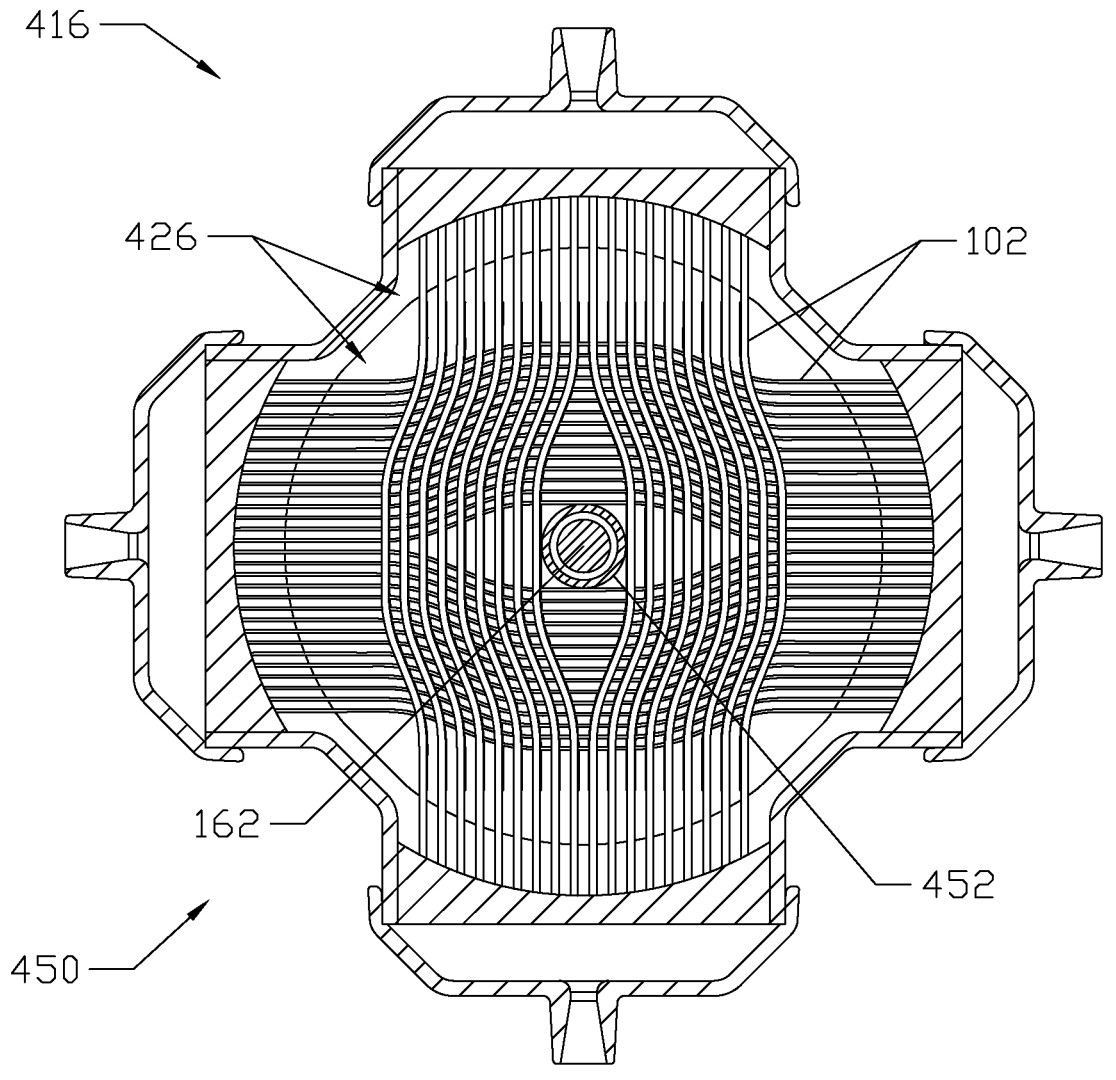

FIG. 26A shows a variation of the second reactor 450 in which the membranes 102 of a membrane plate assembly 426 are spaced evenly across substantially the entire width of a potting chamber 416. There is no shaft 162 extending past the membranes 102 as in FIG. 2. FIG. 26B shows another variation of the second reactor 450 in which the membranes 102 of a membrane plate assembly 426 are spaced evenly across substantially the entire width of a potting chamber 416. In this example, there is a shaft 162 extending past the membranes 102 as in FIG. 2 but the membranes 102 have sufficient excess length, or slack, to bend around the shaft. The shaft 162 may be placed in a bushing 452 to avoid friction between the shaft 162 and the membranes 102.

FIG. 27 shows a variation of the second reactor 450 in which the mold 400 has smaller panels 408. Optionally, the mold 400 may be made substantially without panels 408. Reducing or removing the panels 408 may allow a larger portion of the extra-capillary space to be crossed by membranes 102.

Figure 28A:
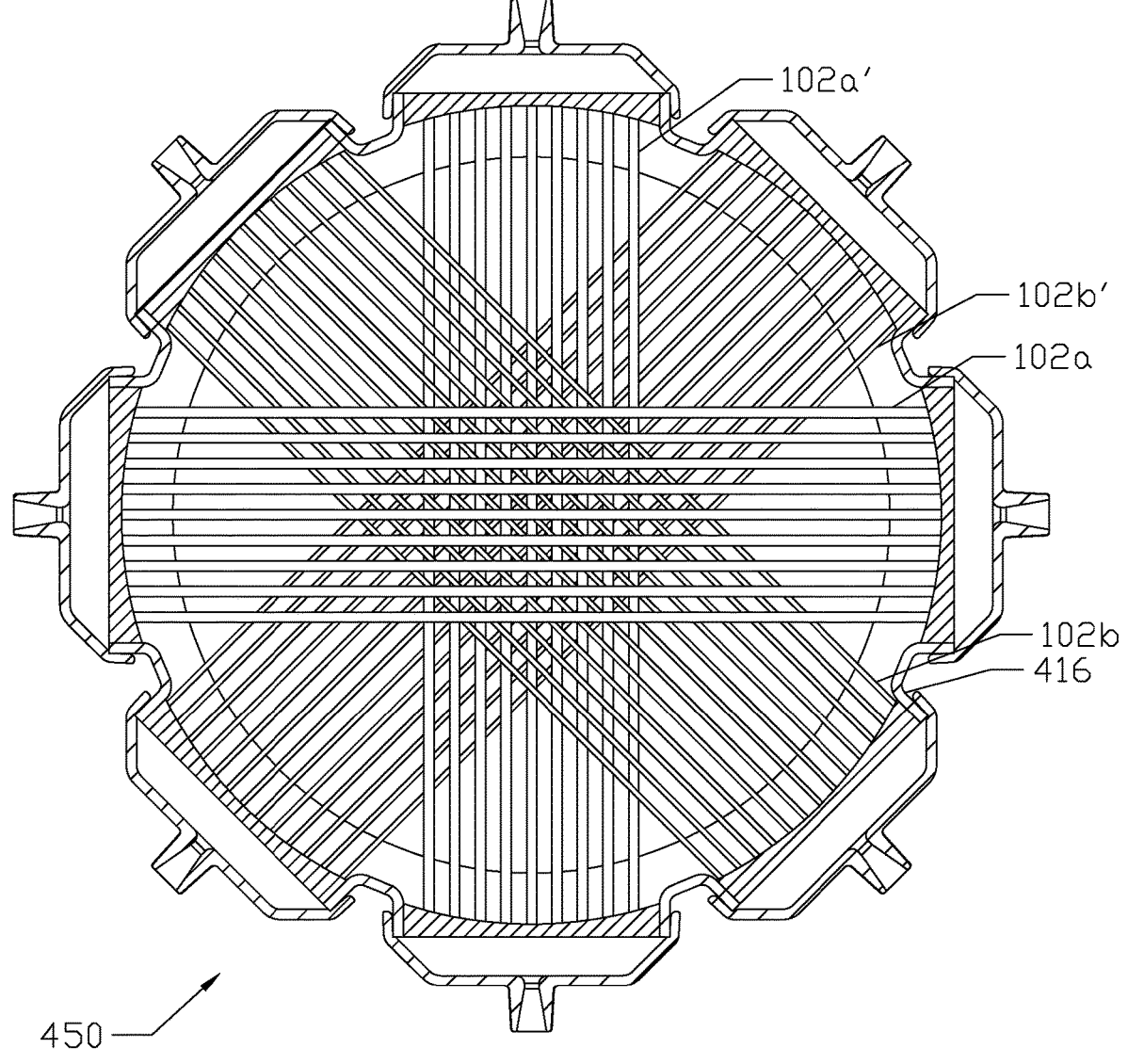
FIGS. 28A and 28B show cross-sections of further alternative second reactors.
Figure 28B:
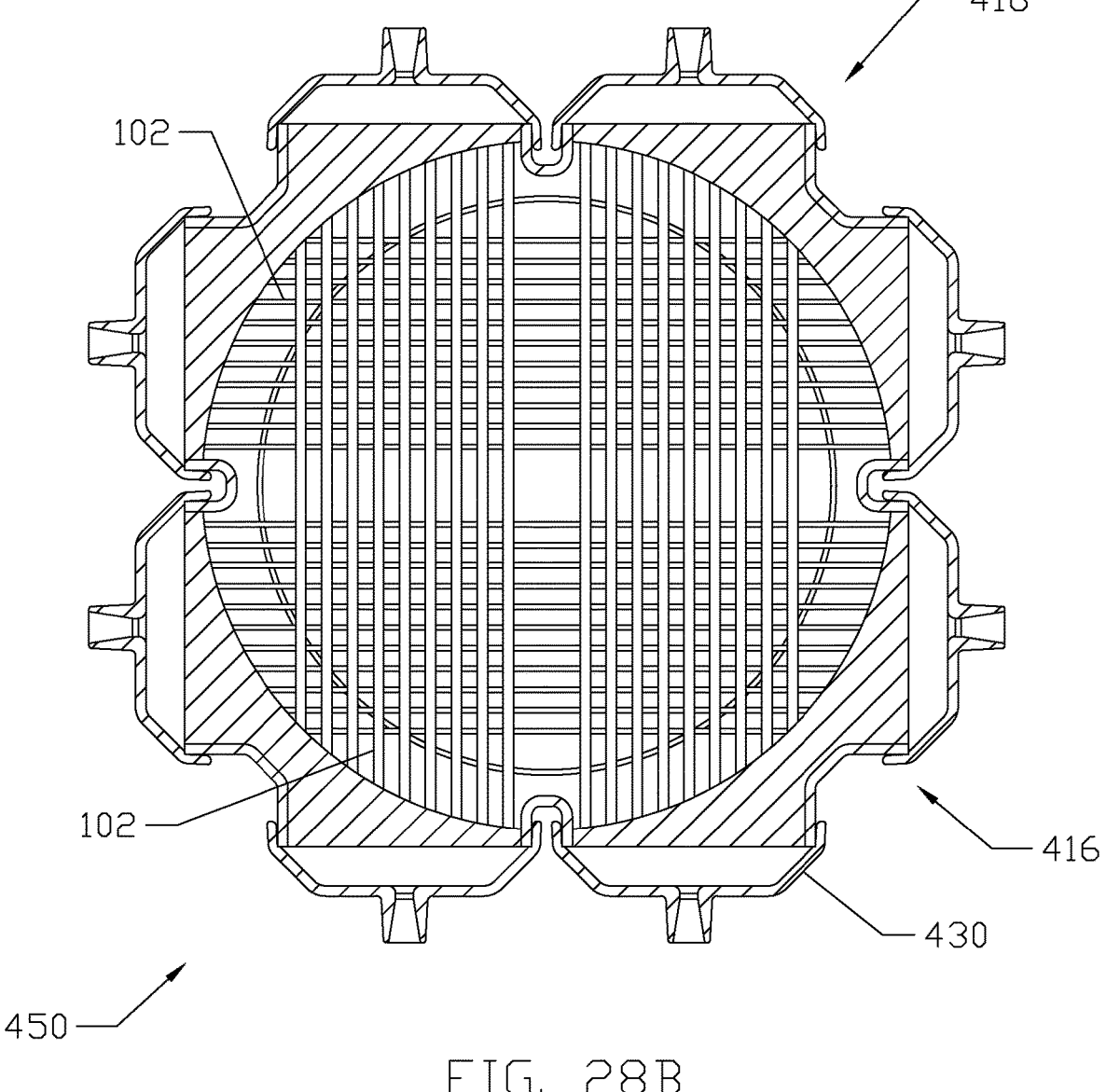

FIGS. 28A and 28B show variations of the second reactor 450 having additional potting chambers 416. In the examples shown, there are eight potting chambers 416. In other examples, a second reactor 450 may have between 2 and 20 potting chambers. In FIG. 28A, the potting chambers 416 are distributed radially around the second reactor 450. In FIG. 28B, one or more sides of the second reactor have no potting chambers or 2 or more potting chambers 416. Optionally, a second reactor 450 may have two different types of perfusion membranes 102a and 102a' or two different types of gas transfer membranes 102b and 102b'. The different types of membranes may differ, for example, in pore size, material or surface treatment.

FIG. 29A shows a compound reactor 550. The compound reactor 550 shown has three second elements 402 stacked together. The second elements 402 may have any of the variations shown in FIG. 23, 26A, 26B, 27, 28A or 28B or other variations. Alternatively, a different number, for example between 2 and 20, second elements 402 may be stacked together. An aperture 410 on the bottom of a first second element 402 fits into an aperture 410 on the top of another second element 402 below the first second element 402. The apertures 410 of two different second elements 402 are optionally bonded together to enhance a seal between the apertures 410. A base plate 438 is connected to an aperture 410 on the bottom of the lowest second element 402 of the compound reactor 550. In the example shown, the base plate 438 contains a mixer 160 connected to a shaft 162. The shaft 162 extends through the stack of second elements 402 and is connected to a motor 446. Alternatively, a base plate 438 as in FIG. 24 or a magnetic 444 as in FIG. 25 may be used.

The extra-capillary spaces of the second elements 402 are in fluid communication with each other through the apertures 410 to form one larger extra-capillary space of the entire compound reactor 550. However, the membranes 102 of each second element 402 can be individually accessed through the cap ports 434 on the caps 430 of the individual second elements 402. Each second element 402 in the example shown therefore provides two zones, a gas transfer zone and a perfusion zone, in a different location of the compound reactor 550.

Figure 29B:
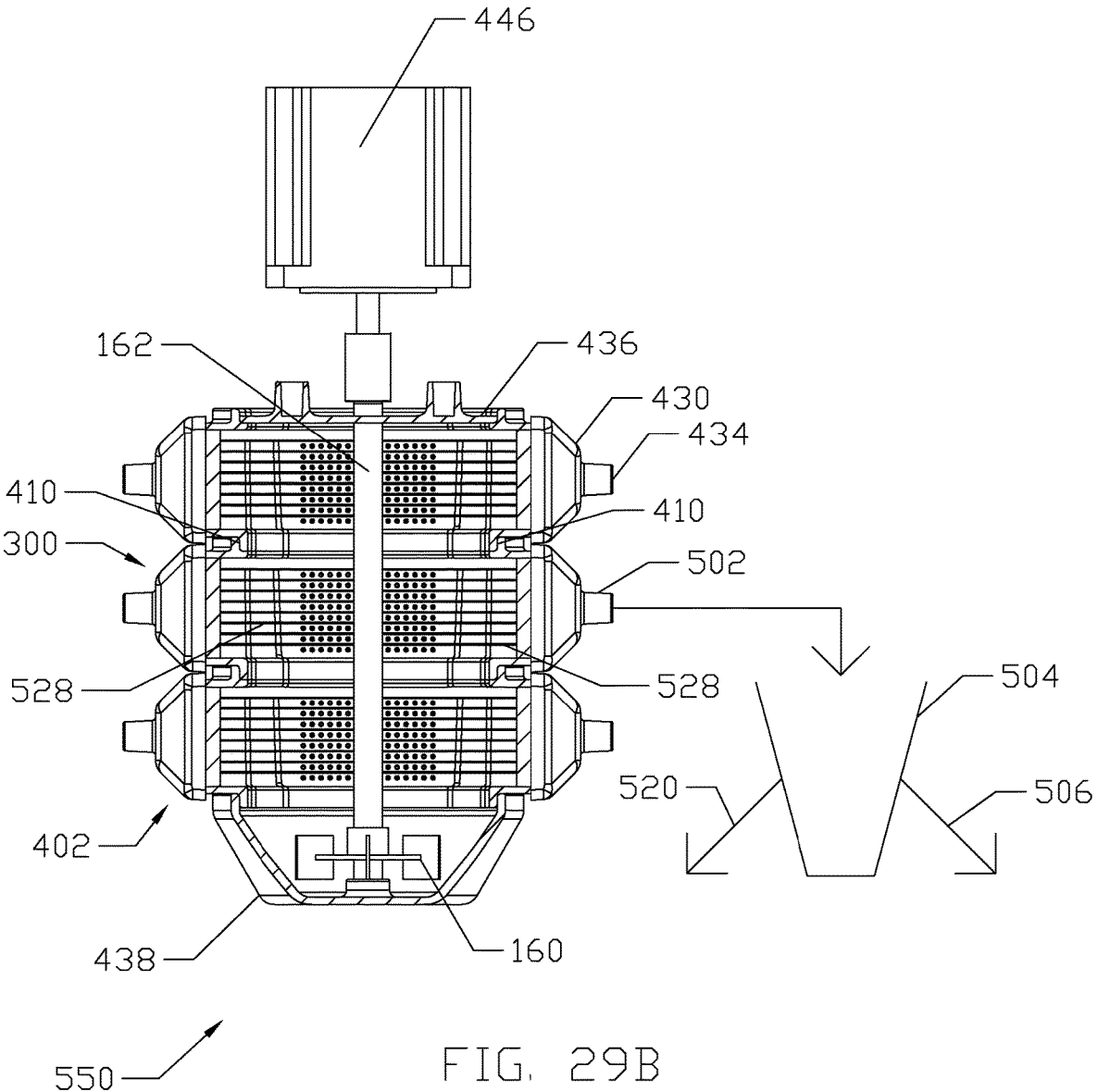

FIG. 29B shows another compound reactor 550. In this example, the compound reactor 550 has a harvest layer 300 as well as one or more second elements 402. The harvest layer 300 has one or more harvest ports 502 in communication with the lumens of exclusion membranes 528. The exclusion membranes 528 are potted in the harvest layer 300 in a manner analogous to the membranes 102 of a second element 402. The harvest layer 300 can be used to withdraw a portion of the first media along with a product while selectively excluding at least some of the productive cells, which remain in the rest of the first media. A product may be, for example, enucleated red blood cells, a virus, a protein or another cell product. In the example shown, first media with enucleated red blood cells and a reduced concentration of nucleated precursor cells is extracted from the harvest layer 300. One harvest port 502 is connected to the inlet of an apheresis module 504. The apheresis module 504 further separates enucleated red blood cells 506 from nucleated cells 520. The enucleated red blood cells 506 are a product. Optionally, the apheresis module may also allow some of the first media and nucleated cells 520 to be recovered and returned to the compound reactor 550. The apheresis module 504 may be, for example, a neonatal leukoreduction filter. The exclusion membranes 528 may have pores of about 5 microns in diameter for retaining nucleated erythroid precursor cells, or a smaller diameter for selectively harvesting virus or proteins.

Figure 29C:
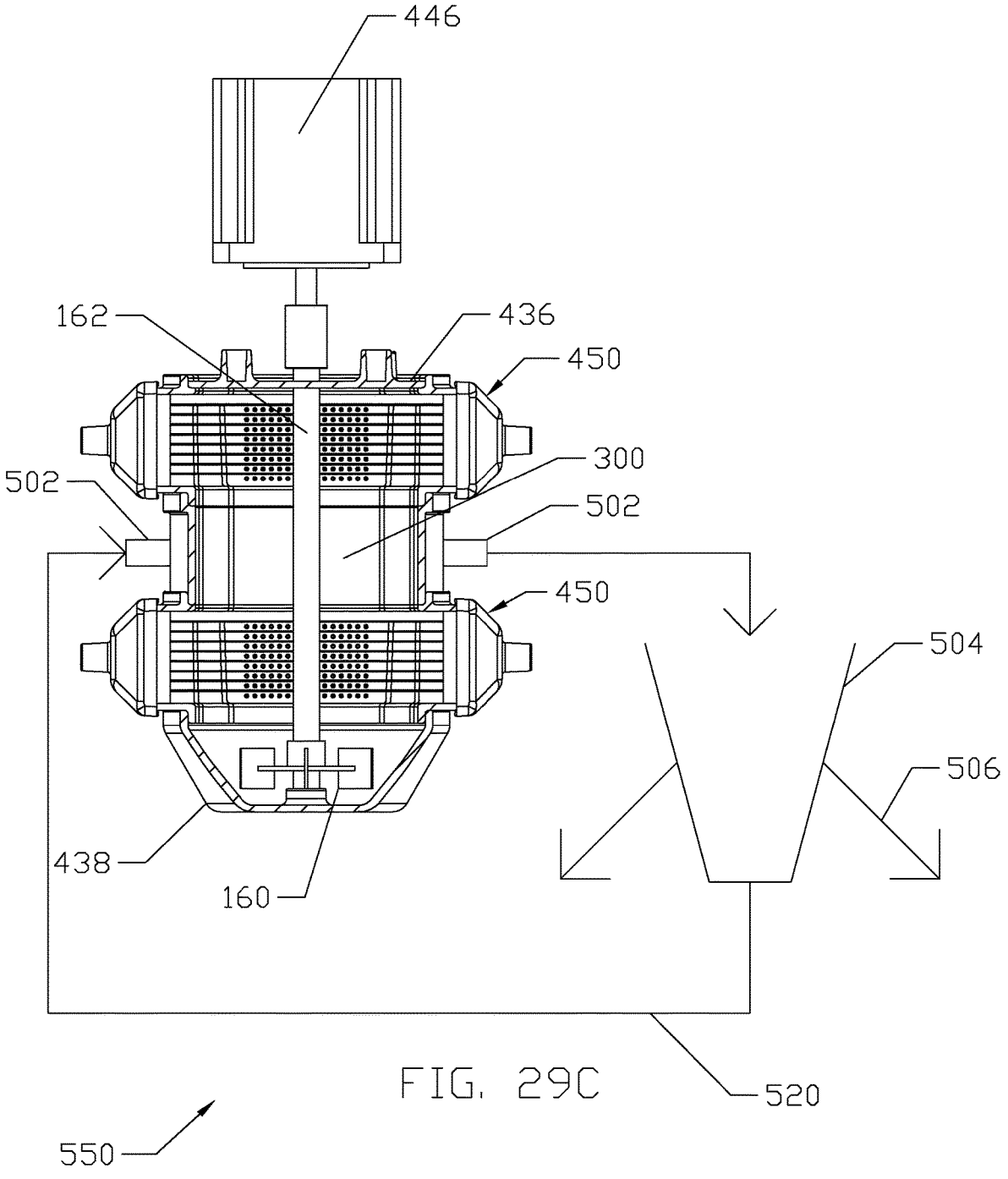

FIG. 29C shows another compound reactor 550. In this example, the compound reactor 550 has a harvest layer 300 as well as one or more second elements 402. The harvest layer 300 has one or more harvest ports 502 directly in fluid communication with the extra-capillary space of the compound reactor 550. The harvest layer 300 can be used to withdraw cells for transfer to another reactor or for collecting the cells as a product. In the example shown, one harvest port 502 is connected to the inlet of an apheresis module 504. The apheresis module 504 separates enucleated red blood cells 506 from nucleated erythroid precursor cells 520. The enucleated red blood cells 506 are a product, for example for red blood cell therapy or transfusion. The nucleated cells 520 are returned to the extra-capillary space of the compound reactor 550 through another harvest port 502 to continue production of enucleated red blood cells 506. The apheresis module 504 may be, for example, a leukoreduction filter system.

Figure 30A:
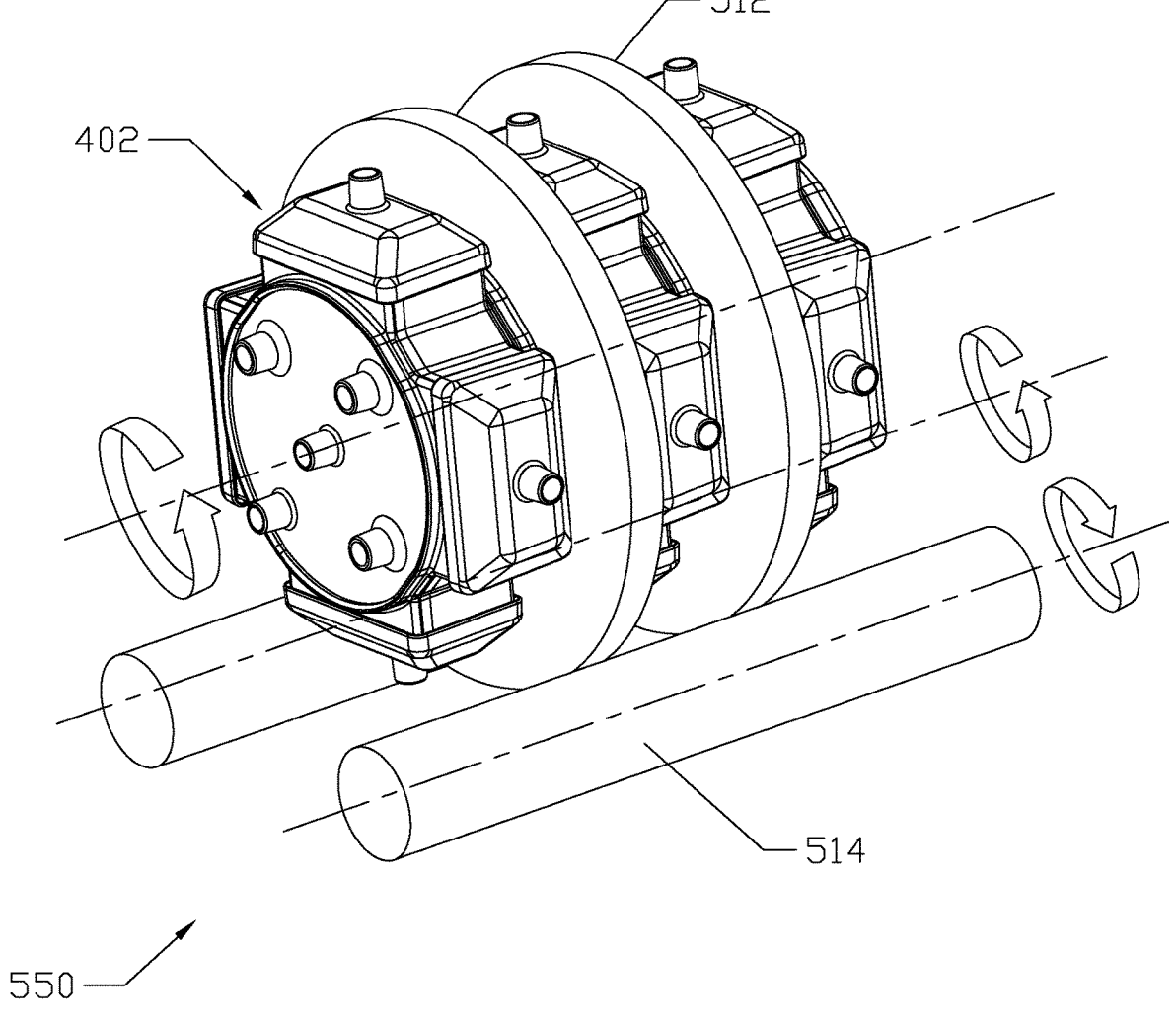
FIGS. 30A and 30B show alternative devices for rotating a compound reactor.

FIG. 30A shows another compound reactor 550. The compound reactor 550 has discs 512 inserted between pairs of second elements 402. Alternatively or additionally, discs 512 could be provided at the ends of the compound reactor 550. The discs 512 rest on a pair of rollers 514. The rollers 514 can be driven by a motor (not shown) to rotate the compound reactor 550 to provide mixing in the extra-capillary space. Tubing to carry a fluid to or from a second element 402 may pass through a hole or notch (not shown) in a disc 512.

Figure 30B:
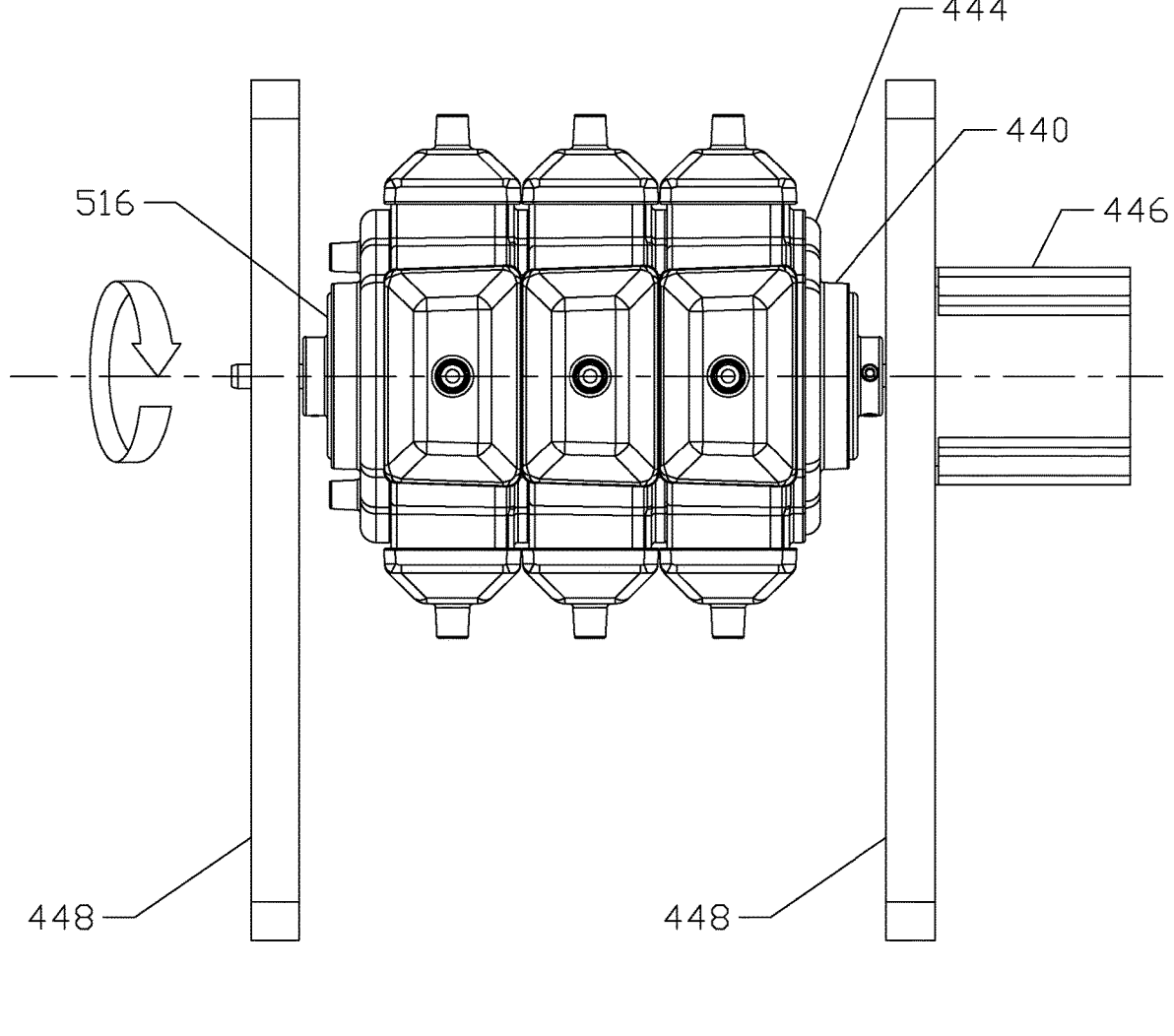

FIG. 30B shows another compound reactor 550. This compound reactor 550 is mounted at both ends on a stand

448. One end of the stand 448 has a motor 446 that rotates a magnet 440. The magnet 440 is connected to a magnetic base 444 attached to one end of the compound reactor 550. The other end of the compound reactor 550 has a pinned top plate 516 supported in a bushing on the other end of the stand 448. The motor 446 can be used to rotate the compound reactor 550 to provide mixing in the extra-capillary space.

Figure 31:
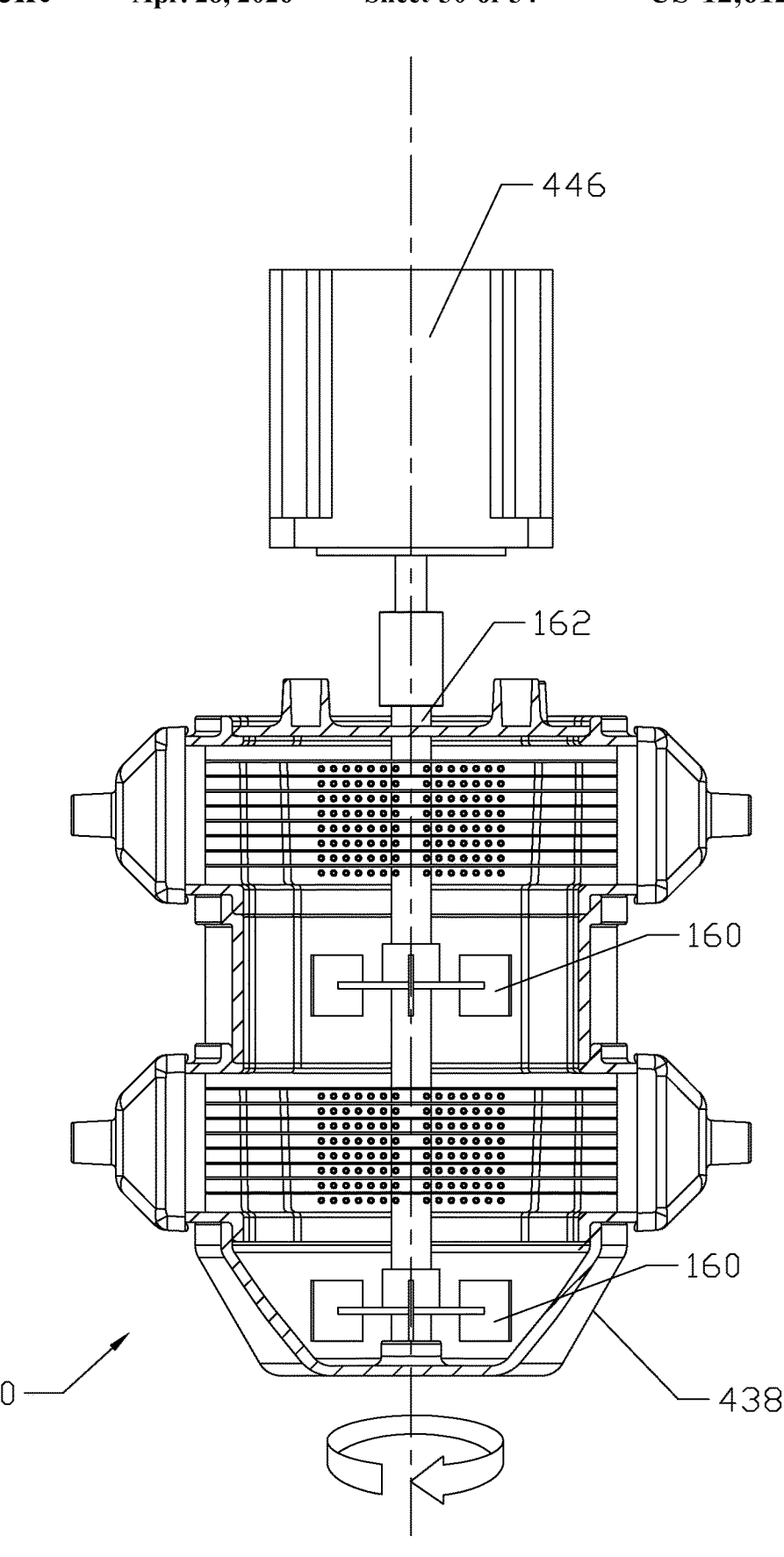
FIG. 31 shows an alternative compound reactor with a mixing layer between two second elements.

FIG. 31 shows another compound reactor 550. The compound reactor 550 has a first mixer 160 in a base plate 438. The compound reactor 550 also has a second mixer 160 at the top of the compound reactor 500 or in an intermediate position as shown. Optionally, more than two mixers 160 may be provided. The mixers 160 may differ from the first mixer 160, for example in diameter, pitch, or type of blades. Multiple mixers 160 maybe mounted to a common shaft 162.

Figure 32A:
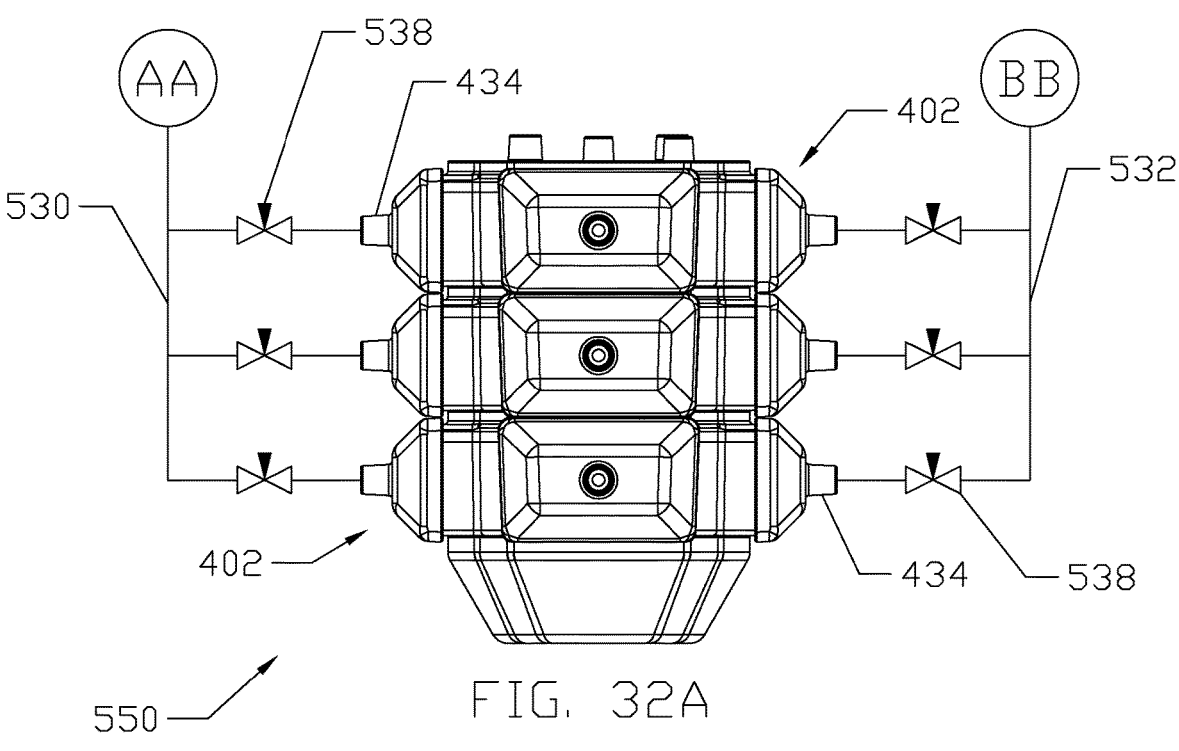
FIGS. 32A and 32B show a compound reactor with headers and manifolds connected to its second elements.

FIG. 32A shows a compound reactor 550 with a liquid perfusion manifold 530. The liquid perfusion manifold 530 connects a media supply point AA to a set of cap ports 434. In the example shown, these cap ports 434 are in fluid communication with the upstream ends of perfusion membranes 102a (not visible in FIG. 32A) in the compound reactor 550. Optionally, the branches of the liquid perfusion manifold 530 have control valves 538 that allow the flow of media to be adjusted or stopped to a selected second element 402. The compound reactor 550 also has a liquid perfusion header 532. The liquid perfusion header 532 connects a set of cap ports 434 to a media collection point BB. In the example shown, these cap ports 434 are in fluid communication with the downstream ends of perfusion membranes 102a (not visible in FIG. 32A) in the compound reactor 550. Optionally, the branches of the liquid perfusion header 532 have control valves 538 that allow the flow of media to be adjusted or stopped to a selected second element 402. The liquid perfusion manifold 530, liquid perfusion header 532 and control valves 538 allow the flow of media to be adjusted to all of the second elements 402 or to one set of the second elements 402 relative to another set of second elements 402. In some examples, it is sufficient to have a single control valve 538 either upstream or downstream of a second element 402. However, having control valves 538 both upstream and downstream of the compound reactor may provide additional control options. For example, selecting between an upstream control valve 538 and a downstream control valve 538 to adjust media flow may affect the pressure inside of a second element 402. In another example, one set of control valves 538 (either upstream or downstream of the compound reactor 550) may be linked together (for example mechanically, electrically or in a control algorithm) to provide simultaneous adjustments in flow of media to all of the second elements 402 while the other set of control valves 538 are controlled individually to make adjustments in the flow of media to one second element 402 relative to another second element 402. In the example show, the liquid perfusion manifold 530 and liquid perfusion header 532 have three branches but in other examples the liquid perfusion manifold 530 and liquid perfusion header 532 may have a different number of branches corresponding to a different number of second elements 402 in a compound reactor 550.

Figure 32B:
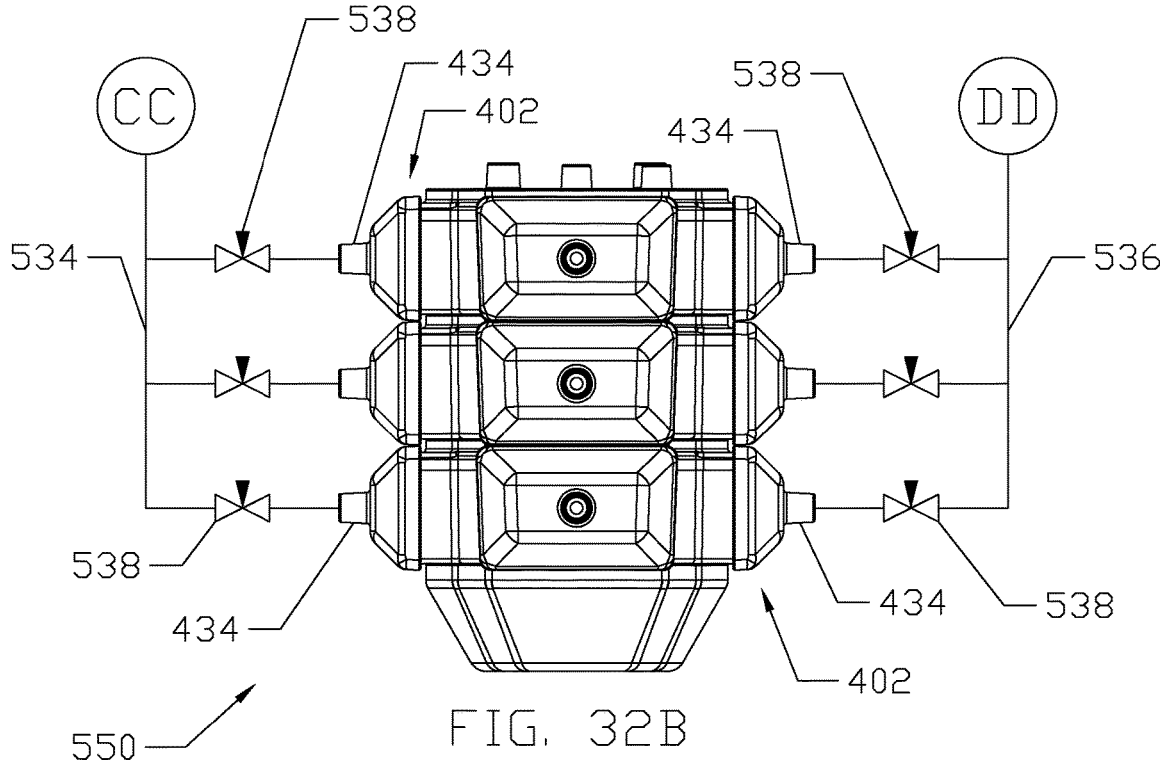

FIG. 32B shows a compound reactor 550 with a gas perfusion manifold 534 connecting a gas supply point CC to a set of cap ports 434. In the example shown, these cap ports 434 are in fluid communication with the upstream ends of gas transfer membranes 102b (not visible in FIG. 32B) in the compound reactor 550. Optionally, the branches of the gas perfusion manifold 533 have control valves 538 that allow the flow of gas to be adjusted or stopped to a selected second element 402. The compound reactor 550 also has a gas perfusion header 536 connected to a set of cap ports 434 to a gas collection point DD. In the example shown, these cap ports 434 are in fluid communication with the downstream ends of gas transfer membranes 102b (not visible in FIG. 32B) in the compound reactor 550. Optionally, the branches of the gas perfusion header 536 have control valves 538 that allow the flow of media to be adjusted or stopped to a selected second element 402. The gas perfusion manifold 534, gas perfusion header 536 and control valves 538 allow the flow of gas to be adjusted to all of the second elements 402 or to one set of the second elements 402 relative to another set of second elements 402. As discussed above the liquid media, control valves 538 may be provided either upstream or downstream of a second element 402 or both upstream and downstream. Selecting between an upstream control valve 538 and a downstream control valve 538 to adjust gas flow may affect the pressure inside of a second element 402. Optionally, one set of control valves 538 (either upstream or downstream of the compound reactor 550) may be linked together (for example mechanically, electrically or in a control algorithm) to provide simultaneous adjustments in flow of gas to all of the second elements 402 while the other set of control valves 538 are controlled individually to make adjustments in the flow of gas to one second element 402 relative to another second element 402. In the example show, the gas perfusion manifold 534 and gas perfusion header 536 have three branches but in other examples they may have a different number of branches corresponding to a different number of second elements 402 in a compound reactor 550.

Figure 33:
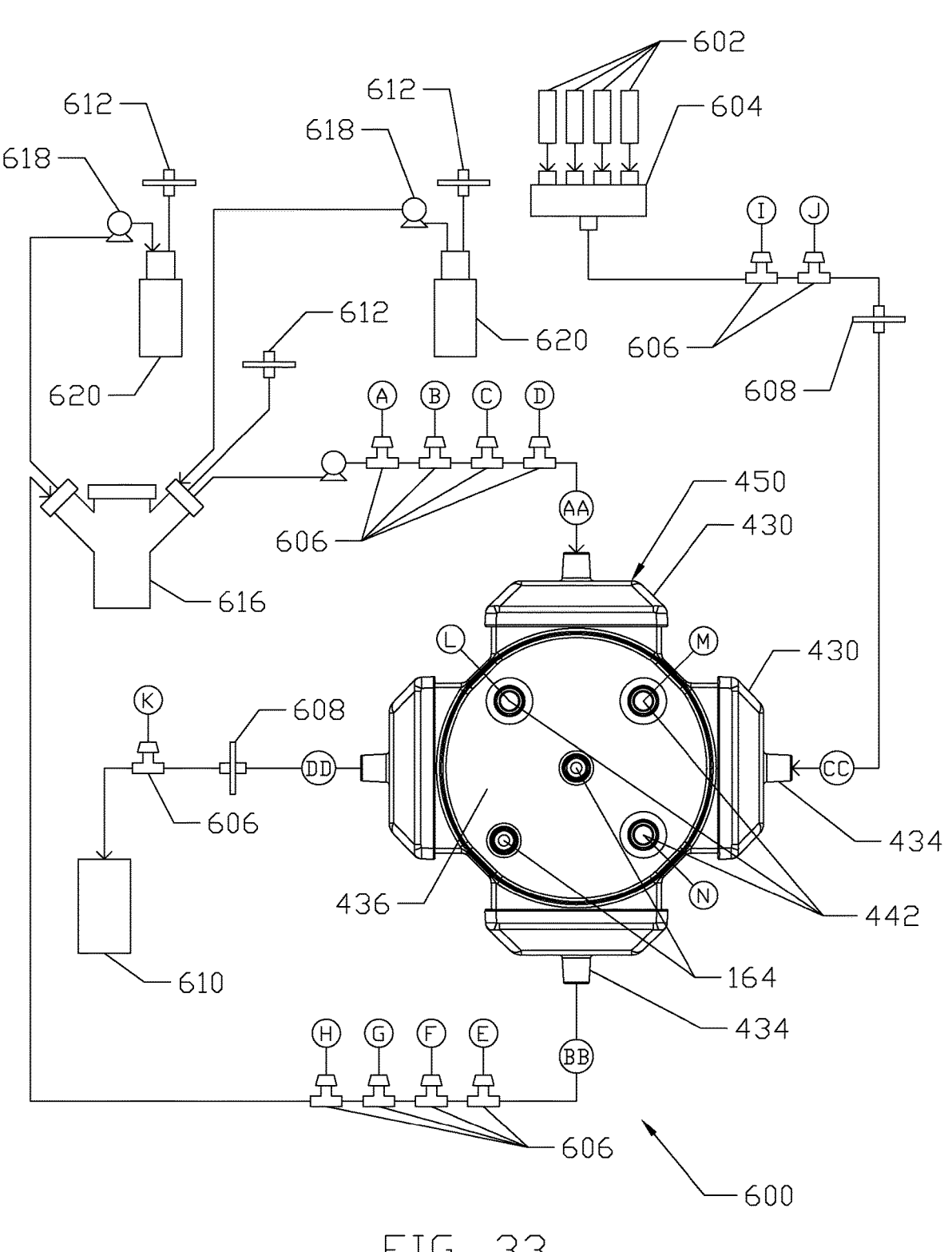
FIG. 33 shows a cell culture system.

FIG. 33 shows a cell culture system 600 including a second reactor 450. Optionally, a compound reactor 550 fitted with a liquid perfusion manifold 530, liquid perfusion header 532, gas perfusion manifold 534 and gas perfusion header 536 may be used in place of the second reactor 450. The extra-capillary space of the second reactor 450 may be filled with a first media through a fitting 164. The extra-capillary space may also be inoculated with cells that will be grown in the second reactor 450 through a fitting 164. After the extra-capillary space has been filled and inoculated, the fittings 164 are attached to filtered gas vents 612 (shown in other parts of FIG. 33 but not attached to the fittings 164). In some examples, the gas vents 612 include a membrane, for example with 0.22 micron pores, that allows gasses to pass through but prevents bacterial contamination of the second reactor 450. In some examples the membrane is hydrophobic and retains liquids. Optionally, a fitting 164 may be connected, periodically or continuously, to a sampler (not shown). The sampler can be used to withdraw samples of first media, and compounds dissolved and/or suspended in the first media, from the extra-capillary space. Optionally, one or more compounds may be added to the extra-capillary space through a fitting 164. For example, a growth factor may be added to the extra-capillary space to make up for the decay or consumption of growth factors originally present in the first media.

Figure 35:
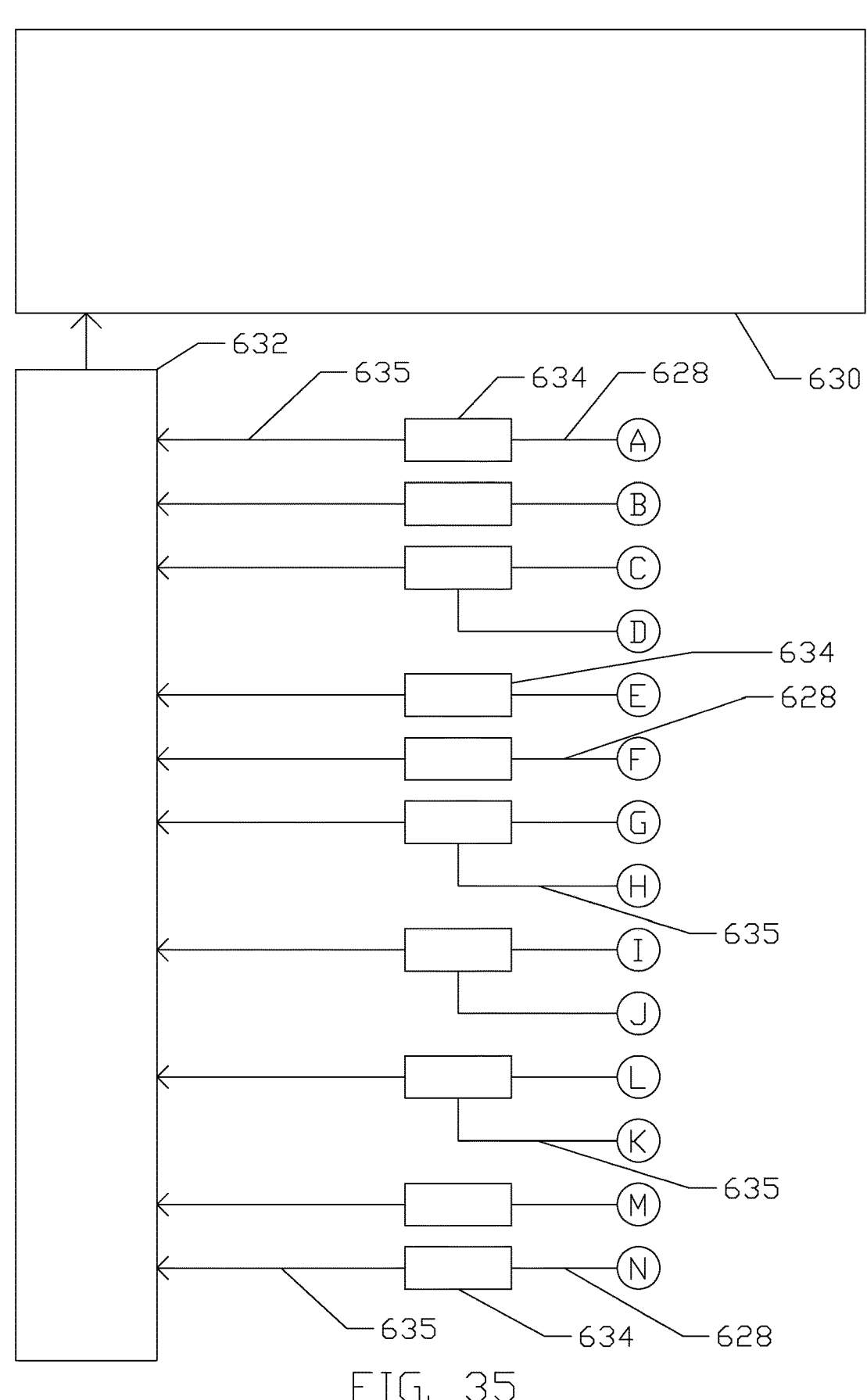
FIG. 35 shows additional parts of the cell culture system of FIG. 33.

The second reactor 450 has one or more sensors L, M, N in communication with the ECS through the top plate 436. In the example shown, sensors L, M, N sense the pH, dissolved oxygen concentration and dissolved carbon dioxide concentration of the first media in the extra-capillary space. Optionally, each sensor L, M, N is attached to an adapter 442 over a hole in the top plate 436. The sensor L, M, N has a probe body that is sealed to the adapter 442. The probe body has a sensor dot that is in liquid communication with the first media in the ECS. The adapter 442 also holds a fiber optic cable 628 (shown in FIG. 35) in a position suitable to probe the sensor dot. Referring to FIG. 35, the fiber optic cable 628 is connected to a fiber optic meter 634. The fiber optic meter 634 is connected to a computer 630, optionally though a USB hub 632. The computer 630 receives and optionally displays readings of pH, dissolved oxygen concentration and dissolved carbon dioxide concentration of the first media in the extra-capillary space. Optionally, the computer 630 may control any of the controllable elements, for example pumps or valves, in the cell culture system 600. When a compound reactor 550 is used, a set of sensors similar to sensors L, M, N may be provided in the panels 408 of each second element 402.

One or more gasses are provided to the second reactor 450 from one or more compressed gas tanks 602. In the example shown, there are compressed gas tanks 602 for oxygen, carbon dioxide, nitrogen and air. The gasses flow through tubing into a gas mixer 604, which produces a gas blend. The gas blend passes through tubing past one or more inline sensors 606 and through an inline gas filter 608 to a cap 430 of the second reactor 450. In the example shown, inline sensors 606 I and J sense the oxygen concentration and temperature of the gas blend. The gas blend flows from the cap 430, through gas transfer membranes 102b inside the second reactor 450, to an opposing cap 430. The gas blend then flows through more tubing, another in line gas filter 608 and one or more additional inline sensors 606 to an off-gas analyzer 610. In the example shown, inline sensor K senses the temperature of the gas blend leaving the second reactor 450. In the example shown, the off-gas analyzer measures the carbon dioxide concentration and the oxygen concentration of the gas blend.

Optionally, a flow control valve may be provided before or after the second reactor 450 to control the flow rate of gas through the second reactor 450. Where a compound reactor 550 is used as the second reactor 450, the tubing to and from the compound reactor 550 may be connected to a gas perfusion manifold 534 and gas perfusion header 536, optionally with control valves 538, as described in relation to FIG. 32B to allow the flow of gas to be controlled for one or more individual second elements 402.

A second media is provided to the second reactor 450 from a spinner flask 616. Optionally, second media may be added to the spinner flask 616 from a bottle 620 connected to a peristaltic pump 618. Second media may also be removed from the spinner flask 616 by another peristaltic pump 618 connected to another bottle 620. Second media is drawn from the spinner flask 616 by another peristaltic pump 618 and passes through one or more inline sensors 606 to a cap 430 of the second reactor 450. In the example shown, inline sensors 606 A, B, C and D sense the dissolved oxygen concentration, pH, dissolved carbon dioxide concentration and temperature of the second media. The second media flows from the cap 430, through perfusion membranes 102a inside the second reactor 450, to an opposing cap 430. The second media then flows through more tubing and one or more additional inline sensors 606 back to the spinner flask 616. In the example shown, inline sensors 606 E, F, G, and H sense the dissolved oxygen concentration, pH, dissolved carbon dioxide concentration and temperature of the second media leaving the second reactor 450. Filtered gas vents 612 are provided to allow air to move in and out of the second media system while preventing contamination of the second media.

Optionally, a flow control valve may be provided before or after the second reactor 450 to control the flow rate of second media through the second reactor 450. Where a compound reactor 550 is used as the second reactor 450, the tubing to and from the compound reactor 550 may be connected to a liquid perfusion manifold 530 and gas perfusion header 532, optionally with control valves 538, as described in relation to FIG. 32A, to allow the flow of second media to be controlled for one or more individual second elements 402.

Optionally, the inline sensors 606 for pH, carbon dioxide concentration and oxygen concentration may be optical inline sensors. For example, optical inline sensors from PreSens have a fiber optic cable 628 connected to a fiber optic meter 634 as shown in FIG. 35. The fiber optic meter 634 is connected to a computer 630 through a wire 635. Other inline sensors 606, for example a temperature sensing thermocouple, may also be connected to the computer 630. As shown in FIG. 35, a wire 635 from a thermocouple may be joined to a fiber optic meter 634 before being connected to a USB port.

The cell culture system 600 shown is a small-scale system. Larger systems may be made, for example to operate a larger compound reactors 550, or to operate multiple second reactors 450 or multiple compound reactors 550 in parallel. A larger or other system can use different sizes or types of equipment or different arrangements of conduits, valves, flow control devices, sensors, pumps, heaters or other equipment than the cell culture system 600 to achieve similar functions.

Although the second media circulates outside of the second reactor 450, in contrast circulation of the first media is preferably minimized. Optionally there is no circulation of first media outside of the second reactor 450. The first media differs from the second media as determined by the pore size of the perfusion membranes 102a. In some examples, the perfusion membranes 102a may have a molecular weight cut off (MWCO) selected in the range of 5,000 to 250,000 Da. Cells, virus, and molecules above the MWCO are retained in the first media. Large molecules retained in the extra-capillary space can include, for example, growth factors and proteins. In some examples, the first media contains large molecules, such as growth factors, that materially affect the cost of a cell culture process. By retaining these large molecules in the first media, and minimizing or eliminating circulation of the first media outside of the second reactor 450, the amount of these large molecule that are required to operate a process is reduced. Retaining large molecules or other products of the process in a limited volume of the first media can also help with harvesting these products. Since the membranes 102 exclude cells, they also prevent any contamination, for example by bacteria, in the gas or second media parts of the system from contaminating product cells or product producing cells in the extra-capillary space.

Despite the separation of the first media into the extra-capillary space by the membranes 102, the second media and gasses can influence the first media. For example, the flow of a gas or second media through the membranes 102 can be used to cool (or heat) the first media. The carbon dioxide concentration and pH of the first media can be influenced, for example, by acids, bases or buffers provided to the first media through the perfusion membranes 102a or by adding or removing carbon dioxide from the first media through the gas transfer membranes 102b. Some nutrients, with sizes small enough to pass through the pores of the perfusion membranes 102a, can also be provided to the first media from the second media. Small cell respiration products, which may be inhibitory, can also be removed from the first media by diffusion into the second media through the perfusion membranes 102a.

Figure 34:
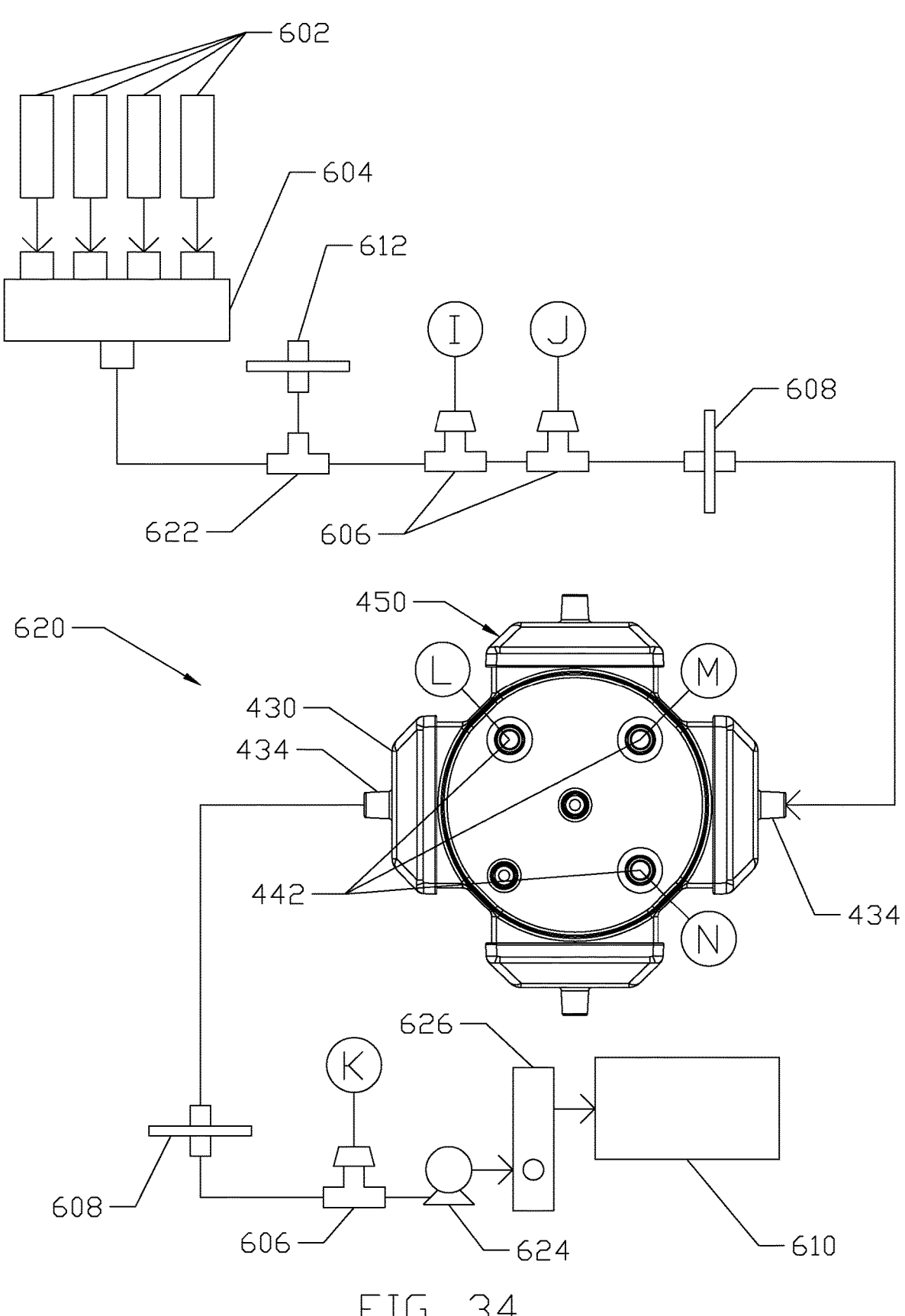
FIG. 34 shows an alternative gas system for use with the cell culture system of FIG. 33.

FIG. 34 shows an alternative gas system 620 for the cell culture system 600 of FIG. 33. In the alternative gas system 620, a gas mixture travels from the gas mixer 604 to a pressure break 622. The pressure break 622 may be a T-junction with a filtered gas vent 612 on one arm. Excess gas is vented to the atmosphere from the alternative gas system 620 through the pressure break 622. Optionally, the vented stream may be controlled with a valve. Optionally, a pressure regulator or other flow control valve may be used in place of, or in addition to, the pressure break 622. A gas pump 624 downstream of the second reactor 450 draws some of the gas mixture under vacuum through the gas transfer membranes 102b. A rotameter 626, or optionally a mass flow meter, measures the flow of the gas mixture before it travels to an off-gas analyzer 610. Optionally, the rotameter 626 may be used to provide a signal for use in a feed back or other control loop connected to the gas pump 624 or the pressure break 622 or both. The pressure break 622 and the gas pump 624 may be selectively configured such that the insides of the gas transfer membranes 102b are pressurized, under a partial vacuum, or under pressure at an upstream end and under a partial vacuum at a downstream end. A gas, for example oxygen, can flow from the gas transfer membranes 102b to the first media if there is sufficient partial pressure of the gas inside the gas transfer membranes 102b relative to the concentration of the gas in the first media. A gas can be delivered to the first media even if the total pressure of the gas mixture inside the gas transfer membranes 102b is less than atmospheric, or less than the pressure of the first media surrounding the gas transfer membranes 102b.

In some cases with the gas system shown in FIG. 33, the total pressure of the gas mixture, or the partial pressure of one or more particular gasses, inside the gas transfer membranes 102b may cause undesirable consequences. For example, the pressure of the gas mixture inside of the gas transfer membranes 102b may be sufficient to cause one or more gasses to form bubbles in the first media. While the total pressure of the gas mixture can be regulated, an undesirable pressure may be required to provide a desired flow rate of the gas mixture. Changing to the alternative gas system 620 of FIG. 34 may allow for a different combination of gas pressure and flow rate that better suits a particular process. In the case of a compound reactor 550, control valves 538 as shown in FIG. 32B may also be used to control the flow of gas through individual second elements 402.

Erythroid precursor cells tend to expand faster and differentiate into red blood cells under low oxygen partial pressure. A high oxygen transfer capacity (kLa) is needed to support a large and/or rapidly growing population of cells. However, the oxygen transfer is preferably not driven by having areas of high dissolved oxygen concentration in direct communication with cells in the ECS. The gas transfer membranes 102b assist in maintaining a hypoxic environment in the ECS that still supports a high cell density by providing oxygen transfer that is well controlled and generally homogenously distributed throughout the extra-capillary space.

Products are typically harvested from a bioreactor by withdrawing media containing the product through a simple port. In some examples, after separating a harvested component, the non-harvested components may be returned to the reactor. Even with such recycle, it is likely that some useful material is lost from the media and the volume of media required is increased by the volume of the harvesting loop. Optionally, a harvest layer 300 can be configured to provide one or more separation steps. For example, in the case of cultured red blood cells, a suspension of cells may be removed from a reactor and separated in a first step into a) enucleated cells and b) a mixture of nucleated cells and nuclei. The mixture may be separated in a second step to extract the nucleated cells for recycle to the reactor from the nuclei, which are waste. Optionally, the harvest layer 300 is configured to perform part of the first step, i.e. nucleated cells are selectively retained in the reactor while enucleated cells are selectively extracted from the reactor. The degree of separation does not need to be a complete separation to be useful and a second separation of enucleated cells from nucleated cells may occur outside of the reactor. In another example, where the bioreactor 150, 450, 550 is used to produce virus in cells, the produced virus may be extracted through the harvest layer 300 while the cells are retained in the bioreactor. In another example, where cells in the bioreactor 150, 450, 550 are used to produce a protein or other product, the product may be extracted through the harvest layer 300 while the cells are retained in the bioreactor 150, 450, 550.

In batch filtration, the extra-capillary space (ECS) is filled initially to a generally constant volume. In a fed-batch process, the ECS is filled to an initial volume. At one or more later times, media is added to the ECS (without removing media). In a continuous process, media is added and removed continuously (which could include, for example, in pulses or at other discrete time intervals). However, the continuous process may also be operated such that the volume of the ECS in the reactor remains generally constant or such that the volume of the media in the ECS changes, for example increases, over time.

The turn down ratio of a bioreactor is the ratio of the largest volume of media that can be in the reactor while it is operating to the smallest volume of media that can be in the reactor while it is operating. In the reactors 150, 550 herein, the turn down ratio is determined based on the volume of media in the ECS. A large turn down ratio can be useful in some processes because, for example, a small number of cells can be used to inoculate the reactor 150, 550 at a high density. It is not necessary to inoculate the entire reactor volume. As the cell population increases, more media is added to dilute the ECS to a desired cell density. In a reactor 150, 550 as described herein with multiple elements 140 or second elements 402, turn down is enabled by shutting down the perfusion, and optionally gas, flow to elements 140 or second elements 402 that are not yet filled with media in their ECS. For example, a first element 140 or second element 402 at the bottom of the reactor 150, 550 may be filled with first media and inoculated. Later, first media is added to the ECS to submerge one or more other elements 140 or second elements 402. The valves related to these elements 140 or second elements 402 are then opened to provide perfusion and/or gas exchange to the newly submerged elements 140 or second elements 402. The reactor 150, 550 can thus be operated in a fed-batch mode or generally with perfusion and with a variable amount of media in the ECS.

In another mode of operation multiple reactors 150, 450, 550 can be operated with distinct ECSs but with their membranes 102 linked. For example the second media perfusion and/or gas perfusion ports of multiple reactors 150, 450, 550 can be connected in parallel. Because of the membranes 102, cells in the ECS of one reactor 150, 450, 550 cannot enter the ECS of another reactor 150, 450, 550.

In that way cells of the same type but drawn from different donors or intended for different patients can be cultured simultaneously but separately. Although each cell population is different in some way, the cell population dynamics are sufficiently similar such that some second media perfusion or gas supply system components can be shared. Optionally the flow of second media or gas to an individual reactor 150, 450, 550 may be adjusted in a way analogous to the control of individual second elements 402 in a compound reactor 550 as described above.

The membranes 102 provide perfusion, i.e. delivery of a substance in a distributed manner. The membranes 102 also provide retention, i.e. the cells are retained in the ECS. The membranes 102 can also retain selected compounds in the ECS. This can decrease the amount of expensive elements, such as growth factors, that are required since the ECS is smaller than the entire bioreactor 150, 450, 550 and its recirculation loops. As these selected compounds are consumed or degrade, more of the selected compound can be added directly to the ECS without the addition of whole media. In this way, compounds that degrade at different rates can be added at appropriate rates.

A reactor 150, 450, 550 can be cooled (or heated) by cooling the second media or gas. This can make the reactor 150, 450, 550 more accessible than, for example, wrapping a reactor in a cooling jacket. Further, with a cooling jacket as reactor diameter increases there may be a temperature difference between the core and the jacket. With cooling delivered through the membranes 102, heat is removed from the center of the reactor 150, 450, 550.

The mixers 160 provide bulk mixing but also disrupt boundary layers around the membranes 102. This disruption may increase a transfer rate associated with the membranes 102, but also tends to homogenize the transfer rates in different parts of the reactor. Even if cells are adhered to the membranes 102, or physically collected by a net of membranes 102, the first media moves, which helps to homogenize the delivery of gas and second media components. In a compound reactor 550 with multiple mixers, the mixer type, pitch or diameter can be varied within the compound reactor 550 to inhibit the formation of dead zones that do not have material movement of the first media. Movement of the first media can also be provided by moving the whole reactor 150, 450, 550, for example by rotation about any axis, rocking back and forth, inversion, rotation on an incline, or another movement that changes the direction of the gravity vector relative to the reactor 150, 450, 550.

Example

In an experimental example, a reactor similar to the second reactor 450 of FIG. 24 was used in a system similar to the cell culture system 600 of FIG. 33 but with an alternative gas system 620 generally as shown in FIG. 34 but with only two gas tanks 602, which supplied carbon dioxide and air. The system was used to grow HEK293F cells. The extra-capillary space of the reactor had a volume of 350 mL. The reactor had a Ruston impeller as a mixer located in the base of the reactor. The perfusion membranes were polyethersulphone (PES) hollow fiber membranes with a 10 kDa MWCO. The gas transfer membranes were poly-methylpentene (PMP) skinned hollow fiber membranes.

The impeller was rotated at between 50 and 150 RPM. The first media and the second media were the same. The media was supplied to the perfusion membranes from a peristaltic pump operating at 34 mL/min. The gasses were mixed to 8% $CO_2$ and drawn from a pressure break upstream of the reactor and through the gas transfer membranes by a pump downstream of the reactor at 100 mL/minute. The reactor was maintained at a temperature of 37 C by controlling the temperature of a hydroponic tent containing the reactor and other equipment. The reactor was sterilized in an autoclave for 30 minutes at 121 C.

The ECS of the reactor was filled with media and innoculated over a 24 hour period to an initial total cell density (TCD) and viable cell density (VCD) of $0.66*10^6$ per mL and $0.63*10^6$ per mL respectively. The flow of gas to the perfusion membranes and media to the perfusion media were commenced and continued for another three days. During the four day run, the pH of the media in the extra-capillary decreased from 7.6 to 6.9 indicating that cells were growing. TCD and VCD of $0.70*10^6$ per mL and $0.41*10^6$ per mL respectively were measured in media sampled from the extra-capillary space at the end of the trial. Shaking the reactor released clumps of cells from the membrane matrix. TCD and VCD of $1.42*10^6$ per mL and $0.90*10^6$ per mL respectively were measured in media sampled from the extra-capillary space after the shaking. The bioreactor was dismantled and additional clumps were observed still present within the hollow fiber membrane matrix, particularly in compound zones where the perfusion membranes overlapped with gas transfer membranes. The cell count data is not considered quantitatively accurate since the counts were made in an automated cell counter and cells in the clumps were not counted. However, the cell count data, pH data and presence of uncounted clumps of cells indicate that cells reproduced in the bioreactor. Further, viable cells were present both in suspension and restrained within the hollow fiber membrane matrix.

The description above provides several examples of reactors, parts of reactors, methods of making reactors and systems and processes to growing cells in the reactors. Any one or more aspects of one example may be combined with any one or more aspects of one or more other examples to provide further examples of reactors, parts of reactors, methods of making reactors and systems and processes to growing cells in the reactors.

We claim:

1. A bioreactor comprising,
   one or more elements,
   each element including layers of gas transfer membranes and layers of perfusion membranes, wherein the gas transfer membranes are oblique to the perfusion membranes,
   each element including potting material surrounding ends of the gas transfer membranes and potting material surrounding ends of the perfusion membranes, and,
   a motor adapted to rotate the one or more elements,
   wherein each element has a generally round interior cross section defined at least primarily by inner surfaces of the potting material.

2. The bioreactor of claim 1 wherein the potting material is provided in potting chambers separated by panels and the panels protrude into an extra-capillary space of the elements.

3. The bioreactor of claim 1 wherein the one or more elements have an axis generally perpendicular to the perfusion membranes and the gas transfer membranes, wherein the motor is adapted to rotate the one or more elements around the axis.

4. The bioreactor of claim 3 wherein the motor is in line with the axis.

5. The bioreactor of claim 4 wherein the motor is attached to a stand and connected to the one or more elements at a first end through a magnet.

6. The bioreactor of claim 5 wherein a second end of the one or more elements is supported by the stand.

7. The bioreactor of claim 5 wherein the motor is connected to one end of an element through a magnet and the other end of the element is unsupported.

8. The bioreactor of claim 3 wherein the one or more elements are supported on rollers.

9. The bioreactor of claim 8 wherein the motor rotates the rollers.

10. The bioreactor of claim 3 wherein the motor rocks the one or more elements.

11. The bioreactor of claim 3 wherein the motor periodically inverts the one or more elements.

12. The bioreactor of claim 3 wherein the motor rotates the one or more elements in one direction for 1-5 rotations and then rotates the one or more elements in the other direction for 1-5 rotations.

\*  \*  \*  \*  \*